US012692501B2

(12) United States Patent
Afonin et al.

(10) Patent No.: US 12,692,501 B2
(45) Date of Patent: Jul. 28, 2026

(54) APTAMER NANOFIBERS AND KILL-SWITCHES AND USES THEREOF

(71) Applicants: The University of North Carolina at Charlotte, Charlotte, NC (US); The Penn State Research Foundation, University Park, PA (US)

(72) Inventors: Kirill Afonin, Charlotte, NC (US); Nikolay Dokholyan, Hummelstown, PA (US)

(73) Assignees: The University of North Carolina at Charlotte, Charlotte, NC (US); The Penn State Research Foundation, University Park, PA (US)

( * ) Notice: Subject to any disclaimer, the term of this patent is extended or adjusted under 35 U.S.C. 154(b) by 906 days.

(21) Appl. No.: 17/816,273

(22) Filed: Jul. 29, 2022

(65) Prior Publication Data

US 2022/0403392 A1 Dec. 22, 2022

Related U.S. Application Data

(63) Continuation-in-part of application No. 17/090,596, filed on Nov. 5, 2020, now abandoned.

(60) Provisional application No. 63/109,691, filed on Nov. 4, 2020, provisional application No. 62/942,884, filed on Dec. 3, 2019.

(51) Int. Cl.
| | |
|---|---|
| *C12N 15/115* | (2010.01) |
| *B82Y 5/00* | (2011.01) |

(52) U.S. Cl.
CPC .............. *C12N 15/115* (2013.01); *B82Y 5/00* (2013.01); *C12N 2310/16* (2013.01); *C12N 2320/50* (2013.01)

(58) Field of Classification Search
CPC .............. C12N 15/115; C12N 2310/16; C12N 2320/50; C12N 2320/30; C12N 2310/3519; B82Y 5/00; A61K 31/7088
See application file for complete search history.

(56) References Cited

U.S. PATENT DOCUMENTS

| | | | |
|---|---|---|---|
| 7,201,898 B2 | 4/2007 | Monahan et al. | |
| 2004/0013645 A1 | 1/2004 | Monahan et al. | |

OTHER PUBLICATIONS

Ke et al., Nano Lett. (Jul. 2022) 22(14)5961-5972. (Year: 2022).*

* cited by examiner

*Primary Examiner* — J. E. Angell
(74) *Attorney, Agent, or Firm* — Myers Bigel, P.A.

(57) ABSTRACT

This invention relates to nanofibers comprising aptamers, which have increased stability and activity relative to free aptamers. The invention further relates to kill-switch nanofibers which disrupt the aptamer nanofibers. The invention further relates to methods of using the aptamer nanofibers and the kill-switch nanofibers to regulate the activity of extracellular targets recognized by the aptamers.

15 Claims, 19 Drawing Sheets

Specification includes a Sequence Listing.

| TREATMENT GROUP | CLOT (# OF ANIMALS) | CLOT (%) |
|---|---|---|
| CONTROL | 7/7 | 100 |
| ENOXAPARIN | 0/7 | 0 |
| NU APTAMERS | 5/6 | 83.3 |
| FIBERS | 5/6 | 83.3 |
| NU FIBERS | 3/9 | 33.3 |
| NU FIBERS + KS | 7/7 | 100 |

| TREATMENT | AT LEAST ONE RE-BLEEDING EPISODE | | (%) |
|---|---|---|---|
| NU APTAMER | 3/6 | | 50 |
| FIBER | 2/6 | | 33.3 |
| NU FIBER | 1/9 | | 11 |
| NU FIBER+KILL-SWITCH | 3/7 | | 42.8 |

| STANDARD CURVE | OD 550nm | | |
|---|---|---|---|
| (μL) | | | |
| 175 | 3.5520 | 3.5550 | 3.5570 |
| 100 | 2.701 | 2.681 | 2.674 |
| 75 | 2.132 | 2.116 | 2.131 |
| 50 | 1.619 | 1.600 | 1.588 |
| 25 | 0.769 | 0.758 | 0.758 |
| 10 | 0.475 | 0.466 | 0.457 |

APTAMER NANOFIBERS AND KILL-SWITCHES AND USES THEREOF

STATEMENT OF PRIORITY

This application is a continuation-in-part of U.S. application Ser. No. 17/090,596, filed Nov. 5, 2020, which claims the benefit of U.S. Provisional Application Ser. No. 62/942,884, filed Dec. 3, 2019, and U.S. Provisional Application Ser. No. 63/109,691, filed Nov. 4, 2020, the entire contents of each of which are incorporated by reference herein.

GOVERNMENT SUPPORT

This invention was made with government support under grant numbers R35GM139587 and R35GM134864 awarded by the National Institutes of Health. The government has certain rights in the invention.

STATEMENT REGARDING ELECTRONIC FILING OF A SEQUENCE LISTING

A Sequence Listing in XML format, submitted in accordance with 37 C.F.R. § 1.831-1.834, entitled 98129IP.xml, 39,309 bytes in size, generated on Jul. 29, 2022, and filed electronically, is provided in lieu of a paper copy. This Sequence Listing is hereby incorporated herein by reference into the specification for its disclosures.

FIELD OF THE INVENTION

This invention relates to nanofibers comprising aptamers, which have increased stability and activity relative to free aptamers. The invention further relates to kill-switch nanofibers which disrupt the aptamer nanofibers. The invention further relates to methods of using the aptamer nanofibers and the kill-switch nanofibers to regulate the activity of extracellular targets recognized by the aptamers.

BACKGROUND OF THE INVENTION

The process of blood coagulation involves a set of coagulation factors whose sequential activation leads to the formation of fibrin strands strengthening a platelet plug. The major function of the blood coagulation system is to maintain hemostasis by preventing bleeding. In addition, the coagulation system plays an essential role in innate immunity[1]. Coagulation triggered by damage to blood vessels or initiated by pathogens helps prevent blood loss or the spread of infection, respectively. Coagulation is normally followed by fibrinolysis to remove the clot, restore blood flow, and reinstate hemostasis. Some pathogens have developed fibrinolytic activity to escape the coagulation-controlled spread of infection. When a balance between the pro- and anticoagulant arms of the coagulation system is altered, its initially protective function can have harmful consequences to the host. For example, consumptive coagulopathy, also known as disseminated intravascular coagulation, is common in sepsis, allergic and autoimmune responses, tissue injury, and cancer[2-3]. Pathologic or excessive coagulation can lead to thrombosis; the latter can be categorized into either arterial thrombosis or venous thrombosis, both of which can result in myriad downstream symptoms[4]. Complications depend on where thrombosis occurs, and the main causes—hypercoagulability, endothelial cell injury, and venous stasis—are of increasing likelihood with age in combination with other lifestyle risk factors[5]. Overall, the multitude of ways that thrombosis may occur make it a leading cause of global mortality, responsible for an estimated one in four deaths worldwide[4]. Coagulopathy and thromboembolic events are the main causes of death in severe and critical COVID-19 patients[6-7].

Medicines aiming to prevent blood clots, commonly known as anticoagulants or blood thinners, are routinely used in short-term surgical procedures and long-term treatments of thrombosis. Prolonged anti-coagulation is required during certain medical procedures, e.g., coronary pulmonary bypass and extracorporeal membrane oxygenation. Currently, there are several commercially available anticoagulants, among which are vitamin K antagonists (e.g., COUMADIN®), heparins (e.g., FRAGMIN®, INNOHEP, and LOVENOX®)[8], Factor Xa inhibitors (e.g., XARELTO®, ELIQUIS®, and LIXIANA®), and direct thrombin inhibitors (e.g., ANGIOMAX®, ACOVA®, and PRADAXA®)[4, 9]. However, there are often side effects characteristic of these products, including excessive bleeding (hemorrhage) with further complications such as the passage of blood in urine, severe bruising, and bleeding gums, to name a few[5]. The efficacy of these anticoagulants is also dependent on the specific thrombosis indication as well as drug-drug interactions and patient conditions, including pregnancy. Large-scale trials are needed to explore efficacy with diversely represented patient cofactors[4]. Moreover, the patient's immune system often develops antibodies that neutralize anticoagulants, rendering them ineffective in controlling thrombosis[10]. Therefore, novel, effective, safe, and low-cost treatments of thrombosis with reversible control over the coagulation process are in high demand.

Aptamers are single-stranded nucleic acids selected in vitro for high affinity binding to target molecules[11]. The high specificity, low cost, batch-to-batch consistency, and biodegradability have set out aptamers as a promising class of therapeutics[12]. Moreover, unlike protein therapeutics and polysaccharide-based anticoagulants, aptamers were shown to be non-immunogenic, likely due to the natural immune tolerance to nucleic acids[13]. Several aptamers selected to target coagulation cascade proteins have been reported[14] along with reverse complements of aptamer sequences employed for their inactivation[15-20]. All three pathways that contribute to the blood coagulation cascade[21] share thrombin as a central protein, making it a promising target for the continued development of anticoagulants. Thrombin is a globular enzyme with three functional binding sites: the protease catalytic site, the anionic fibrinogen recognition site (exosite I), and the anionic heparin binding site (exosite II)[22]. Exosites I and II are located on opposite sides of thrombin and mediate its interactions with cofactors and substrates, while the catalytic site enables the serine protease activity of thrombin[23]. The first and the most studied thrombin-binding aptamer (HD1 or ARC183), was selected to be a 15-mer DNA G-quadruplex that inhibits coagulation by blocking the function of exosite I on thrombin[24-25]. Despite the medicinal promise, the suboptimal dosing and rapid clearance of ARC183 have halted further clinical trials of this formulation[26]. To improve the potency, numerous modifications of ARC183 have been introduced (e.g., RA-36,[27-28] and NU172[29-31]) but their short post-infusion half-lives with quickly restorable coagulation[32] hamper broader biomedical applications.

The present invention addresses unmet needs by providing improved therapeutic efficacy. The invention provides improved viral vectors for expression of IDS in the CNS and methods for treating or preventing MPS II.

SUMMARY OF THE INVENTION

This invention is based on the development of a user-friendly biomolecular platform based on modular RNA-DNA nanofibers comprising aptamers and programmed for reversible communication with extracellular targets and subsequent control of target activity via a "kill-switch" mechanism.

Thus, one aspect of the invention relates to a single strand DNA molecule comprising:

a) a polynucleotide of about 40 to about 70 nucleotides in length, the polynucleotide comprising:
    an RNA binding sequence of about 20 to about 30 nucleotides in length; and a toehold sequence of about 10 to about 20 nucleotides length linked to the 5' and 3' ends of the RNA binding sequence; and
  b) an aptamer linked to the 5' and/or 3' end of the polynucleotide;
  wherein the aptamer(s) binds an extracellular target.

Another aspect of the invention relates to a complex comprising the single strand DNA molecule as described herein, wherein the single strand DNA molecule is hybridized to a single strand RNA molecule of about 20 to about 30 nucleotides in length that is at least 80% complementary to the RNA binding sequence of the single strand DNA molecule.

A further aspect of the invention relates to a combination of a first single strand DNA molecule and a second single strand DNA molecule:

the first single strand DNA molecule comprising:
  a) a polynucleotide of about 40 to about 70 nucleotides in length, the polynucleotide comprising:
    an RNA binding sequence of about 20 to about 30 nucleotides in length; and
    a toehold sequence of about 10 to about 20 nucleotides length linked to the 5' and 3' ends of the RNA binding sequence; and
  b) an aptamer linked to the 5' and/or 3' end of the polynucleotide;
  wherein the aptamer(s) binds an extracellular target;
  the second single strand DNA molecule comprising:
  a) a polynucleotide of about 40 to about 70 nucleotides in length, the polynucleotide comprising:
    an RNA binding sequence of about 20 to about 30 nucleotides in length;
    a toehold sequence of about 10 to about 20 nucleotides length linked to the 5' and 3' ends of the RNA binding sequence, wherein the toehold sequence of the second single strand DNA molecule is at least 80% complementary to the toe hold sequence of the first single strand DNA molecule; and
  b) an aptamer linked to the 5' and/or 3' end of the polynucleotide;
  wherein the aptamer(s) binds an extracellular target.

An additional aspect of the invention relates to a complex comprising the combination of as described herein, wherein the first single strand DNA molecule and the second single strand DNA molecule are hybridized to a single strand RNA molecule of about 20 to about 30 nucleotides in length that is at least 80% complementary to the RNA binding sequence of each of the single strand DNA molecules in the combination.

Another aspect of the invention relates to a nanofiber comprising multimers of the complex of the invention.

A further aspect of the invention relates to a method of making the nanofiber of the invention, comprising combining the combination of the invention with a single strand RNA molecule of about 20 to about 30 nucleotides in length that is at least 80% complementary to the RNA binding sequence of each of the single strand DNA molecules in the combination under conditions where the toehold sequences of the first and second single strand DNA molecules can hybridize to each other.

An additional aspect of the invention relates to a kill-switch single strand DNA molecule, comprising a polynucleotide of about 40 to about 70 nucleotides in length, the polynucleotide comprising:

an RNA binding sequence of about 20 to about 30 nucleotides in length; and
  a toehold sequence of about 10 to about 20 nucleotides length linked to the 5' and 3' ends of the RNA binding sequence;
wherein the sequence of the polynucleotide is the reverse complement of the polynucleotide of the single strand DNA molecule of the invention.

Another aspect of the invention relates to a complex comprising the kill-switch single strand DNA molecule of the invention, wherein the kill-switch single strand DNA molecule is hybridized to a single strand RNA molecule of about 20 to about 30 nucleotides in length that is at least 80% complementary to the RNA binding sequence of the single strand DNA molecule.

A further aspect of the invention relates to a combination of a first kill-switch single strand DNA molecule and a second kill-switch single strand DNA molecule, the first kill-switch single strand DNA molecule comprising a polynucleotide of about 40 to about 70 nucleotides in length, the polynucleotide comprising:
  an RNA binding sequence of about 20 to about 30 nucleotides in length; and
  a toehold sequence of about 10 to about 20 nucleotides length linked to the 5' and 3' ends of the RNA binding sequence; and
  the second kill-switch single strand DNA molecule comprising a polynucleotide of about 40 to about 70 nucleotides in length, the polynucleotide comprising:
  an RNA binding sequence of about 20 to about 30 nucleotides in length; and
  a toehold sequence of about 10 to about 20 nucleotides length linked to the 5' and 3' ends of the RNA binding sequence, wherein the toehold sequence of the second kill-switch single strand DNA molecule is at least 80% complementary to the toe hold sequence of the first kill-switch single strand DNA molecule;
  wherein the first kill-switch single strand DNA molecule comprises a sequence that is the reverse complement of the polynucleotide of the first single strand DNA molecule of the combination of the invention; and the second kill-switch single strand DNA molecule comprises a sequence that is the reverse complement of the polynucleotide of the second single strand DNA molecule of the combination of the invention.

An additional aspect of the invention relates to a complex comprising the combination of the invention, wherein each of the first and second kill-switch single strand DNA molecules is hybridized to a single strand RNA molecule of about 20 to about 30 nucleotides in length that is at least 80% complementary to the RNA binding sequence of each of the kill-switch single strand DNA molecules in the combination.

Another aspect of the invention relates to a kill-switch nanofiber comprising multimers of the complex of the invention.

A further aspect of the invention relates to a method of making the kill-switch nanofiber of the invention, comprising combining the combination of the invention with a single strand RNA molecule of about 20 to about 30 nucleotides in length that is at least 80% complementary to the RNA binding sequence of each of the kill-switch single strand DNA molecules in the combination under conditions where the toehold sequences of the first and second kill-switch single strand DNA molecules can hybridize to each other.

An additional aspect of the invention relates to a method of binding an aptamer to an extracellular target, comprising contacting the extracellular target with the nanofiber of the invention.

Another aspect of the invention relates to a method of reversing binding of an aptamer to an extracellular target, comprising contacting an extracellular target bound to the nanofiber of the invention with the kill-switch nanofiber of the invention.

A further aspect of the invention relates to a method of inhibiting the activity of an extracellular target of, comprising contacting the extracellular target with the nanofiber of the invention, wherein the aptamer(s) in the nanofiber bind to and inhibit the activity of the extracellular target.

An additional aspect of the invention relates to a method of reversing inhibition of the activity of an extracellular target, comprising contacting the extracellular target bound to the nanofiber of the invention, wherein the aptamer(s) in the nanofiber bind to and inhibit the activity of the extracellular target, with the kill-switch nanofiber of the invention.

Another aspect of the invention relates to a method of regulating the activity of an extracellular target, comprising inhibiting activity by contacting the extracellular target with the nanofiber of the invention and then reversing the inhibition of activity by contacting the extracellular target bound to the nanofiber of the invention with the kill-switch nanofiber of the invention.

A further aspect of the invention relates to a method of inhibiting thrombin activity, comprising contacting thrombin with the nanofiber of the invention, wherein the aptamer(s) in the nanofiber bind to and inhibit thrombin activity.

An additional aspect of the invention relates to a method of reversing inhibition of thrombin activity, comprising contacting thrombin bound to the nanofiber of the invention, wherein the aptamer(s) in the nanofiber bind to and inhibit thrombin activity, with the kill-switch nanofiber of the invention.

Another aspect of the invention relates to a method of regulating thrombin activity, comprising inhibiting thrombin activity by contacting the thrombin with the nanofiber of the invention and then reversing the inhibition of thrombin activity by contacting thrombin bound to the nanofiber of the invention with the kill-switch nanofiber of the invention.

These and other aspects of the invention are set forth in more detail in the description of the invention below.

6 indicated. (C) Anticoagulant fibers bind to thrombin preventing the blood clotting cascade. (D) Kill-switches bind to anticoagulant fibers causing reinstatement of thrombin function and producing smaller assemblies for accelerated renal excretion.

Figure 2:
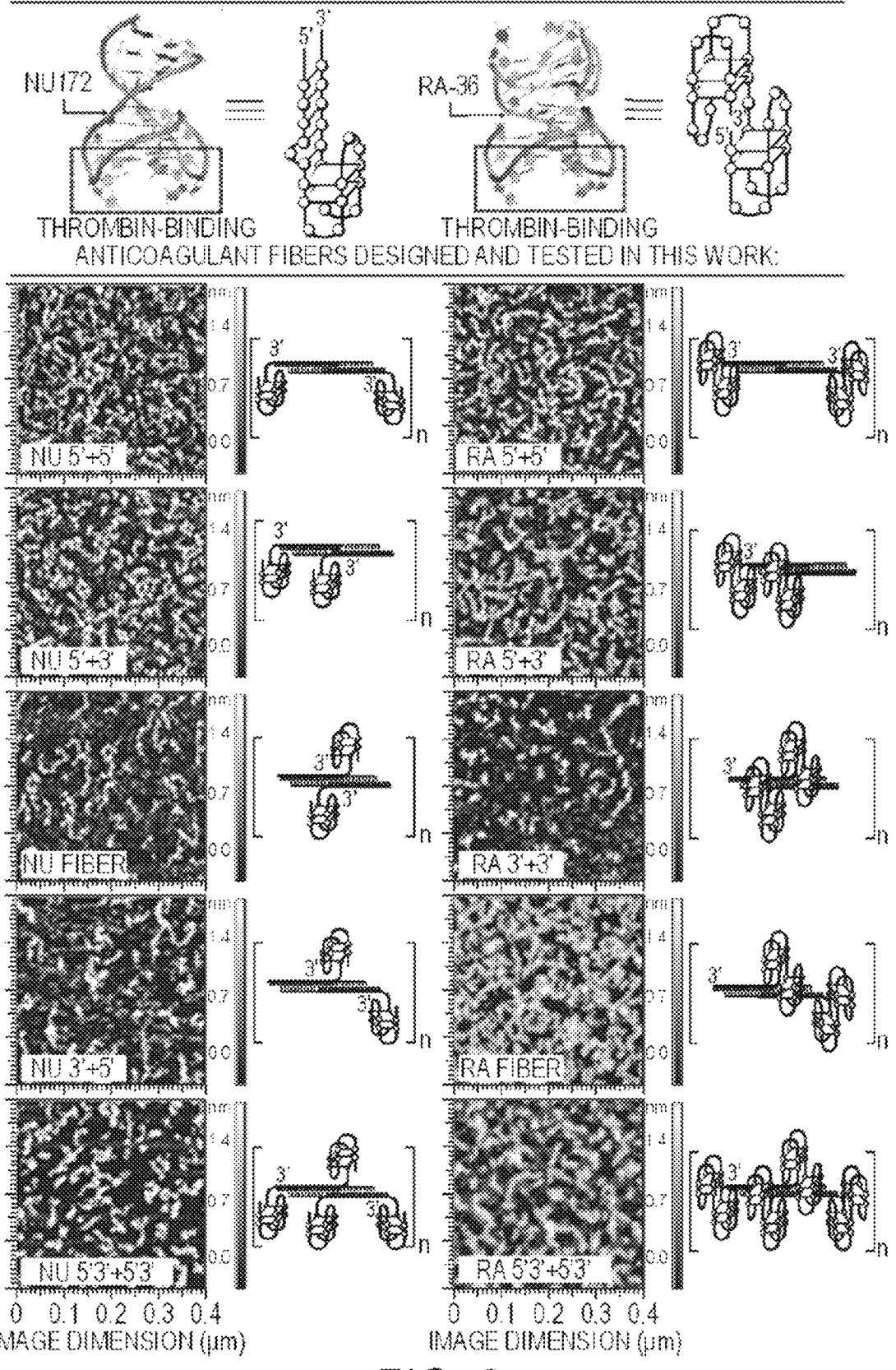

FIG. 2 shows the formation of anticoagulant fibers visualized by atomic force microscopy (AFM).

Figure 3A:
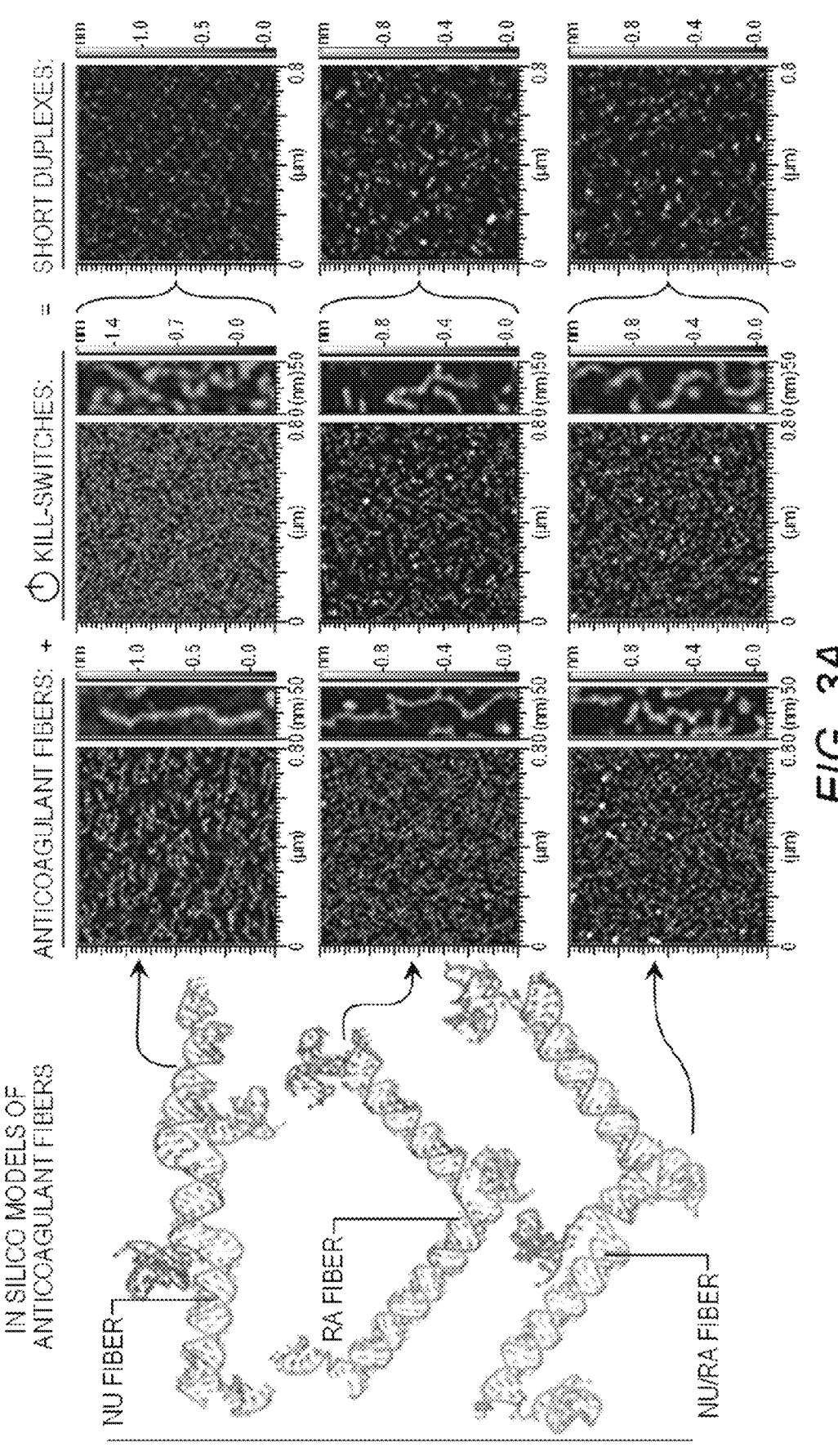
Figures 3B, 3C:
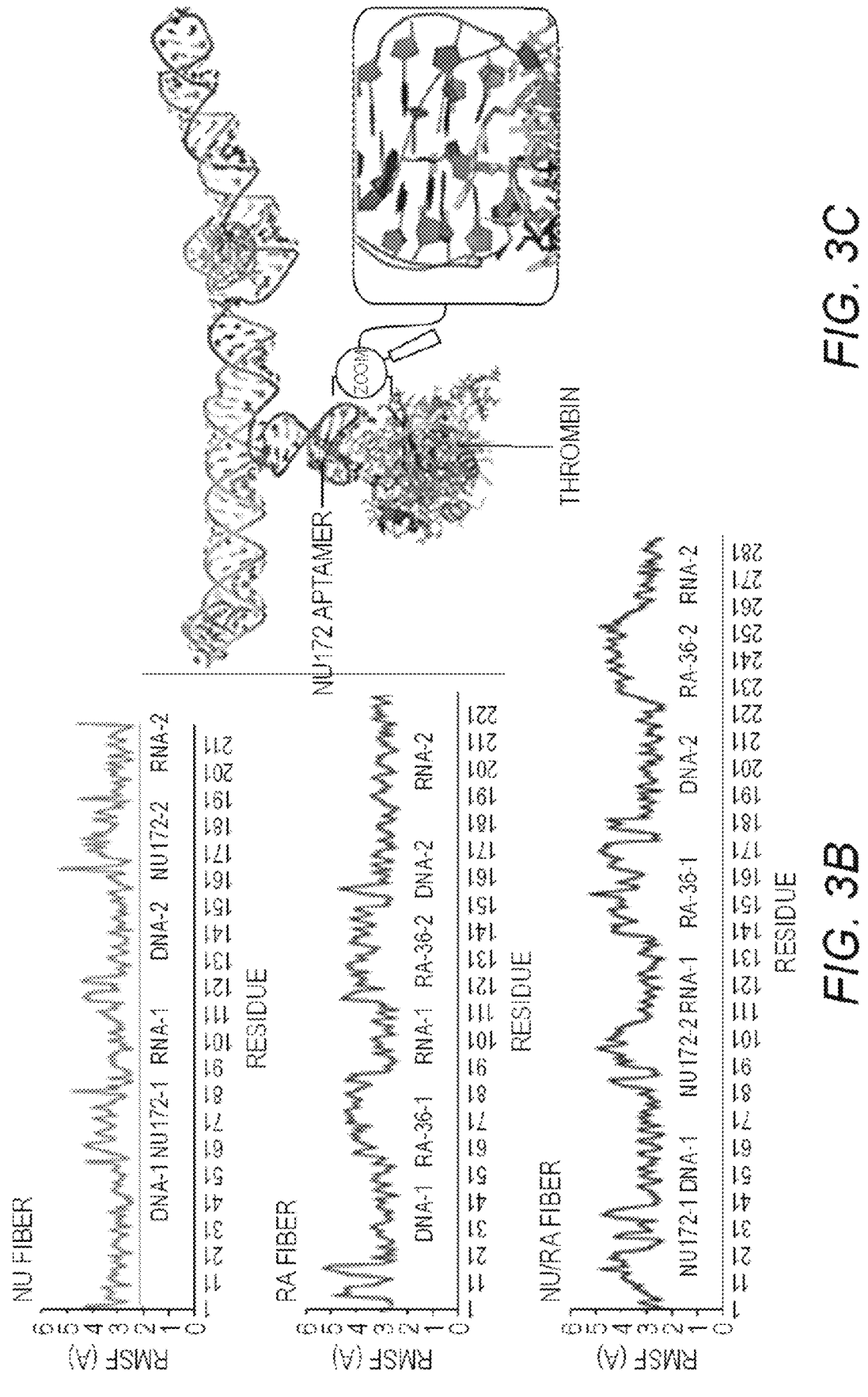

FIGS. 3A-3C show the characterization of anticoagulant fibers. (A) 3D structures and AFM images of fibers, kill-switches, and their re-association products. Based on the models, the distances between the aptamers in each structure were estimated (Table 2). (B) Root mean square fluctuation (RMSF) of NU, RA, and NU/RA fibers, and (C) modeled interactions of NU fiber and thrombin. The numbered residues indicate where the interactions occur.

Figure 4:
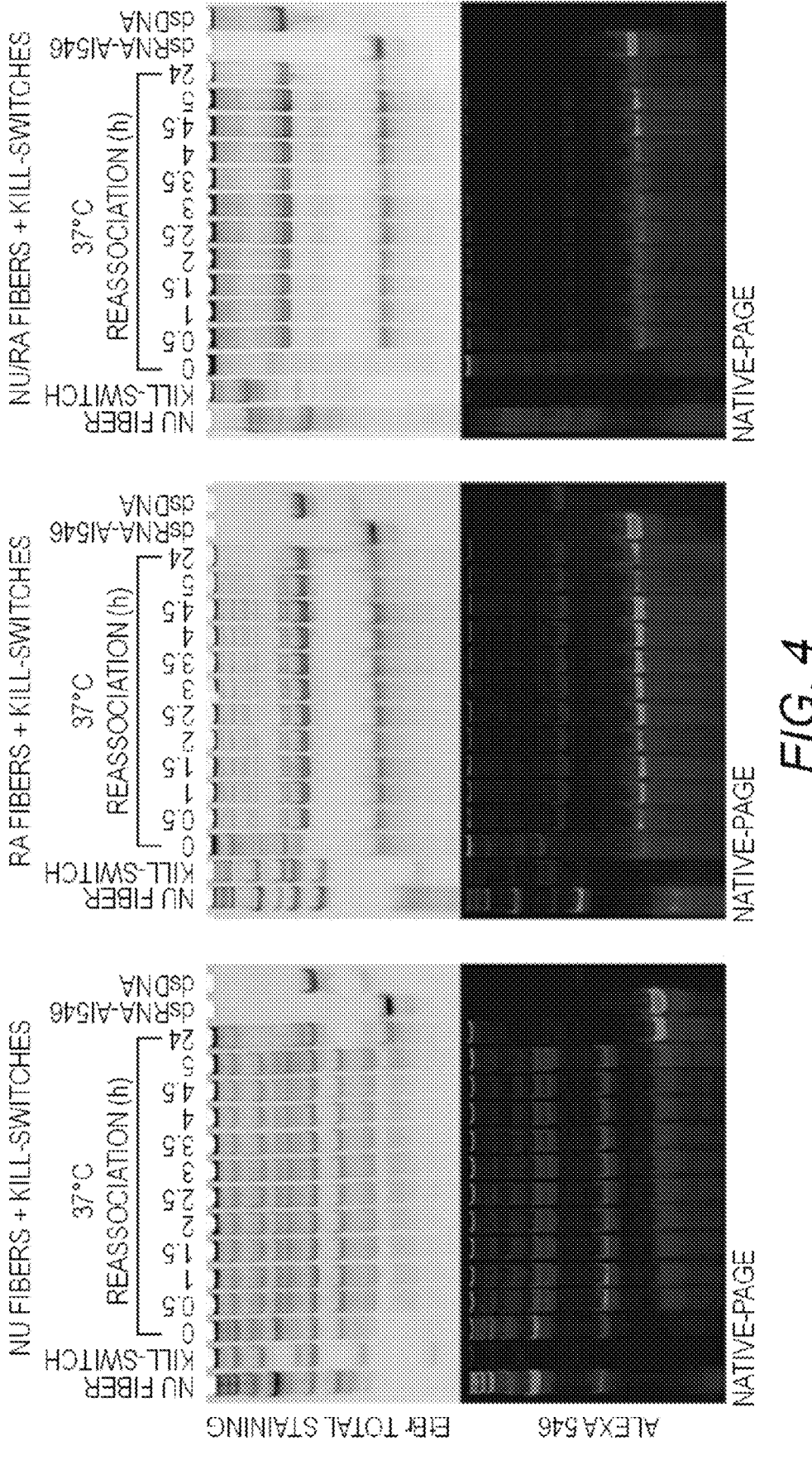

FIG. 4 shows in vitro characterization of anticoagulant fibers and kill-switches. The reassociation of anticoagulant fibers and corresponding kill-switches at various timepoints was analyzed by native-PAGE. Fluorescently labeled RNA-DNA fibers were incubated at 37° C. together with corresponding kill-switches. Over a five-hour period, the reassociation process was monitored every half hour and then incubation was continued up to 24 hours.

Figure 5:
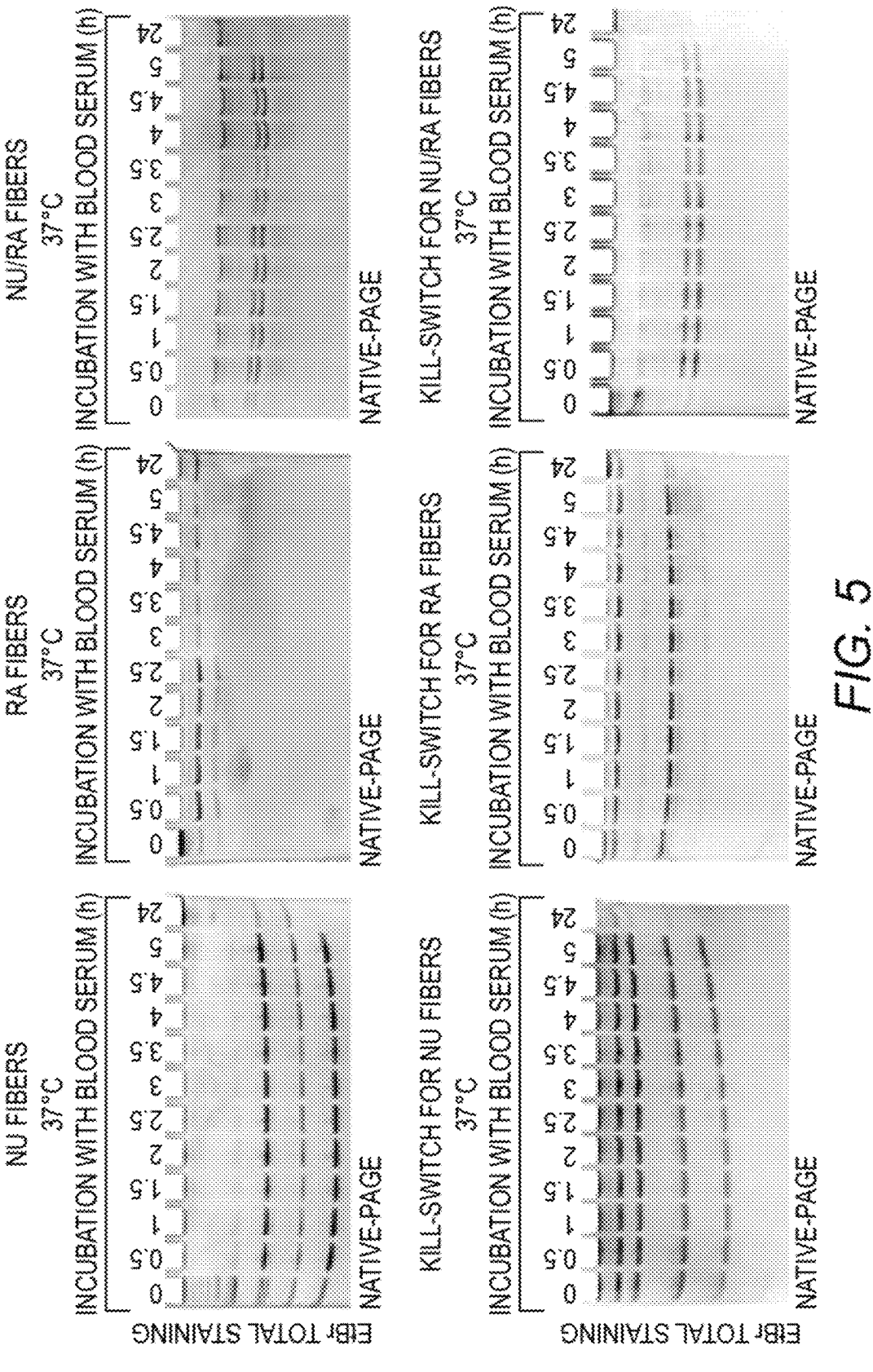

FIG. 5 shows examples of blood stability experiments carried out for anticoagulation fibers and corresponding kill-switches incubated for 24 hours.

Figure 6A:
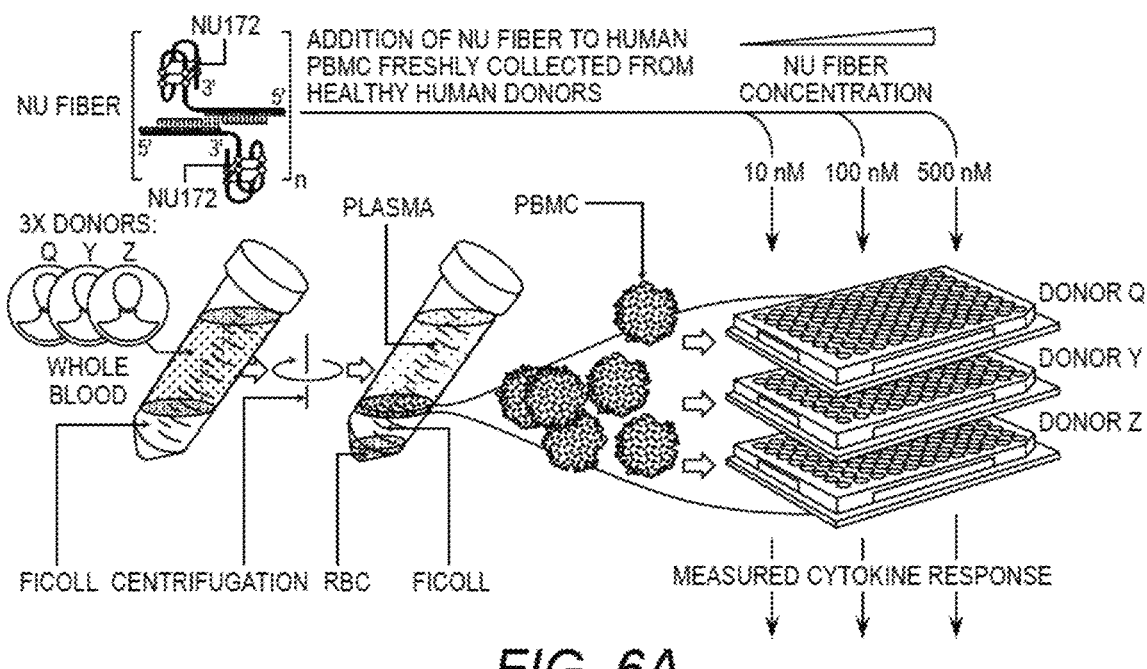
Figure 6B:
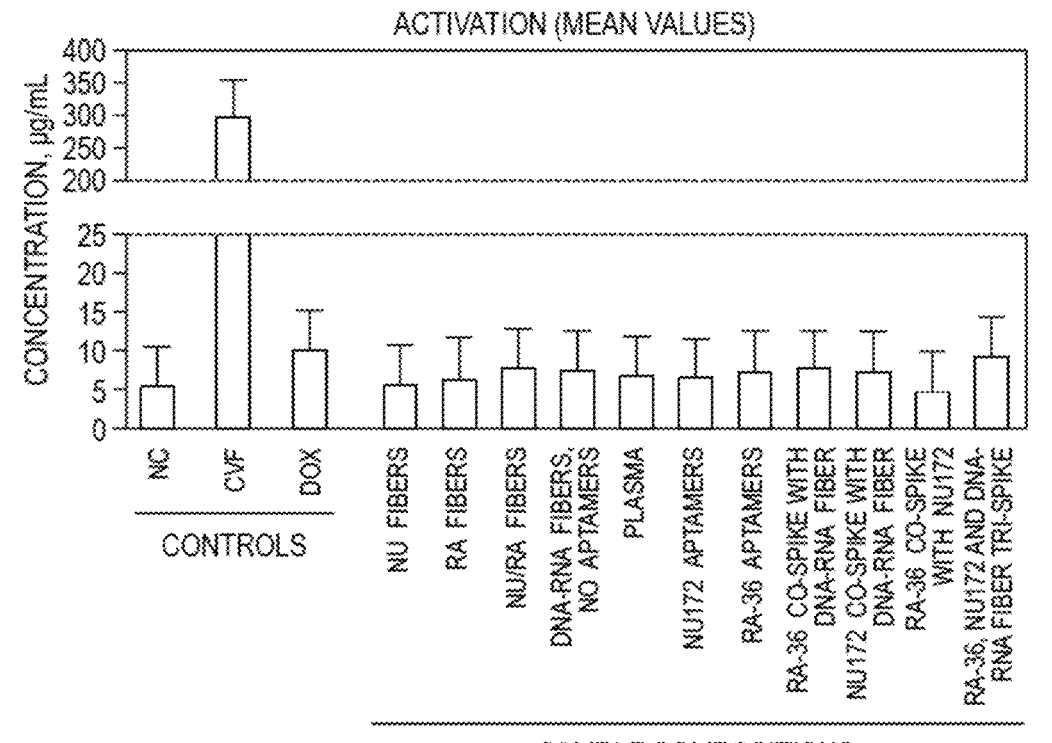
Figure 6C:
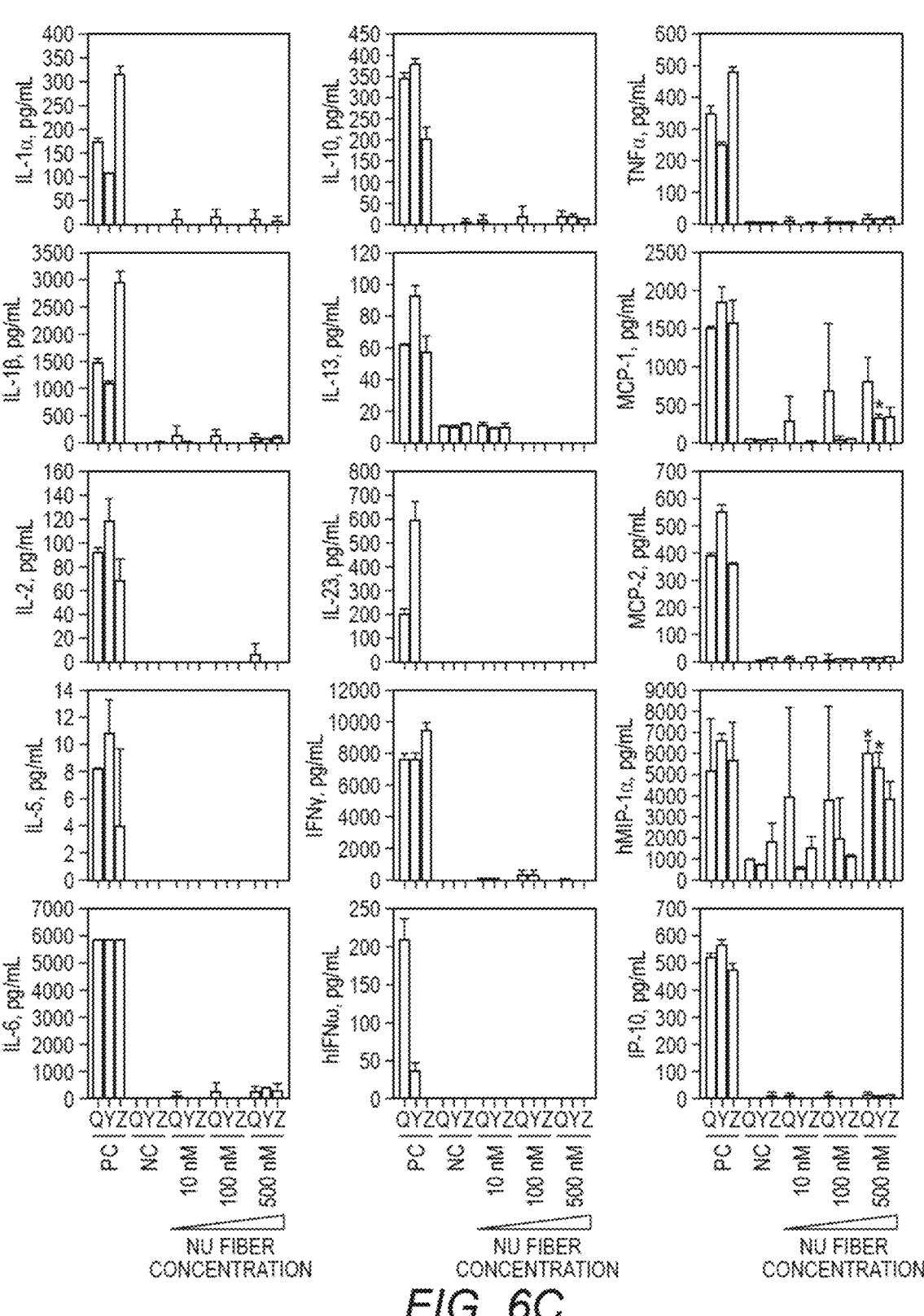

FIGS. 6A-6C show immunostimulation by anticoagulant fibers. (A) Schematic of the experimental flow. (B) Complement activation and (C) cytokines produced in response to anticoagulant fibers and aptamers assessed in human PBMCs freshly isolated from the blood of healthy donors. Data is shown as mean±SD, N=2 repeats for N=3 donors. Statistical significance of NU fibers compared to untreated cells (NC) is denoted by asterisk (p<0.05).

FIGS. 7A-7E show in vivo and ex vivo analysis of anticoagulant fibers' biodistribution and effect of kill-switches. (A) Schematic presentation of the experimental flow and motivation. (B) Animal (N=3/group) IVIS images at different timepoints post retro-orbital (RO) injections with fluorescently labeled aptamers, anticoagulant fibers, and kill-switches. (C) Liver and kidney lysates were further imaged to assess the estimated concentration of fibers. (D) The overtime fluorescence of the bladder of the treated mice was recorded and assessed as estimated concentrations. (E) The presence of kill-switch fibers increased the anti-thrombin fiber excretion rate.

Figure 8A:
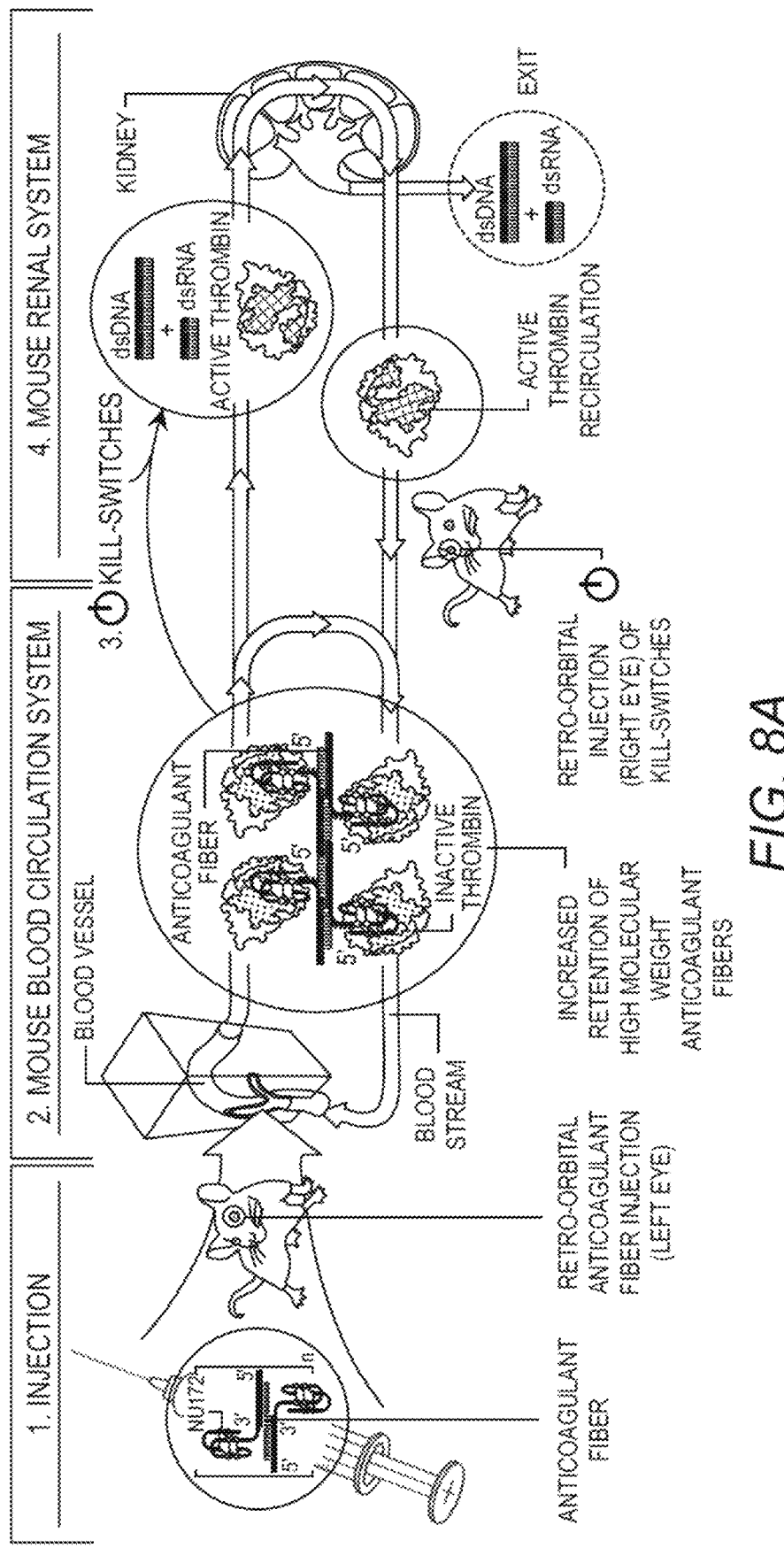
Figure 8B:
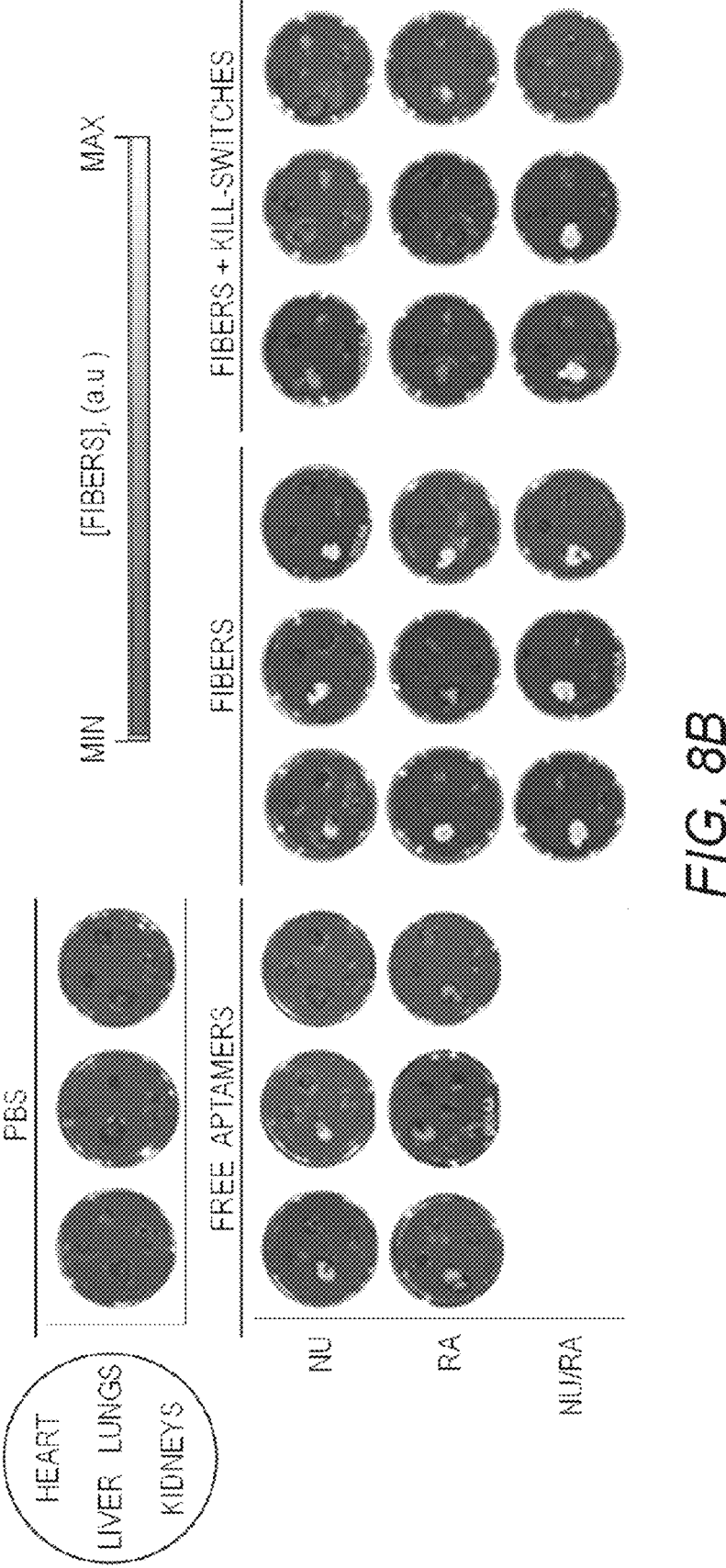

FIGS. 8A-8B show ex vivo organ imaging two hours post-injection. (A) Fluorescently labeled anti-thrombin fibers were administered to BALB/c mice via retro-orbital injection. After euthanasia, organs including the liver, kidneys, heart, and lungs were harvested and imaged. (B) Liver and kidney lysate were further imaged to assess the estimated concentration of anti-thrombin fibers and kill-switch fibers.

Figure 9A:
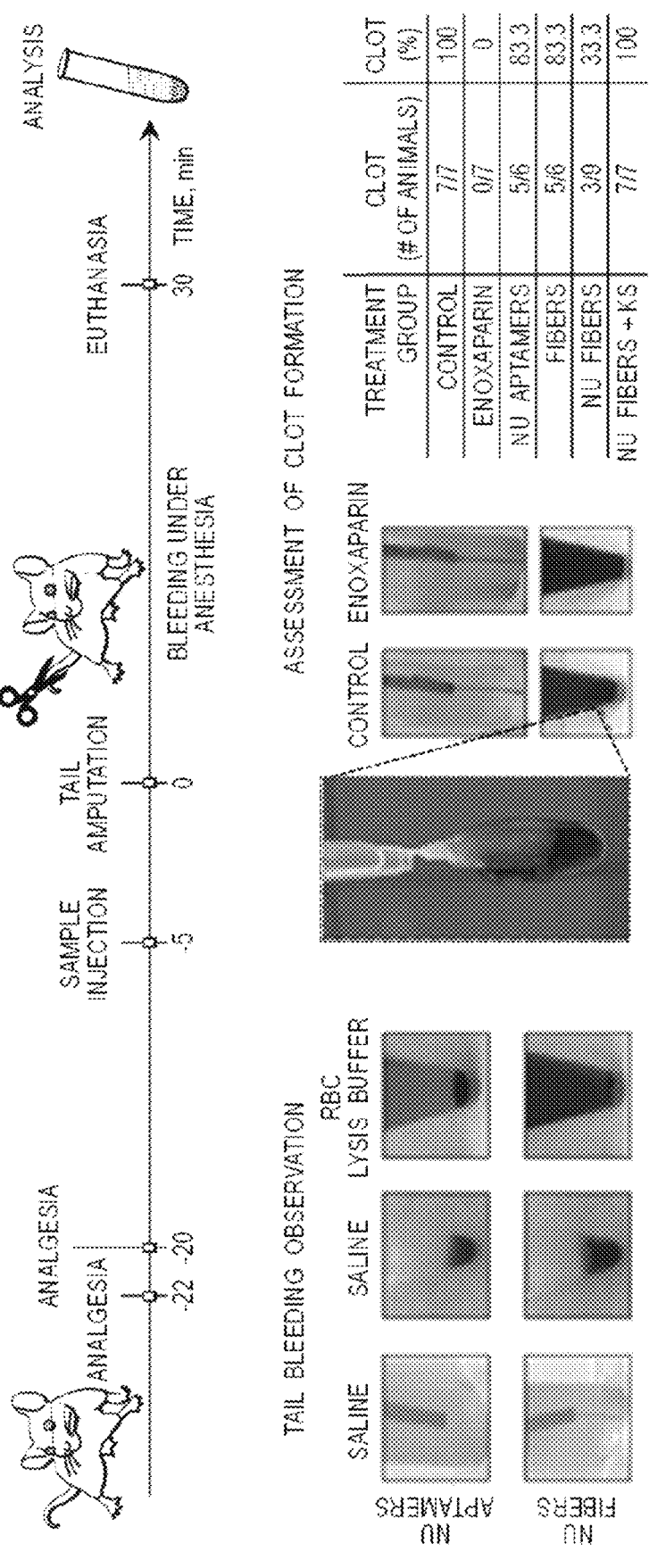
Figure 9B:
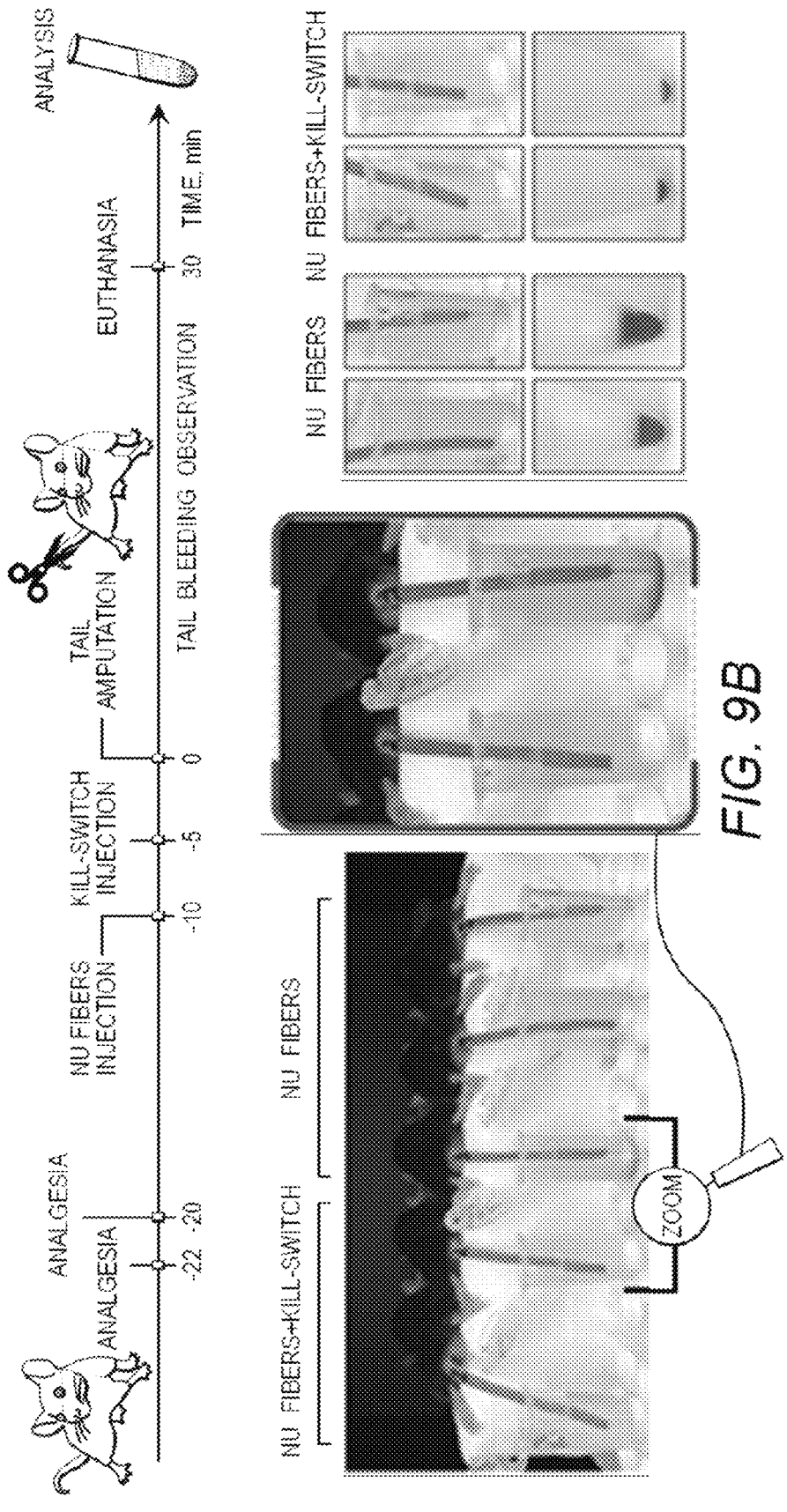
Figure 9C:
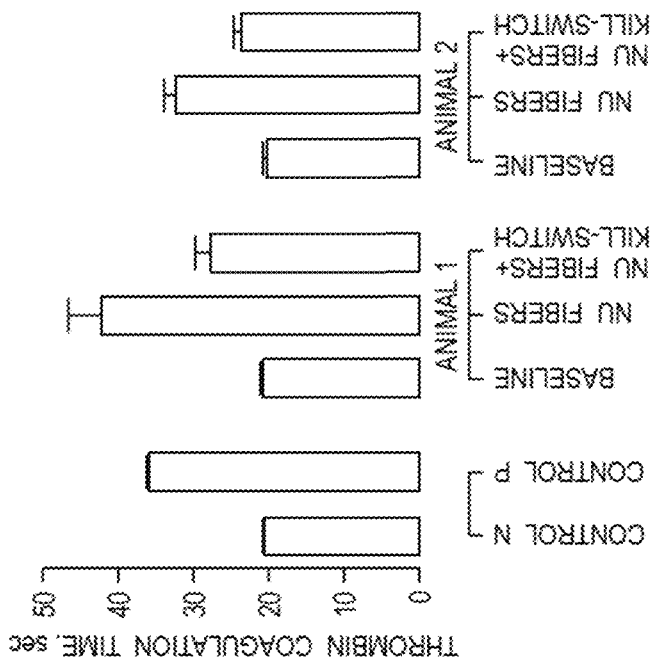
Figure 9C:
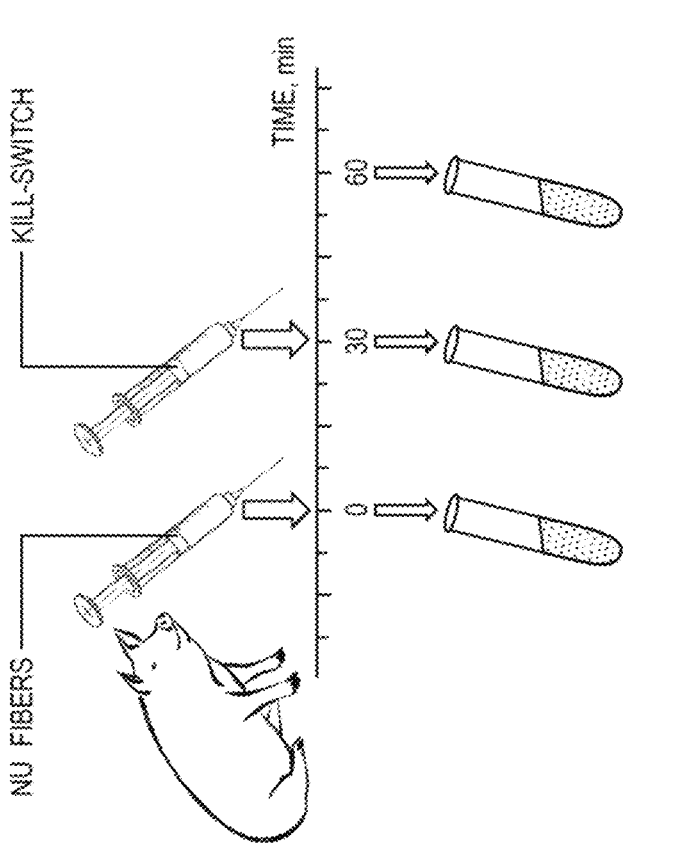

FIGS. 9A-9C show in vivo function of anticoagulant fibers and effect of kill-switches. (A) Blood clot formation in saline from freshly bled animals treated with various constructs. (B) Hemostasis analysis of anticoagulant fibers and kill-switch activity. Bleeding tails from animals treated with NU fiber or NU fiber and Kill-switch and the total blood volume collected in saline after 30 minutes of bleeding, showing, respectively, a decreased blood flow and volume collected from the animals treated both with NU fibers and Kill-switch. (C) Thrombin coagulation time measured in blood samples collected from Yorkshire swine treated with NU fibers and Kill switch.

FIGS. 10A-10D show in vivo function of anticoagulant fibers in a murine model of tail-bleeding. (A) Representative images of tail-bleeding from animals treated with control (assembly buffer), enoxaparin (5 mg/kg), NU aptamers, fibers (non-functional) or NU fibers, showing a distinct bleeding flow pattern. (B) Bleeding volume detection of animals treated with assembly buffer (control) or enoxaparin (5 mg/kg) (left) (p<0.05, T-student), or NU aptamer, fibers, NU fibers and NU fibers+Kill-switch (n.s., Kruskal-Wallis test with Dunn's post-hoc test). The shaded area represents the range out of limit of detection (minimal bleeding, less than 10 µl). (C) Bleeding score of animals treated with NU aptamers, fibers, NU fibers, and NU fibers+Kill-switch (n.s., Kruskal-Wallis test with Dunn's post-hoc test). (D) Re-bleeding occurrence detected in treated animals.

DETAILED DESCRIPTION OF THE INVENTION

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *Patent In User Manual*, 99-102 (November 1990) (U.S. Patent and Trademark Office).

Except as otherwise indicated, standard methods known to those skilled in the art may be used for the construction of recombinant parvovirus and AAV (rAAV) constructs, packaging vectors expressing the parvovirus Rep and/or Cap sequences, and transiently and stably transfected packaging cells. Such techniques are known to those skilled in the art. See, e.g., SAMBROOK et al., MOLECULAR CLONING: A LABORATORY MANUAL 4th Ed. (Cold Spring Harbor, NY, 2012); AUSUBEL et al., CURRENT PROTOCOLS IN MOLECULAR BIOLOGY (Green Publishing Associates, Inc. and John Wiley & Sons, Inc., New York).

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

The following terms are used in the description herein and the appended claims.

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to poly-nucleotides of the invention, refers to an increase or decrease in ability to bind an extracellular target of at least about 50% or more as compared to the binding ability of a polynucle-otide consisting of the recited sequence. The term "materially altered," as applied to polypeptides of the invention, refers to an increase or decrease in biological activity of at least about 50% or more as compared to the activity of a polypeptide consisting of the recited sequence.

A "polynucleotide" is a sequence of nucleotide bases, and may be RNA, DNA or DNA-RNA hybrid sequences (including both naturally occurring and non-naturally occurring nucleotides), and can be either single or double stranded DNA sequences.

An "aptamer," as used herein, refers to a single-stranded oligonucleotide that folds into a defined architecture and binds to a target.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J Mol. Evol.* 35:351 (1987); the method is similar to that described by Higgins & Sharp, *CABOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

As used herein, the term "modified," as applied to a polynucleotide or polypeptide sequence, refers to a sequence that differs from a wild-type sequence due to one or more deletions, additions, substitutions, or any combination thereof.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

This invention is based on the development of a user-friendly biomolecular platform based on modular RNA-DNA nanofibers comprising aptamers and programmed for reversible communication with extracellular targets and subsequent control of target activity via a "kill-switch" mechanism. The nanofibers contain multiple aptamers to substantially increase their molecular weight, prolong their blood stability, and increase their retention time in vivo. The reversibility of aptamer-based inhibition of an extracellular target by use of a kill-switch nanofiber provides the ability to regulate activity of the extracellular target as desired.

Thus, one aspect of the invention relates to a single strand DNA molecule comprising:
  a) a polynucleotide of about 40 to about 70 nucleotides in length, the polynucleotide comprising:

an RNA binding sequence of about 20 to about 30 nucleotides in length; and a toehold sequence of about 10 to about 20 nucleotides length linked to the 5' and 3' ends of the RNA binding sequence; and b) an aptamer linked to the 5' and/or 3' end of the polynucleotide;

wherein the aptamer(s) binds an extracellular target.

The polynucleotide may be about 40 to about 70 nucleotides in length, e.g., about 40 to about 50 nucleotides in length, e.g., about 40, 42, 44, 46, 48, 50, 52, 54, 56, 58, 60, 62, 64, 66, 68, or 70 nucleotides in length or any range therein.

The RNA binding sequence may be about 20 to about 30 nucleotides in length, e.g., about 25 to about 27 nucleotides in length, e.g., about 20, 21, 22, 23, 24, 25, 26, 27, 28, 29, or 30 nucleotides in length or any range therein. The nucleotide sequence of the RNA binding sequence may be any sequence as long as it is at least 80% complementary to a single stranded RNA molecule that forms part of a complex as described further below, e.g., at least 80% 85%, 90%, or 95% complementary.

The toehold sequence is present on both the 5' and 3' ends of the RNA binding sequence. The toehold sequence is about 10 to about 20 nucleotides length, e.g., about 12 to about 15 nucleotides in length, e.g., about 10, 11, 12, 13, 14, 15, 16, 17, 18, 19, or 20 nucleotides in length or any range therein. The nucleotide sequence of each toehold in the polynucleotide is the same and may be any sequence as long as it is at least 80% complementary to a toehold sequence of a second single strand DNA molecule that forms part of a nanofiber as described further below, e.g., at least 80% 85%, 90%, or 95% complementary.

The aptamer may be any aptamer known in the art or later developed that binds to an extracellular target. The extracellular target may be, e.g., a protein that circulates in the blood or other bodily fluids or is found on the cell surface. The aptamer may be a DNA aptamer, an RNA aptamer, or a DNA/RNA hybrid aptamer.

The aptamer, the polynucleotide, or both may contain one or more chemically modified nucleotides, e.g., to increase stability of the polynucleotide or the nanofiber. In some embodiments, the polynucleotide comprises, 1, 2, 3, 4, 5, 6, 7, 8, 9, 10, 12, 14, 16, 18, or 20 or more modified nucleotides. Examples of chemically modified nucleotides include, without limitation, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The aptamer or polynucleotide can further include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every one or every other one of the internucleotide bridging phosphate residues can be modified as described. In another non-limiting example, the aptamer or polynucleotide is a nucleotide sequence in which at least one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). In another example, one or more of the nucleotides may be a 2'-fluoro nucleotide, a 2-O-methyl nucleotide, or a locked nucleic acid nucleotide. For example, every one or every other one of the nucleotides can be modified as described. See also, Furdon et al., *Nucleic Acids Res.* 17:9193 (1989); Agrawal et al., *Proc. Natl. Acad. Sci. USA* 87:1401 (1990); Baker et al., *Nucleic Acids Res.* 18:3537 (1990); Sproat et al., *Nucleic Acids Res.* 17:3373 (1989); Walder and Walder, *Proc. Natd. Acad. Sci. USA* 85:5011 (1988); incorporated by reference herein in their entireties for their teaching of methods of making polynucleotide molecules, including those containing modified nucleotide bases).

The polynucleotide may contain one or two aptamers. In some embodiments, the aptamer is linked to the 5' end of the polynucleotide, e.g., 5' of the 5' toehold. In some embodiments, the aptamer is linked to the 3' end of the polynucleotide, e.g., 3' of the 3' toehold. In some embodiments, the aptamer is linked to the 5' end of the polynucleotide and the 3' end of the polynucleotide and the aptamers are the same. In some embodiments, the aptamer is linked to the 5' end of the polynucleotide and the 3' end of the polynucleotide and the aptamers are different. The aptamers may be different aptamers that bind to the same extracellular target, e.g., at different location on the extracellular target. The aptamers may be different aptamers that bind to different extracellular targets.

Numerous aptamers to extracellular targets are known in the art. Examples of known aptamers included, without limitation, the aptamers listed in Table 1. In some embodiments, the aptamer binds to thrombin and inhibits thrombin activity. Examples of thrombin aptamers include, without limitation, NU172, RA-36, ARC 183, HD1, HD22, TBA, Toggle-25t, TBA15/G15D, TBA29, 5'-thiol modified thrombin-binding aptamer, Anti-Thrombin Aptamer with Caged Thymidine Nucleobases, Modified thrombin binding aptamer (mTBA), Aptamer number 5, and 31-TBA, as listed in Table 1.

TABLE 1

| Target | Aptamer | Reference |
|---|---|---|
| α-synuclein | M5-15 | U.S. Pat. No. 9,238,816 B2 |
| Acetylcholine receptor (AChR) | Class I and Class II AChR aptamer | Ulrich et al., Proc. Natl. Acad.Sci. USA 95(24): 14051 (1998) |
| AFP | AFT aptamer | Lee et al., Biochem. Biophys. Res. Commun. 417(1):521 (2012) |

TABLE 1-continued

| Target | Aptamer | Reference |
|---|---|---|
| Amyloid beta-peptide A4 (1-40) | RNA aptamer | Ylera, Biochem. Biophys. Res. Commun. 290(5): 1583 (2002) |
| Beta-Secretase BACE1 (Bl-CT) | RNAaptTH14 | Rentmeister et al., RNA 12(9): 1650 (2006) |
| C5a | AON-D21 I-aptamer | Zhang et al., Molecules 24(5):941 (2019) |
| CCL2 | NOX-E36 | Maasch et al., Nucleic Acids Symp. Ser. (Oxf.) 52:61 (2008) |
| CD44/EpCAM | CD44-EpCAM aptamer | Song etal., Sensors 12(1):612 (2012) |
| CD8 | SEQ ID NOS: 1-7, 9-24, 31,32, 37, and 38 | US 2022/0072029 A1 |
| Coagulation factor Ixa | RB007 | Yu et al., Med. Chem. 52:5108 (2009) |
| Coagulation factor 1Xa | RB-006 | Cooper et al., J. Immune Based Ther. Vaccines 6:3 (2008) |
| Complement component 5 | ARC 1905 | Goebl et al., Toxicol. Pathol. 35:541 (2007) |
| Complement component 5 | ARC658 | U.S. Pat. No. 10,945,7544 B2 |
| Complement component 5 | ARC 186 | U.S. Pat. No. 10,9475,544 B2 |
| CTLA-4 | AptCTLA-4 | Song etal., Sensors 12(1):612 (2012) |
| CXCL12 | NOX-A12 | Sayyed et al., Diabetologia 52:2445 (2009) |
| EGFR | TuTu2231,KDI130 | Song etal., Sensors 12(1):612 (2012) |
| EGFR | Anti-EGFR aptamer (E07) | Li et al., PLoS ONE 6(6) Article ID e20299, (2011) |
| EpCAM | SEQ ID NOs. 230822-230899 | ES 2912033 T3 |
| EpCAM | SYL3 DNA aptamer | Song etal., Anal. Chem. 85(8):4141 (2013) |
| ErbB2 (avian erythroblastic leukemia viral oncogene homolog 2) | Peptide aptamer AII-7 | Kunz et al., Mol. Cancer Res. 4(12):983 (2006) |
| Erythrocyte membrane protein 1 (PfEMPI) | DBL1-specific RNA aptamer | Barfod et al., Parasitol. Res. 105(6): 1557 (2009) |
| E-selectin | ESTA | Song etal., Sensors 12(1):612 (2012) |
| Glycoprotein 120 (gpl20) | Anti-gp 120 aptamer chimera | Zhouetal., Mol. Ther 16(8): 1481 (2008) |
| Glycoprotein 120 (gpl20) | SEQ IDNO:1 | U.S. Pat. No. 10,041,071 B2 |
| Her 2 (human epidermal growth factor receptor 2) | DNA aptamer HB5 | Liu et al., J. Translational Med. 10(1): article 148 (2012) |
| HSP70 | Peptide aptamer A8 and A17 | Rerole etal., Cancer Res. 71(2):484 (2011) |
| HTT | MS3 | Riccardi et al., Int. J. Mol. Sci. 23(9):4804 (2022) |
| Human keratinocyte growth factor | 2'F RNA and 2'NH2 aptamer | Pagratis et al., Nature Biotechnol. 15(1):68 (1997) |
| K Ras-derived peptide | RNA aptamer G4 | Gilbert et al., Bioorg. Med. Chem. 5(6): 115 (1997) |
| L-selectin | RNA aptamer (10th rounds 4° C.) | O'Codnnell et al., Proc. Natl. Acad. Sci. USA 93(12):5883 (1996) |
| MDA | MDA aptamer MI | Brockstedt et al., Biochem. Biophys. Res. Commun. 313()4):1004 (2004) |
| Microvesicles (EpCam, CD9, PCSA, CD63, CD81,PSMA, B7H3, PSCA, ICAM, STEAP, KLK2, SSX2, SSX4, PBP, SPDEF, EGFR) | SEQ ID NOs. 231018-231031 | ES 2912033 T3 |
| MUCI peptide (Mucin-1) | MUCI DNA aptamer | Ferreira et al., Tumor Biol. 27(6):289 (2006) |
| NGF | SEQ ID NO: 1,2,3, 4,5,7 | KR 102021626 Bl |
| OmpC | DNA aptamer | Han, J. Microbiol. Biotechnol. 23(6):878 (2013) |
| PD-1 | SEQ ID NO: 1 | JP 6680760 B2 |
| PD-1 | MP7 | Song etal., Sensors 12(1):612 (2012) |
| PD-1 | aptPD-Ll | Lai et al., Mol. Ther. Nucleic Acids, 5(12):e397 |
| PSMA | SEQ ID NOs. 230932-230935 | ES 2912033 T3 |
| REV | RNA aptamer | Xu et al., Proc. Natl. Acad. Sci. USA 93(15):7475 (1996) |
| Tenascin-C | ITAI | Hicke et al., J. Nuclear Med. 47(4):668 (2006) |
| TGF type III receptor | RNA aptamer | Ohuchi met al., Biochimie 88(7):897 (2006) |
| Thrombin | TBA | Avino et al., Curr. Pharm. Design, 18(14):2036 (2012) |
| Thrombin | NU172 | Sheehan et al., Blood 92:1617 (1998) |
| Thrombin | Toggle-25t | White et al., Mol. Ther. 4(6):567 (2001) |

TABLE 1-continued

| Target | Aptamer | Reference |
|---|---|---|
| Thrombin | TBA15/G15D | Bock et al., Nature 355(6360):564 (1992) |
| Thrombin | TBA29 | Tasset et al., J. Mol. Biol. 272(5):688 (1997) |
| Thrombin | 5'-thiol modified thrombin-binding aptamer | Cho et al., BMB Reports 41(2): 126 (2008) |
| Thrombin | Anti-Thrombin Aptamer with Caged Thymidine Nucleobases | Heckel et al., J. Am. Chem. Soc. 127(3):822 (2005) |
| Thrombin | Modified thrombin binding aptamer (mTBA) | Pagano et al., Biophys. J. 94(2):562 (2008) |
| Thrombin | Aptamer number 5 | Hianik et al., Bioelectrochemistry 70(1): 127 (2007) |
| Thrombin | RA36 | Savchik et al., Bull. Exp. Biol. Med. 156(1):44 (2013) |
| Thrombin | ARC 183 | Nimjee etal., RNA 15(12):2105 (2009) |
| Thrombin | HD1 | Zavyalova et al., Nucleic Ccid Therapeutics, 26(5):299 (2016) |
| Thrombin | 31-TBA | Zavyalova et al., Nucleic Ccid Therapeutics, 26(5):299 (2016) |
| Thrombin | HD22 | Yoshitomi et al., Res. Practice Thrombosis Haemostasis 5(5):e 12503 (2021) |
| V3 loop of gp120, HIV-1RT | RNA aptamer S66A-C6, RNA aptamer S69A-C15 | Gronewold et al., J. Proteome Res. 8(7):3568 (2009) |
| VEGF-165 | Pegaptanib sodium | Chakravarthy et al., Ophthalmology 113:el (2006) |
| VEGF-165 | Macugen | Gragoudas et al., N. Engl. J. Med. 351:2805 (2004) |
| VEGF-165 | SL (2)-B (DNA) | Song etal., Sensors 12(1):612 (2012) |
| VEGF-165 | RNV66 (DNA) | Song etal., Sensors 12(1):612 (2012) |
| VEGF-165 | NX1838 | Lee et al., Joon-Hwa et al. Proc. Natl. Acad.Sci. USA 102(52): 18902 (2005) |
| Vimentin | NAS-24 | Song etal., Sensors 12(1):612 (2012) |
| β-NGF | SEQ ID NO: 3 | JP 6012591 B2 |

The polynucleotide may be constructed using chemical synthesis and/or enzymatic ligation reactions by procedures known in the art. For example, a polynucleotide may be chemically synthesized using naturally occurring nucleotides or various modified nucleotides designed to increase the biological stability of the polynucleotide or to increase the physical stability of the nanofiber formed from multimers of the polynucleotide.

Another aspect of the invention relates to a complex comprising the single strand DNA molecule of the invention, wherein the single strand DNA molecule is hybridized to a single strand RNA molecule of about 20 to about 30 nucleotides in length that is at least 80% complementary to the RNA binding sequence of the single strand DNA molecule.

The single strand RNA molecule may be about 20 to about 30 nucleotides in length, e.g., about 25 to about 27 nucleotides in length, e.g., about 20, 21, 22, 23, 24, 25, 26, 27, 28, 29, or 30 nucleotides in length or any range therein. The nucleotide sequence of the single strand RNA molecule may be any sequence as long as it is at least 80% complementary to the RNA binding sequence of the single strand DNA molecule, e.g., at least 80% 85%, 90%, or 95% complementary. The single strand RNA molecule may contain one or more chemically modified nucleotides as described above, e.g., 1, 2, 3, 4, 5, 6, 7, 8, 9, or 10 or more chemically modified nucleotides.

One of the keys to forming nanofibers from the polynucleotides of the invention is to have two polynucleotides with substantially complementary toeholds so that when the two polynucleotides are brought together under conditions suitable for hybridization, the toeholds interact, forming multimers and producing nanofibers.

Thus, a further aspect of the invention relates to a combination of a first single strand DNA molecule and a second single strand DNA molecule:

the first single strand DNA molecule comprising:
a) a polynucleotide of about 40 to about 70 nucleotides in length, the polynucleotide comprising:
an RNA binding sequence of about 20 to about 30 nucleotides in length; and
a toehold sequence of about 10 to about 20 nucleotides length linked to the 5' and 3' ends of the RNA binding sequence; and
b) an aptamer linked to the 5' and/or 3' end of the polynucleotide;
wherein the aptamer(s) binds an extracellular target;
the second single strand DNA molecule comprising:
a) a polynucleotide of about 40 to about 70 nucleotides in length, the polynucleotide comprising:
an RNA binding sequence of about 20 to about 30 nucleotides in length;
a toehold sequence of about 10 to about 20 nucleotides length linked to the 5' and 3' ends of the RNA binding sequence, wherein the toehold sequence of the second single strand DNA molecule is at least 80% complementary to the toe hold sequence of the first single strand DNA molecule; and
b) an aptamer linked to the 5' and/or 3' end of the polynucleotide;
wherein the aptamer(s) binds an extracellular target.

In some embodiments, the aptamer(s) of the first single strand DNA molecule and the aptamer(s) of the second single strand DNA molecule bind to the same extracellular target. In other embodiments, the aptamer(s) of the first single strand DNA molecule and the aptamer(s) of the second single strand DNA molecule bind to different extracellular targets.

The polynucleotide of each of the first and second single strand DNA molecule may be about 40 to about 70 nucleotides in length, e.g., about 40 to about 50 nucleotides in length, e.g., about 40, 42, 44, 46, 48, 50, 52, 54, 56, 58, 60, 62, 64, 66, 68, or 70 nucleotides in length or any range therein.

The RNA binding sequence of each of the first and second single strand DNA molecule may be about 20 to about 30 nucleotides in length, e.g., about 25 to about 27 nucleotides in length, e.g., about 20, 21, 22, 23, 24, 25, 26, 27, 28, 29, or 30 nucleotides in length or any range therein. The nucleotide sequence of the RNA binding sequence may be any sequence as long as it is at least 80% complementary to a single stranded RNA molecule that forms part of a complex as described further below, e.g., at least 80% 85%, 90%, or 95% complementary.

The toehold sequence of each of the first and second single strand DNA molecule is present on both the 5' and 3' ends of the RNA binding sequence. The toehold sequence of each of the first and second single strand DNA molecule is about 10 to about 20 nucleotides length, e.g., about 12 to about 15 nucleotides in length, e.g., about 10, 11, 12, 13, 14, 15, 16, 17, 18, 19, or 20 nucleotides in length or any range therein. The nucleotide sequence of each toehold in the polynucleotide is the same and may be any sequence as long as it is at least 80% complementary to a toehold sequence of a second single strand DNA molecule that forms part of a nanofiber as described further below, e.g., at least 80% 85%, 90%, or 95% complementary.

The aptamers may be any of the aptamers in any combination in any location on the first and second single stranded DNA molecule described above. The aptamers and/or polynucleotides may comprise one or more chemically modified nucleotides as described above.

In some embodiments, the aptamer of the first single strand DNA molecule is linked to the 5' end of the polynucleotide. In some embodiments, the aptamer of the first single strand DNA molecule is linked to the 3' end of the polynucleotide. In some embodiments, the aptamer of the first single strand DNA molecule is linked to the 5' end of the polynucleotide and the 3' end of the polynucleotide and the aptamers are the same. In some embodiments, the aptamer of the first single strand DNA molecule is linked to the 5' end of the polynucleotide and the 3' end of the polynucleotide and the aptamers are different.

In some embodiments, the aptamer of the second single strand DNA molecule is linked to the 5' end of the polynucleotide. In some embodiments, the aptamer of the second single strand DNA molecule is linked to the 3' end of the polynucleotide. In some embodiments, the aptamer of the second single strand DNA molecule is linked to the 5' end of the polynucleotide and the 3' end of the polynucleotide and the aptamers are the same. In some embodiments, the aptamer of the second single strand DNA molecule is linked to the 5' end of the polynucleotide and the 3' end of the polynucleotide and the aptamers are different.

In some embodiments, the aptamer(s) of the first single strand DNA molecule and the aptamer(s) of the second single strand DNA molecule are the same. In some embodiments, the aptamer(s) of the first single strand DNA molecule and the aptamer(s) of the second single strand DNA molecule are different. The different aptamers may bind to separate locations on the same extracellular target or may bind different extracellular targets.

An additional aspect of the invention relates to a complex comprising the combination of the invention, wherein the first single strand DNA molecule and the second single strand DNA molecule are hybridized to a single strand RNA molecule of about 20 to about 30 nucleotides in length that is at least 80% complementary to the RNA binding sequence of each of the single strand DNA molecules in the combination.

The single strand RNA molecule may be about 20 to about 30 nucleotides in length, e.g., about 25 to about 27 nucleotides in length, e.g., about 20, 21, 22, 23, 24, 25, 26, 27, 28, 29, or 30 nucleotides in length or any range therein. The nucleotide sequence of the single strand RNA molecule may be any sequence as long as it is at least 80% complementary to the RNA binding sequence of the first and second single strand DNA molecule, e.g., at least 80% 85%, 90%, or 95% complementary. The single strand RNA molecule may contain one or more chemically modified nucleotides as described above, e.g., 1, 2, 3, 4, 5, 6, 7, 8, 9, or 10 or more chemically modified nucleotides.

A further aspect of the invention relates to a nanofiber comprising multimers of the complex of the invention. A "nanofiber," as used herein, refers to a polynucleotide fiber on the nanometer scale (e.g., about 10 to about 10,000 nm in length) comprised of multimers of the complexes of the invention. The size and shape of the nanofiber will depend on the type of aptamers present in the first and second single strand DNA molecules and the number of complexes multimerized in the nanofiber. In some embodiments, the nanofiber may be about 10 to about 1000 nm in length or even longer or nay range therein, e.g., about 50 to about 1000 nm, e.g., about 100 to about 1000 nm. In some embodiments, the nanofiber may comprise about 10 to about 1000 aptamers or any range therein, e.g., about 50 to about 1000 aptamers, e.g., about 100 to about 1000 aptamers.

Another aspect of the invention relates to a method of making the nanofiber of the invention, comprising combining the combination of the invention with a single strand RNA molecule of about 20 to about 30 nucleotides in length that is at least 80% complementary to the RNA binding sequence of each of the single strand DNA molecules in the combination under conditions where the toehold sequences of the first and second single strand DNA molecules can hybridize to each other (e.g., a simple two step annealing process as described herein in the examples). To form the nanofiber, the first single strand DNA molecule, the second single strand DNA molecule, and the single strand RNA molecule may be combined in a molar ratio of about 1 to 1 to 2.

One of the advantages of the present invention is the ability to modulate the activity of an extracellular target by binding an aptamer nanofiber to the target to inhibit activity and then remove the aptamer nanofiber by contacting it with a kill-switch nanofiber to reverse the inhibition of the target. This allows inhibition of the target to be turned on and off as need. The kill-switch nanofiber, which contains a polynucleotide having a sequence that is the reverse complement of the polynucleotide in the single strand DNA molecule, causes the aptamer nanofiber to come part due to the favorable thermodynamics of formation of a double-stranded DNA molecule and a double stranded RNA molecule relative to the DNA-RNA hybrid complexes forming the aptamer nanofiber (see FIGS. 1A-1D). The small double-stranded DNA and RNA molecules are cleared and excreted rapidly.

Thus, one aspect of the invention relates to a kill-switch single strand DNA molecule, comprising a polynucleotide of about 40 to about 70 nucleotides in length, the polynucleotide comprising:

an RNA binding sequence of about 20 to about 30 nucleotides in length; and a toehold sequence of about 10 to about 20 nucleotides length linked to the 5' and 3' ends of the RNA binding sequence; and wherein the sequence of the polynucleotide is the reverse complement of the polynucleotide of the single strand DNA molecule of the invention.

The polynucleotide may be about 40 to about 70 nucleotides in length, e.g., about 40 to about 50 nucleotides in length, e.g., about 40, 42, 44, 46, 48, 50, 52, 54, 56, 58, 60, 62, 64, 66, 68, or 70 nucleotides in length or any range therein.

The RNA binding sequence may be about 20 to about 30 nucleotides in length, e.g., about 25 to about 27 nucleotides in length, e.g., about 20, 21, 22, 23, 24, 25, 26, 27, 28, 29, or 30 nucleotides in length or any range therein. The nucleotide sequence of the RNA binding sequence may be any sequence as long as it is at least 80% complementary to a single stranded RNA molecule that forms part of a complex as described further below, e.g., at least 80% 85%, 90%, or 95% complementary.

The toehold sequence is present on both the 5' and 3' ends of the RNA binding sequence. The toehold sequence is about 10 to about 20 nucleotides length, e.g., about 12 to about 15 nucleotides in length, e.g., about 10, 11, 12, 13, 14, 15, 16, 17, 18, 19, or 20 nucleotides in length or any range therein. The nucleotide sequence of each toehold in the polynucleotide is the same and may be any sequence as long as it is at least 80% complementary to a toehold sequence of a second single strand DNA molecule that forms part of a nanofiber as described further below, e.g., at least 80% 85%, 90%, or 95% complementary.

The kill-switch single strand DNA molecule may contain one or more chemically modified nucleotides as described above, e.g., 1, 2, 3, 4, 5, 6, 7, 8, 9, or 10 or more chemically modified nucleotides.

A further aspect of the invention relates to a complex comprising the kill-switch single strand DNA molecule of the invention, wherein the kill-switch single strand DNA molecule is hybridized to a single strand RNA molecule of about 20 to about 30 nucleotides in length that is at least 80% complementary to the RNA binding sequence of the single strand DNA molecule.

The single strand RNA molecule may be about 20 to about 30 nucleotides in length, e.g., about 25 to about 27 nucleotides in length, e.g., about 20, 21, 22, 23, 24, 25, 26, 27, 28, 29, or 30 nucleotides in length or any range therein. The nucleotide sequence of the single strand RNA molecule may be any sequence as long as it is at least 80% complementary to the RNA binding sequence of the kill-switch single strand DNA molecule, e.g., at least 80% 85%, 90%, or 95% complementary. The single strand RNA molecule may contain one or more chemically modified nucleotides as described above, e.g., 1, 2, 3, 4, 5, 6, 7, 8, 9, or 10 or more chemically modified nucleotides.

An additional aspect of the invention relates to a combination of a first kill-switch single strand DNA molecule and a second kill-switch single strand DNA molecule, the first kill-switch single strand DNA molecule comprising a polynucleotide of about 40 to about 70 nucleotides in length, the polynucleotide comprising:

an RNA binding sequence of about 20 to about 30 nucleotides in length; and a toehold sequence of about 10 to about 20 nucleotides length linked to the 5' and 3' ends of the RNA binding sequence; and the second kill-switch single strand DNA molecule comprising a polynucleotide of about 40 to about 70 nucleotides in length, the polynucleotide comprising:

an RNA binding sequence of about 20 to about 30 nucleotides in length; and a toehold sequence of about 10 to about 20 nucleotides length linked to the 5' and 3' ends of the RNA binding sequence, wherein the toehold sequence of the second kill-switch single strand DNA molecule is at least 80% complementary to the toe hold sequence of the first kill-switch single strand DNA molecule;

wherein the first kill-switch single strand DNA molecule comprises a sequence that is the reverse complement of the polynucleotide of the first single strand DNA molecule of the combination of the invention; and the second kill-switch single strand DNA molecule comprises a sequence that is the reverse complement of the polynucleotide of the second single strand DNA molecule of the combination of the invention.

The polynucleotide of each of the first and second kill-switch single strand DNA molecule may be about 40 to about 70 nucleotides in length, e.g., about 40 to about 50 nucleotides in length, e.g., about 40, 42, 44, 46, 48, 50, 52, 54, 56, 58, 60, 62, 64, 66, 68, or 70 nucleotides in length or any range therein.

The RNA binding sequence of each of the first and second kill-switch single strand DNA molecule may be about 20 to about 30 nucleotides in length, e.g., about 25 to about 27 nucleotides in length, e.g., about 20, 21, 22, 23, 24, 25, 26, 27, 28, 29, or 30 nucleotides in length or any range therein. The nucleotide sequence of the RNA binding sequence may be any sequence as long as it is at least 80% complementary to a single stranded RNA molecule that forms part of a complex as described further below, e.g., at least 80% 85%, 90%, or 95% complementary.

The toehold sequence of each of the first and second kill-switch single strand DNA molecule is present on both the 5' and 3' ends of the RNA binding sequence. The toehold sequence of each of the first and second single strand DNA molecule is about 10 to about 20 nucleotides length, e.g., about 12 to about 15 nucleotides in length, e.g., about 10, 11, 12, 13, 14, 15, 16, 17, 18, 19, or 20 nucleotides in length or any range therein. The nucleotide sequence of each toehold in the polynucleotide is the same and may be any sequence as long as it is at least 80% complementary to a toehold sequence of a second single strand DNA molecule that forms part of a kill-switch nanofiber as described further below, e.g., at least 80% 85%, 90%, or 95% complementary.

A further aspect of the invention relates to a complex comprising the combination of the invention, wherein each of the first and second kill-switch single strand DNA molecules is hybridized to a single strand RNA molecule of about 20 to about 30 nucleotides in length that is at least 80% complementary to the RNA binding sequence of each of the kill-switch single strand DNA molecules in the combination.

The single strand RNA molecule may be about 20 to about 30 nucleotides in length, e.g., about 25 to about 27 nucleotides in length, e.g., about 20, 21, 22, 23, 24, 25, 26, 27, 28, 29, or 30 nucleotides in length or any range therein. The nucleotide sequence of the single strand RNA molecule may be any sequence as long as it is at least 80% complementary to the RNA binding sequence of the first and second kill-switch single strand DNA molecule, e.g., at least 80% 85%, 90%, or 95% complementary. The single strand RNA molecule may contain one or more chemically modified nucleotides as described above, e.g., 1, 2, 3, 4, 5, 6, 7, 8, 9, or 10 or more chemically modified nucleotides.

Another aspect of the invention relates to a kill-switch nanofiber comprising multimers of the complex of the invention. The size of the kill-switch nanofiber will depend on the number of complexes multimerized in the nanofiber. In some embodiments, the kill-switch nanofiber may be about 10 to about 1000 nm in length or even longer or nay range therein, e.g., about 50 to about 1000 nm, e.g., about 100 to about 1000 nm.

An additional aspect of the invention relates to a method of making the kill-switch nanofiber of the invention, comprising combining the combination of the invention with a single strand RNA molecule of about 20 to about 30 nucleotides in length that is at least 80% complementary to the RNA binding sequence of each of the kill-switch single strand DNA molecules in the combination under conditions where the toehold sequences of the first and second kill-switch single strand DNA molecules can hybridize to each other. To form the kill-switch nanofiber, the first kill-switch single strand DNA molecule, the second kill-switch single strand DNA molecule, and the single strand RNA molecule may be combined in a molar ratio of about 1 to 1 to 2.

As described above, one of the advantages of the present invention is the ability to inhibit the activity of an extracellular target by contacting the target with an aptamer nanofiber of the invention, and then reversing the inhibition by contacting the inhibited target with the kill-switch nanofiber of the invention.

Thus, one aspect of the invention relates to a method of binding an aptamer to an extracellular target, comprising contacting the extracellular target with the aptamer nanofiber of the invention.

Another aspect of the invention relates to a method of reversing binding of an aptamer to an extracellular target, comprising contacting an extracellular target bound to the aptamer nanofiber of the invention with the kill-switch nanofiber of the invention.

A further aspect of the invention relates to a method of inhibiting the activity of an extracellular target, comprising contacting the extracellular target with the aptamer nanofiber of the invention, wherein the aptamer(s) in the nanofiber bind to and inhibit the activity of the extracellular target.

An additional aspect of the invention relates to a method of reversing inhibition of the activity of an extracellular target, comprising contacting the extracellular target bound to the aptamer nanofiber of the invention, wherein the aptamer(s) in the nanofiber bind to and inhibit the activity of the extracellular target, with the kill-switch nanofiber of the invention.

Another aspect of the invention relates to a method of regulating the activity of an extracellular target, comprising inhibiting activity by contacting the extracellular target with the aptamer nanofiber of the invention and then reversing the inhibition of activity by contacting the extracellular target bound to the aptamer nanofiber with the kill-switch nanofiber of the invention.

For each of the above methods, the extracellular target may be any target of interest. The extracellular target may be, e.g., a protein found in a bodily fluid (such as blood, serum, plasma, urine, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, lymphatic fluid, or cerebrospinal fluid) or is found on the surface of a cell, e.g., a cell surface protein or transmembrane protein. The extracellular target may be an in vitro target, e.g., an isolated protein or a protein on an isolated cell. The extracellular target may be an in vivo target, e.g., in a subject, e.g., a human subject. In some embodiments, the subject is one in need of the method, e.g., a patient in need of a treatment where inhibition of target activity would be beneficial or a subject where temporary inhibition of the target would be beneficial.

In some embodiments, the extracellular target is thrombin and modulation of thrombin activity (and therefore coagulation) is beneficial. One example is a subject undergoing surgery (e.g., coronary artery bypass surgery) where temporary inhibition of thrombin to prevent coagulation during surgery would lower the risk of clotting issues. Other examples include, without limitation, subjects undergoing kidney dialysis and other vascular, surgical, and coronary interventions.

Thus, one aspect of the invention relates to a method of inhibiting thrombin activity, comprising contacting thrombin with the aptamer nanofiber of the invention, wherein the aptamer(s) in the nanofiber bind to and inhibit thrombin activity.

Another aspect of the invention relates to a method of reversing inhibition of thrombin activity, comprising contacting thrombin bound to the aptamer nanofiber of the invention, wherein the aptamer(s) in the aptamer nanofiber bind to and inhibit thrombin activity, with the kill-switch nanofiber of the invention.

A further aspect of the invention relates to method of regulating thrombin activity, comprising inhibiting thrombin activity by contacting the thrombin with the aptamer nanofiber of the invention and then reversing the inhibition of thrombin activity by contacting thrombin bound to the aptamer nanofiber of the invention with the kill-switch nanofiber of the invention.

Nanofibers according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults.

In particular embodiments, the present invention provides a pharmaceutical composition comprising a nanofiber of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

A further aspect of the invention is a method of administering the nanofibers of the invention to subjects. Administration of the nanofibers according to the present invention to a human subject or an animal in need thereof can be by any means known in the art.

Optionally, the nanofibers is delivered in a treatment effective or prevention effective dose in a pharmaceutically acceptable carrier.

Dosages of the nanofibers to be administered to a subject depend upon the mode of administration, the disease or condition to be treated and/or prevented, the individual subject's condition, and the particular nanofibers, and the like, and can be determined in a routine manner.

In particular embodiments, more than one administration (e.g., two, three, four or more administrations) may be employed to achieve the desired level of target inhibition over a period of various intervals, e.g., hourly, daily, weekly, monthly, yearly, etc.

Exemplary modes of administration include systemic administration, e.g., intravenous administration. The vector may also be delivered to the CNS, e.g., by intrathecal, intracerebral, intraventricular, intranasal, intra-aural, intra-ocular, or peri-ocular delivery administration). In some embodiments, the vector may be delivered both systemically and to the CNS.

Delivery to a target tissue can also be achieved by delivering a depot comprising the nanofibers. In representative embodiments, a depot comprising the nanofibers is implanted into the tissue or the tissue can be contacted with a film or other matrix comprising the virus vector. Such implantable matrices or substrates are described in U.S. Pat. No. 7,201,898.

In particular embodiments, nanofibers according to the present invention are administered systematically, e.g., intravenously.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local manner, for example, in a depot or sustained-release formulation. Further, the virus vector and/or virus capsid can be delivered adhered to a surgically implantable matrix (e.g., as described in U.S. Patent Publication No. 2004-0013645).

Having described the present invention, the same will be explained in greater detail in the following examples, which are included herein for illustration purposes only, and which are not intended to be limiting to the invention.

Example 1

Materials and Methods

Sequences Used in this Project:
Anti-Thrombin Aptamer Sequences:

```
    NU172 Aptamer:
                                    (SEQ ID NO: 1)
    5'CGCCTAGGTTGGGTAGGGTGGTGGCG NU172 Aptamer labeled with Fluor750:
                                    (SEQ ID NO: 2)
    5'/5Alex750N/CGCCTAGGTTGGGTAGGGTGGTGGCG RA-36 Aptamer:
                                    (SEQ ID NO: 3)
    5'GGTTGGTGTGGTTGGTGGTTGGTGTGGTTGG RA-36 Aptamer labeled with Fluor750:
                                    (SEQ ID NO: 4)
    5'/5Alex750N/GGTTGGTGTGGTTGGTGGTTGGTGTGGTTGG
```

Anti-Thrombin Fibers:

To assemble anti-thrombin fibers, antithrombin aptamer DNA strand 1, antithrombin aptamer DNA strand 2, and RNA antisense were mixed in a 1 to 1 to 2 ratio.

```
NU 5' 3' + 5' 3': NU172 aptamer on both 5' and
3' ends of the repeating unit of fiber
Fiber antisense DNA strand 1
                                    (SEQ ID NO: 5)
5'CGCCTAGGTTGGGTAGGGTGGTGGCGTTTTCCCTTTAGGGAATGACCC

TGAAGTTCATCTGCACCACCGAGGGAAATCCCTTTTTCGCCTAGGTTGGG

TAGGGTGGTGGCG

Fiber antisense DNA strand 2
                                    (SEQ ID NO: 6)
5'CGCCTAGGTTGGGTAGGGTGGTGGCGTTTTTCCCTAAAGGGATGACCC

TGAAGTTCATCTGCACCACCGAAGGGATTTCCCTTTTCGCCTAGGTTGGG

TAGGGTGGTGGCG

RA 5' 3' + 5' 3': RA36 aptamer on both 5' and
3' ends of the repeating unit of fiber
Fiber antisense DNA strand 1
                                    (SEQ ID NO: 7)
5'GGTTGGTGTGGTTGGTGGTTGGTGTGGTTGGTTTTCCCTTTAGGGAAT

GACCCTGAAGTTCATCTGCACCACCGAGGGAAATCCCTTTTTGGTTGGTG

TGGTTGGTGGTTGGTGTGGTTGG

Fiber antisense DNA strand 2
                                    (SEQ ID NO: 8)
5'GGTTGGTGTGGTTGGTGGTTGGTGTGGTTGGTTTTTCCCTAAAGGGAT

GACCCTGAAGTTCATCTGCACCACCGAAGGGATTTCCCTTTTGGTTGGTG

TGGTTGGTGGTTGGTGTGGTTGG

NU 3' + 3' (NU fiber): NU172 Aptamer on 3'
end of the repeating unit of fiber strand
1 and strand 2
Fiber antisense DNA strand 1
                                    (SEQ ID NO: 9)
5'TCCCTTTAGGGAATGACCCTGAAGTTCATCTGCACCACCGAGGGAAAT

CCCTTTTTCGCCTAGGTTGGGTAGGGTGGTGGCG

Fiber antisense DNA strand 2
                                    (SEQ ID NO: 10)
5'TTCCCTAAAGGGATGACCCTGAAGTTCATCTGCACCACCGAAGGGATT

TCCCTTTTCGCCTAGGTTGGGTAGGGTGGTGGCG

NU 5' + 3': NU172 Aptamer on 5' end of the
repeating unit of fiber strand 1 and 3' end
of the repeating unit of fiber 2
Fiber antisense DNA strand 1
                                    (SEQ ID NO: 11)
5'CGCCTAGGTTGGGTAGGGTGGTGGCGTTTTCCCTTTAGGGAATGACCC

TGAAGTTCATCTGCACCACCGAGGGAAATCCCTT

Fiber antisense DNA strand 2
                                    (SEQ ID NO: 12)
5'TTCCCTAAAGGGATGACCCTGAAGTTCATCTGCACCACCGAAGGGATT

TCCCTTTTCGCCTAGGTTGGGTAGGGTGGTGGCG

NU 3' + 5': NU172 Aptamer on 3' end of the
repeating unit of fiber strand 1 and 5' end
of the repeating unit of fiber 2
Fiber antisense DNA strand 1
                                    (SEQ ID NO: 13)
5'TCCCTTTAGGGAATGACCCTGAAGTTCATCTGCACCACCGAGGGAAAT

CCCTTTTTCGCCTAGGTTGGGTAGGGTGGTGGCG
```

-continued

Fiber antisense DNA strand 2

(SEQ ID NO: 14)

5'CGCCTAGGTTGGGTAGGGTGGTGGCGTTTTTCCCTAAAGGGATGACCC

TGAAGTTCATCTGCACCACCGAAGGGATTTCCCT

NU 5' + 5': NU172 Aptamer on 5' end of the
repeating unit of fiber strand 1 and 2
Fiber antisense DNA strand 1

(SEQ ID NO: 15)

5'CGCCTAGGTTGGGTAGGGTGGTGGCGTTTTTCCCTTTAGGGAATGACCC

TGAAGTTCATCTGCACCACCGAGGGAAATCCCTT

Fiber antisense DNA strand 2

(SEQ ID NO: 16)

5'CGCCTAGGTTGGGTAGGGTGGTGGCGTTTTTCCCTAAAGGGATGACCC

TGAAGTTCATCTGCACCACCGAAGGGATTTCCCT

RA 3' + 3': RA-36 Aptamer on 3' end of the
repeating unit of fiber strand 1 and 2
Fiber antisense DNA strand 1

(SEQ ID NO: 17)

5'TCCCTTTAGGGAATGACCCTGAAGTTCATCTGCACCACCGAGGGAAAT

CCCTTTTTGGTTGGTGTGGTTGGTGGTTGGTGTGGTTGG

Fiber antisense DNA strand 2

(SEQ ID NO: 18)

5'TTCCCTAAAGGGATGACCCTGAAGTTCATCTGCACCACCGAAGGGATT

TCCCTTTTGGTTGGTGTGGTTGGTGGTTGGTGTGGTTGG

RA 5' + 3': RA-36 Aptamer on 5' end of the
repeating unit of fiber strand 1 and 3' end
of the repeating unit of fiber strand 2
Fiber antisense DNA strand 1

(SEQ ID NO: 19)

5'GGTTGGTGTGGTTGGTGGTTGGTGTGGTTGGTTTTCCCTTTAGGGAAT

GACCCTGAAGTTCATCTGCACCACCGAGGGAAATCCCTT

Fiber antisense DNA strand 2

(SEQ ID NO: 20)

5'TTCCCTAAAGGGATGACCCTGAAGTTCATCTGCACCACCGAAGGGATT

TCCCTTTTGGTTGGTGTGGTTGGTGGTTGGTGTGGTTGG

RA 3' + 5' (RA fiber): RA-36 aptamer on 3'
end of the repeating unit of fiber strand 1
and 5' end of the repeating unit of fiber
strand 2
Fiber antisense DNA strand 1

(SEQ ID NO: 21)

5'TCCCTTTAGGGAATGACCCTGAAGTTCATCTGCACCACCGAGGGAAAT

CCCTTTTTGGTTGGTGTGGTTGGTGGTTGGTGTGGTTGG

Fiber antisense DNA strand 2

(SEQ ID NO: 22)

5'GGTTGGTGTGGTTGGTGGTTGGTGTGGTTGGTTTTTCCCTAAAGGGAT

GACCCTGAAGTTCATCTGCACCACCGAAGGGATTTCCCT

RA 5' + 5': RA-36 aptamer on 5' end of the
repeating unit of fiber strand 1 and 2
Fiber antisense DNA strand 1

(SEQ ID NO: 23)

5'GGTTGGTGTGGTTGGTGGTTGGTGTGGTTGGTTTTCCCTTTAGGGAAT

GACCCTGAAGTTCATCTGCACCACCGAGGGAAATCCCTT

Fiber antisense DNA strand 2

(SEQ ID NO: 24)

5'GGTTGGTGTGGTTGGTGGTTGGTGTGGTTGGTTTTTCCCTAAAGGGAT

GACCCTGAAGTTCATCTGCACCACCGAAGGGATTTCCCT

-continued

NU 5' 3' + RA 5' 3' (NU/RA fiber): NU172
Aptamer on 5' and 3' ends of the repeating
unit of fiber strand 1 and RA36 aptamer on
5' and 3' ends of the repeating unit of
fiber strand 2
Fiber antisense DNA strand 1

(SEQ ID NO: 25)

5'CGCCTAGGTTGGGTAGGGTGGTGGCGTTTTCCCTTTAGGGAATGACCC

TGAAGTTCATCTGCACCACCGAGGGAAATCCCTTTTTCGCCTAGGTTGGG

TAGGGTGGTGGCG

Fiber antisense DNA strand 2

(SEQ ID NO: 26)

5'GGTTGGTGTGGTTGGTGGTTGGTGTGGTTGGTTTTTCCCTAAAGGGAT

GACCCTGAAGTTCATCTGCACCACCGAAGGGATTTCCCTTTTGGTTGGTG

TGGTTGGTGGTTGGTGTGGTTGG

Antisense RNA Sequences:

Antisense RNA (SEQ ID NO: 27)

5'CGGUGGUGCAGAUGAACUUCAGGGUCA

Antisense RNA labeled with Alexa 546

(SEQ ID NO: 28)

5'/5Alex546N/CGGUGGUGCAGAUGAACUUCAGGGUCA

Antisense RNA labeled with Alexa 750

(SEQ ID NO: 29)

5'/5Alex750N/CGGUGGUGCAGAUGAACUUCAGGGUCA

Antisense DNA (used for in vivo experiments in swine
model):

(SEQ ID NO: 30)

5'CGGTGGTGCAGATGAACTTCAGGGTCA

Kill-Switch of Anti-Thrombin Fibers:

To assemble kill-switch fiber, anti-fiber DNA strand 1,
anti-fiber DNA strand 2, and RNA sense was mixed in a 1
to 1 to 2 ratio.

Anti NU 3' + Anti NU 3' (anti-NU fiber): Anti
NU172 Aptamer on 3' end of repeating unit of
fiber strand 1 and fiber strand 2
Fiber sense DNA strand 1

(SEQ ID NO: 31)

5'CGCCACCACCCTACCCAACCTAGGCGAAAAAGGGATTTCCCTCGGTGG

TGCAGATGAACTTCAGGGTCATTCCCTAAAGGGA

Fiber sense DNA strand 2

(SEQ ID NO: 32)

5'CGCCACCACCCTACCCAACCTAGGCGAAAAGGGAAATCCCTTCGGTGG

TGCAGATGAACTTCAGGGTCATCCCTTTAGGGAA

Anti RA 3' + Anti RA 5' (anti-RA fiber): Anti
RA36 Aptamer on 3' end of repeating unit of
fiber strand 1 and 5' end of repeating unit
of fiber strand 2
Fiber sense DNA strand 1

(SEQ ID NO: 33)

5'CCAACCACACCAACCACCAACCACACCAACCAAAAAGGGATTTCCCTC

GGTGGTGCAGATGAACTTCAGGGTCATTCCCTAAAGGGA

Fiber sense DNA strand 2

(SEQ ID NO: 34)

5'AGGGAAATCCCTTCGGTGGTGCAGATGAACTTCAGGGTCATCCCTTTA

GGGAAAAACCAACCACACCAACCACCAACCACACCAACC

-continued

```
Anti NU 5' 3' + Anti RA 5'3' (anti-NU/RA
fiber): Anti NU172 Aptamer on 5' and 3'
ends of repeating unit of fiber strand 1
and RA-36 aptamer on 5' and 3' ends of
repeating unit of fiber strand 2:
Fiber sense DNA strand 1
                             (SEQ ID NO: 35)
5'CGCCACCACCCTACCCAACCTAGGCGAAAAAGGGATTTCCCTCGGTGG

TGCAGATGAACTTCAGGGTCATTCCCTAAAGGGAAAACGCCACCACCCTA

CCCAACCTAGGCG

Fiber sense DNA strand 2
                             (SEQ ID NO: 36)
5'CCAACCACACCAACCACCAACCACACCAACCAAAAGGGAAATCCCTTC

GGTGGTGCAGATGAACTTCAGGGTCATCCCTTTAGGGAAAAACCAACCAC

ACCAACCACCAACCACACCAACC
```

Sense RNAs:

```
Sense RNA
                             (SEQ ID NO: 37)
5'ACCCUGAAGUUCAUCUGCACCACCG Sense RNA labeled with Alexa 488
                             (SEQ ID NO: 38)
5'/5Alex488N/ACCCUGAAGUUCAUCUGCACCACCG
```

Sense DNA (used for in vivo experiments in swine model):

```
                             (SEQ ID NO: 39)
5'ACCCTGAAGTTCATCTGCACCACCG
```

Assembly of Anticoagulant Aptamer Fibers and Kill-Switches and their Analysis by Native-PAGE.

All individual oligos were purchased from Integrated DNA Technologies, Inc. The sequences of NU172 and RA-36 DNA aptamers are published [1, 2] and the DNA oligos from RNA-DNA fiber designs [3] were extended with aptamer sequences at either one or both ends of DNAs. Kill-switches were designed as reverse complements of corresponding anticoagulant fibers. All constructs were assembled by combining individual monomers at equimolar concentrations in hybridization buffer (89 mM Tris, 80 mM Boric Acid (pH 8.2), 2 mM magnesium chloride, 2 mM potassium chloride) and heating to 95° C. for 5 minutes followed by further incubation at room temperature for 20 minutes. Successful assemblies and their reassociations were analyzed at 4° C. on 8% non-denaturing native poly-acrylamide (19:1) gel electrophoresis (native-PAGE) run for 30 minutes at 300 V in hybridization buffer. A Bio-Rad ChemiDoc MP Imager was used to visualize gels stained with ethidium bromide (0.5 µg/mL) or by using the fluorescence of Alexa 546-labeled RNAs. All assemblies for immunological and in vivo studies were further tested for the presence of bacterial endotoxins by a kinetic turbidity limulus amoebocyte lysate (LAL) assay as discussed in our previous work [4].

Blood Stability of Anticoagulant Aptamer Fibers and Kill-Switches.

Freshly drawn human blood serum (after coagulation, blood was spun down and supernatant was collected) was aliquoted and frozen at −80° C. Anticoagulant fibers and the kill-switches (all at 1 µM final) were mixed with 10% human blood serum at 37° C., aliquoted (2 µL) at each time point, mixed with 2 µL native-PAGE loading buffer (50% glycerol, 0.25% bromophenol blue, 0.25% xylene cyanol, 89 mM Tris, 80 mM Boric Acid (pH 8.3), 2 mM magnesium chloride) and placed on dry ice. All samples were loaded in reverse time order and analyzed by 8% native-PAGE at 4° C. Bands of treated samples were visualized with a Bio-Rad ChemiDoc MP System, analyzed using Image Lab™ Software, and compared to bands of corresponding untreated constructs to determine relative degradation. Ethidium bromide total staining was used to assist visualization.

Kinetics of Reassociation of Anticoagulant Aptamer Fibers and Kill-Switches.

To determine kinetics, Alexa 546-labeled antithrombin aptamer fibers were mixed with equimolar antidotes and aliquoted at set time points as 2 µL added to 2 µL native-PAGE loading buffer. The aliquots were placed on dry ice, loaded in reverse time order, and analyzed by 8% native-PAGE at 4° C. Bands of treated samples were visualized with a Bio-Rad ChemiDoc MP System, analyzed using Image Lab™ Software, and compared to bands of corresponding untreated nanoparticles to determine relative degradation. Imaging with and without ethidium bromide staining was performed.

Atomic Force Microscopy (AFM) Imaging.

A freshly cleaved mica surface was modified with APS (1-(3-Aminopropyl) silatrane) according to established protocols [5, 6]. 5 µL of 1 µM sample solution was deposited onto APS-modified mica for 2 min. Unbound assemblies and excesses of salts were washed twice with 50 µL of DI water, and the mica surface was dried under a stream of argon gas. AFM imaging was performed on a MultiMode AFM Nanoscope IV system (Bruker Instruments, Santa Barbara, CA) in tapping mode. Images were recorded at 1.5 Hz scanning rate using a TESPA-300 probe from Bruker with a resonance frequency of 320 kHz and spring constant ~40 N/m. Images were processed by the FemtoScan Online software package (Advanced Technologies Center, Moscow, Russia).

In Silico Analysis of Anticoagulant Aptamer Fibers.

The 3D structure of NU172 was downloaded from Protein Data Bank [7] (PDB ID: 6GN7). The 3D structure of RA-36 was modeled using iFoldRNA [8, 9] by imposing constraints to form the G-quadruplex structure. The 3D structure of NU fiber, RA fiber and NU/RA fiber were modeled using iFoldRNA by imposing constraints [10] to form the specific secondary structures. MD simulations were performed using Discrete Molecular Dynamics (DMD). Discrete step function potentials are used in DMD to define the secondary structure and the G-quadruplex structure of the fibers. The DMD simulations were performed using the Medusa force field$^2$. 500,000 DMD time steps (~50 ps for each step) were performed for each simulation. The RMSF was calculated using MDAnalysis [11].

Prothrombin Time, Activated Partial Thromboplastin Time, and Thrombin Time Assessment.

Blood was obtained under NCI-at-Frederick Protocol OH9-C-N046 and FMUSP Protocol NP 1378/18. The blood was collected from at least three up to 21 healthy donors and anti-coagulated with sodium citrate. All the donors agreed with the use of their samples in this research and signed a respective informed consent. A plasma pool was prepared by spinning down the blood in a centrifuge for 10 min at 2500 g and was used within 8 h after collection. 50 µL of aptamer, fiber, anticoagulant fibers, or fibers with kill-switches with concentration of 5 µM were added to 450 µL of human plasma in a 1.5 mL Eppendorf tube. Each tube was incubated at 37° C. for 30 mins. Respective reagents were added to induce the coagulation cascade according to manufacturer protocols. A Diagnostica Stago STart 4 Hemostasis Analyzer was used to determine the PT, APTT, and TT. PT, APTT, and TT assays were conducted using clinical grade instruments and WHO-certified reagents commonly used in the clinic to identify deficiencies in blood coagulation and to monitor the efficacy of anti-thrombotic therapies.

Due to the high precision of coagulation instruments (coefficient of variation less than 5%) and the short (in seconds) nature of plasma coagulation, quantitative comparisons of plasma coagulation time between samples, even when statistically significant, does not provide a meaningful estimation of the treatment effect in plasma coagulation.

Complement Activation Determined by iC3b EIA Kit.

Complement activation was determined via cleavage of C3 factor by enzyme immunoassay (EIA) for presence of iC3b. The antibodies specific to iC3b were immobilized on 96-well plates and were obtained from MicroVue by Quidel. Blood was obtained under NCI-at-Frederick Protocol OH9-C-N046. The blood was collected from at least three healthy donors and anti-coagulated with EDTA. A plasma pool was prepared by spinning down the blood in a centrifuge for 10 min at 2500 g and was used within 8 h after collection. All samples were prepared at a concentration three times higher than the tested concentration (500 nM). Cobra venom factor (CVF) (Quidel Corporation, San Diego, USA) was used as a positive control. 50 μL (1.0-1.2 mg/ml) of CVF solution was used. PEGylated liposomal doxorubicin (DOXIL©), a prescription medication available from a licensed pharmacy, was also used as a positive control (20 mg of Doxorubicin HCl in 10 mL of vehicle). 50 μL of DOXIL© solution was used and 50 μL PBS was used as a negative control. In a 1.5 mL Eppendorf tube, 50 μL veronal buffer, 50 μL human plasma, 50 μL CVF, DOXIL©, PBS, and anticoagulant fibers or kill-switches were combined. Plasma samples were prepared in complement specimen diluent reagent (provided with each kit) according to the following dilution guide: iC3b—1:500 for CVF; 1:10 for negative control and other test samples. Two replicates of each sample were prepared, vortexed, centrifuged, and then incubated at 37° C. for 30 mins. 100 μL aliquots were used in EIA for each replicate. Manufacturer's instructions were followed to reconstitute complement standard, buffers, and controls, and determine plate loading volumes, incubation times, and plate washings. Optical density was read at 405 nm and a semi-log curve fit was used for assay result analysis.

Isolation of Primary Human Peripheral Blood Mononuclear Cells (PBMCs) and Immunorecognition of Anticoagulant-fibers.

Blood was obtained under NCI-at-Frederick Protocol OH9-C-N046. The blood was collected from at least three healthy donors and anticoagulated with Lithium-heparin. It was mixed 1:1 with PBS at room temperature and layered on top of Ficoll-Paque, then centrifuged at 900 g with low acceleration and no brake for 30 mins at room temperature. The mononuclear layer was collected, 3 times the volume of 1×HBSS was added, and the solution was centrifuged at 400 g for 10 mins at room temperature. After repeating the washing procedure, the mononuclear cells were resuspended in complete RPMI medium (RPMI 1640 with 10% FBS, 2 mM L-glutamine, 100 U/mL penicillin, and 100 μg/mL streptomycin). Live cells were enumerated by ViaStain AOPI and used in subsequent experiments. To stimulate PBMCs with antithrombin fibers for assessment of cytokine induction, cells were brought up to $1.25 \times 10^6$ cells/mL and seeded in 96-well U-bottomed plates with 160 μL volumes of 200 k cells per well. NU fiber was diluted in media to 0.05, 0.5, and 2.5 μM and 40 μL was added to each well for final concentrations of 10, 100, or 500 nM, respectively. As the positive controls, LPS (final 20 ng/mL, Invitrogen), ODN2216 (final 5 μg/mL), and PHA-M (final 10 μg/mL, Sigma) were added to PBMCs. As a negative control, blank media was added to PBMCs. All treatments were added to wells in technical duplicates for each donor. After 20 h incubation at 37° C., the plate was spun down at 700 g for 10 mins. 170 μL of supernatant was collected from each well and transferred into a new 96-well plate for analysis of cytokines by multiplexed ELISA (Q-Plex™ Multiplex Array from Quansys Biosciences) according to the manufacturer's instructions. Supernatants from the three positive controls were pooled 1:1:1. All wells were measured in duplicate. Plates were imaged on a Quansys Biosciences Q-View™ Imager Pro.

In Vivo Biodistribution Studies in Murine Model.

Eight-week-old male Balb/C mice were purchased from Jackson Laboratory. All animal experiments were carried out in compliance with institutional guidelines (Protocol #: 18-007). In all sample preparation, endotoxin-free HyClone Cell Culture-Grade Water was used to avoid endotoxin contamination. Alexa Fluor 750-labeled anticoagulant fibers were injected via R.O. with 100 μL volumes of 500 nM solutions. For the groups with kill-switches, one injection each in alternating eyes with 100 μL of 500 nM anticoagulant fibers and 100 μL of 500 nM kill-switches were performed, respectively. The amounts of fluorophore were kept equal throughout all treatments. Experimental and control groups were imaged at 15 mins, 30 mins, 1 h, and 2 h using IVIS. At the two-hour time point, animals were euthanized (isoflurane 1-3% followed by cervical dislocation), and the organs (lungs, heart, kidneys, and liver) were extracted and imaged for fluorescence. Portions of the liver and kidney were later weighted and lysed; their fluorescence amounts were determined by IVIS. Lab sand was purchased from Datesand and used in all cages for urine collection post-injection. Urine was collected from all animals and relative amounts of fluorescence were determined by IVIS. A standard curve was used to normalize the fluorophore concentration of the constructs.

In Vivo Blood Coagulation Studies in Murine Model.

All experimental procedures were approved by a local animal ethics committee (CEUA-FMUSP-protocol 1711/2021) in accordance with the code of practice for the care and use of animals for scientific purposes as described by the CONCEA (National Animal Research Council of Brazil). Male C57Bl/6 mice (20-28 g) at 8 weeks of age were used in this study. All mice were housed in a pathogen-free facility and kept on a 12 h light/dark cycle with ad libitum access to food and water. Mice were anesthetized using an anesthesia induction chamber with 2% isoflurane in 98% 02 at a flow rate of 1 L/min. Additionally, they received xylazine at 10 mg/kg (i.p.) 20 minutes before tail amputation. NANPs (100 μl) or controls (vehicle, enoxaparin sodium, 100 μl) were injected into mouse penile vein 5 minutes before tail amputation. Six groups of animals were treated as follows: vehicle (hybridization buffer), enoxaparin (5 mg/kg), NU aptamer (50 nmol/kg), fiber (50 nmol/kg), NU fiber (50 nmol/kg) and NU fiber+Kill-switch (50 nmol/kg each). At least 6 animals were included in each group. Anesthetized animals were positioned horizontally with the heads inside isoflurane/02 anesthesia individual compartments. The distal part of the mouse tail (diameter 2 mm) was amputated at a 900 angle and the tail was immediately submersed in a 6 mL conical tube containing 37° C. pre-warmed saline solution (PBS). Tail bleeding was visually observed over 30 minutes and the animals were euthanized right after in a $CO_2$ chamber for 5 minutes.

In Vivo Blood Coagulation Studies in Swine Model.

All experiments were approved by the Uniformed Services University's Institutional Animal Care and Use Committee. Two Yorkshire swine (Sus scrofa domesticus, 25 and 24 kg) were sedated with 500 mg ketamine intramuscular injection. Following isoflurane induction and intubation with a 6.5 Fr endotracheal tube, anesthesia was maintained with 1-2% isoflurane in 100% oxygen with a Drager Apollo workstation (Drager Medical, Lubeck Germany). Respiration was controlled by mechanical ventilation with 480 ml tidal volume and a respiratory rate of 12-15 breaths per minute, maintaining a baseline end-tidal $CO_2$ (ETCO2) of 35-42 mmHg. An ear vein was cannulated for fluid maintenance. An 18-gauge angiocath was placed percutaneously for invasive blood pressure measurement. The right external jugular vein was cannulated with a 9Fr introducer sheath, and a Schwan-Ganz catheter was placed in the pulmonary artery for continuous measurement of the pulmonary arterial pressure. The site port of the introducer sheath was used for blood sample collection and administration of the test substances. Systemic blood pressure, pulmonary arterial pressure, electrocardiogram (ECG), ETCO2, and core temperature were continuously recorded using a Powerlab data acquisition system (AdInstruments Inc., Colorado Springs, Colorado, USA). Blood samples were obtained at baseline and 30 minutes after each injection of test material. After instrumentation the animals were allowed to stabilize for 30 minutes. Following collection of baseline blood samples, representative anticoagulant fibers made of DNA oligos were injected into the central vein; the injected dose was 10 ml of ~170 µM solution per animal. Hemodynamic parameters were continuously monitored and recorded. Thirty (30) minutes after the injection, blood samples were collected and the procedure was repeated with the representative kill-switch fibers made of DNA oligos; the kill-switch fibers were injected into the central vein at a dose of 10 ml of ~170 µM solution per animal. Thirty (30) minutes after this injection, the blood was collected and coagulation time (TT) was assessed as described above.

Statistics.

Results of each assay are presented as mean±standard deviation (SD). Each experiment was performed at least three times (n≥3) and a one-way ANOVA followed by a t-test was carried out to determine significant differences using GraphPad Prism 9.0.0 for Windows. In all cases, differences were considered significant when $p<0.05$.

REFERENCES FOR EXAMPLE 1

1. Zavyalova, E., et al., Module-Activity Relationship of G-quadruplex Based DNA Aptamers for Human Thrombin. Current Medicinal Chemistry, 2013. 20(38): p. 4836-4843.
2. Zavyalova, E., et al., The Evaluation of Pharmacodynamics and Pharmacokinetics of Anti-thrombin DNA Aptamer RA-36. Frontiers in Pharmacology, 2017. 8.
3. Ke, W., et al., RNA-DNA fibers and polygons with controlled immunorecognition activate RNAi, FRET and transcriptional regulation of NF-kappaB in human cells. Nucleic Acids Res, 2019. 47(3): p. 1350-1361.
4. Dobrovolskaia, M. A. and K. A. Afonin, Use of human peripheral blood mononuclear cells to define immunological properties of nucleic acid nanoparticles. Nat Protoc, 2020. 15(11): p. 3678-3698.

5. Shlyakhtenko, L. S., et al., Silatrane-based surface chemistry for immobilization of DNA, protein-DNA complexes and other biological materials. Ultramicroscopy, 2003. 97(1-4): p. 279-87.
6. Shlyakhtenko, L. S., A. A. Gall, and Y. L. Lyubchenko, Mica functionalization for imaging of DNA and protein-DNA complexes with atomic force microscopy. Methods Mol Biol, 2013. 931: p. 295-312.
7. Berman, H. M., et al., The Protein Data Bank and the challenge of structural genomics. Nat Struct Biol, 2000. 7: p. 957-9.
8. Ding, F., et al., Ab initio RNA folding by discrete molecular dynamics: from structure prediction to folding mechanisms. RNA, 2008. 14(6): p. 1164-73.
9. Krokhotin, A., K. Houlihan, and N. V. Dokholyan, iFoldRNA v2:folding RNA with constraints. Bioinformatics, 2015. 31(17): p. 2891-3.
10. Wang, J., et al., Limits in accuracy and a strategy of RNA structure prediction using experimental information. Nucleic Acids Res, 2019. 47(11): p. 5563-5572.
11. Michaud-Agrawal, N., et al., MDAnalysis: a toolkit for the analysis of molecular dynamics simulations. J Comput Chem, 2011. 32(10): p. 2319-27.

Example 2

Aptamer Nanofibers

To improve the operation of current anticoagulants, the inventors developed a dynamic platform based on RNA-DNA fibers[33] rationally designed for the efficient and reversible control of blood coagulation. These robust nanoassemblies contain multiple thrombin-binding aptamers to substantially increase their molecular weight, prolong their blood stability, and increase their retention time in vivo. Another unique feature of this molecular system stems from its ability to be conditionally deactivated via a "kill-switch" mechanism that reverses its anticoagulant function and produces low molecular weight assemblies that undergo rapid renal excretion (FIGS. 1A-1D). With a minimal set of short, chemically synthesized oligos, we engineered 12 distinct DNA-RNA fibers were engineered that carry either NU172, or RA-36, or combinations thereof (so-called anticoagulant fibers) (FIG. 2). Effective inhibition of human plasma coagulation was demonstrated using the constructs and reversal of this effect through the introduction of kill-switches. To address potential demographic and inter-donor variability, all coagulation experiments were carried out with fresh blood samples from human donors in the United States (US) or in Brazil. To address safety concerns, immunological profiles and toxicities of the nanodevices were analyzed in human peripheral blood mononuclear cells (PBMCs) freshly collected from healthy human donors. The biodistribution, retention time, and anticoagulant function of fibers and kill switches were compared in murine and porcine models. Based on the results, it is concluded that the anticoagulant platform offers: i) simple design and assembly protocols; ii) excellent batch-to-batch consistency and shelf-life; iii) superior and prolonged anticoagulation time when compared to free aptamers; iv) extended (or prolonged) blood circulation time and stability in biological matrix (or blood); and v) a kill-switch mechanism which successfully controls anti-coagulation, restores thrombin activity and promotes the excretion of functionally inactive metabolites. Design, Assembly, and Characterization of Anticoagulant Fibers.

Figures 1A, 1B, 1C:
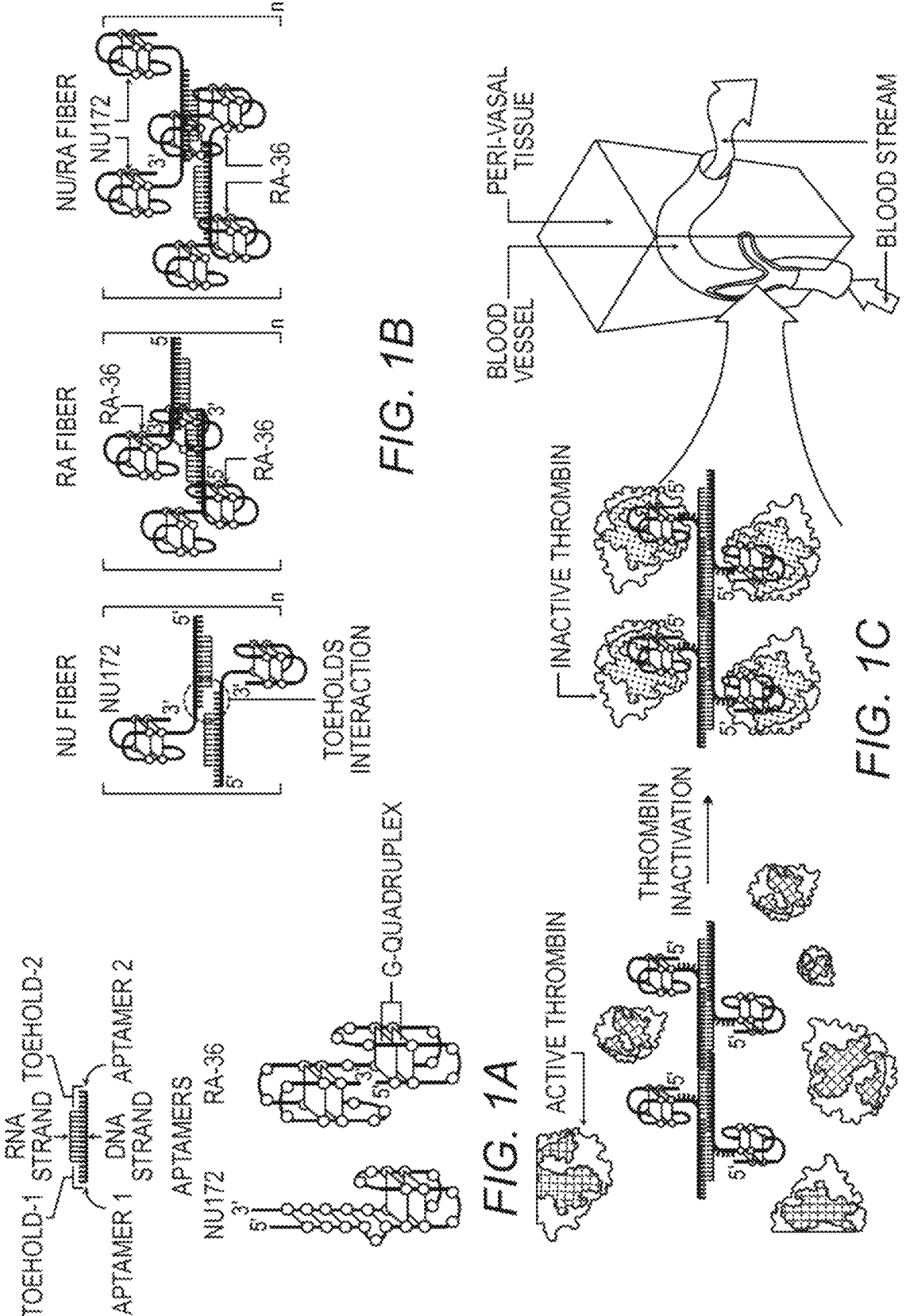
FIGS. 1A-1D show the mechanism of action for anticoagulant fibers and kill-switches. (A, B) The design of anticoagulant fibers carrying NU172 and RA-36 aptamers with three possible aptamer locations within the fibers
Figure 1D:
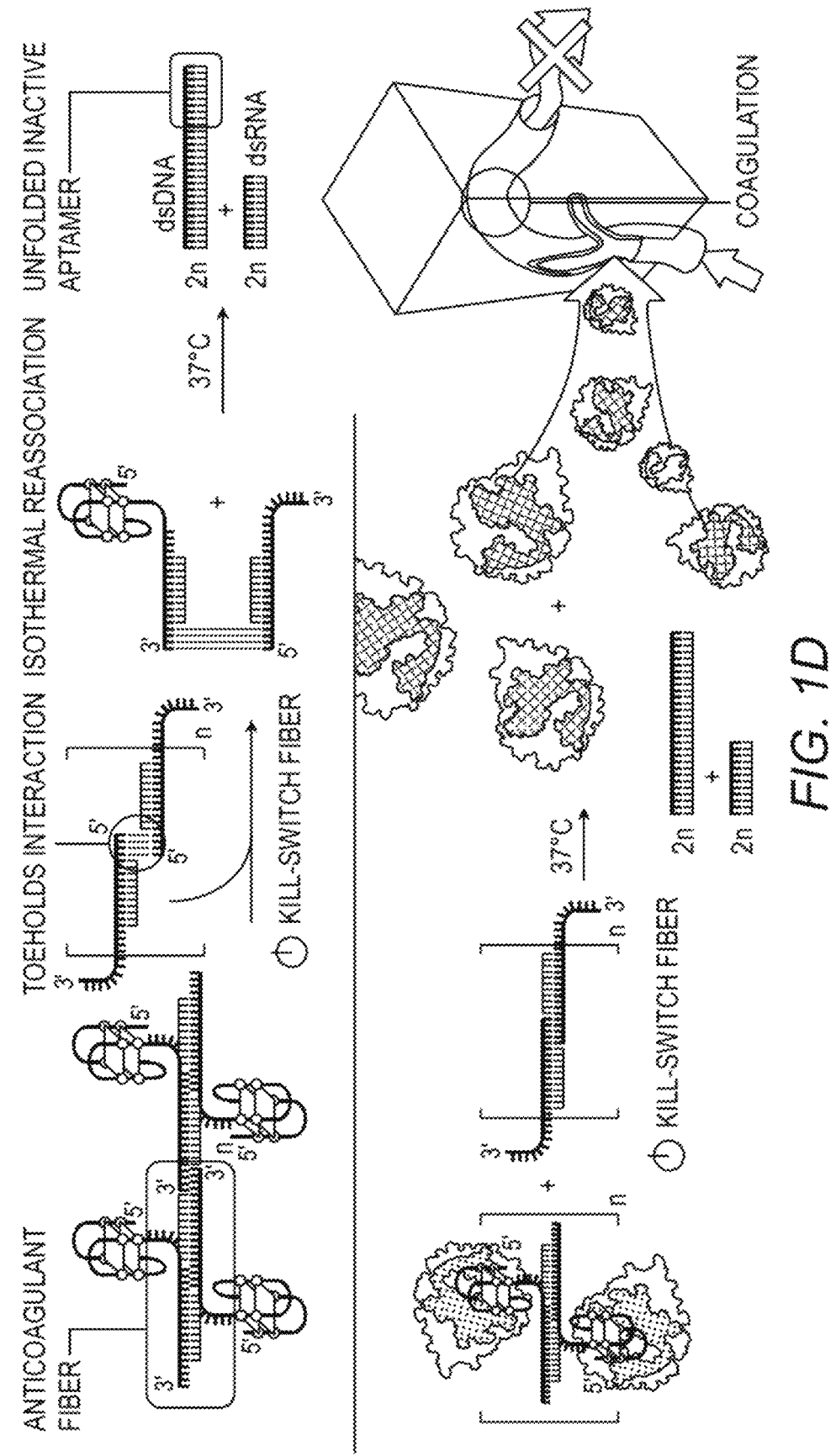

An RNA-DNA hybrid system with the ability to conditionally activate various functions in cancer cells was previously reported (31). Here, the potential of this reconfigurable technology for the extracellular regulation of blood coagulation was explored. The effectiveness of this approach relies on thrombin inactivation as well as prolonged aptamer retention time due to the substantial increase in the molecular weight of the nanoassemblies. The anticoagulant fibers were designed (FIGS. 1A-1B and 2) to carry multiple copies of anti-thrombin aptamers (RA-36 and/or NU172). Because of their small size, free aptamers are prone to fast renal clearance, and their programmable assembly into larger fibers is expected to enhance the circulation time in vivo (FIG. 1C). To exert greater control over thrombin activity, kill-switches were developed, which are fibers fully complementary to their anticoagulant counterparts (FIG. 1D), to undergo thermodynamically driven isothermal re-association and subsequently release inactive short duplexes to accelerate the clearance of the system. Three representative anticoagulant fibers, decorated with either NU172 (NU fibers), RA-36 (RA fibers), or both aptamers (NU/RA fibers), were chosen for experimental characterization in silico, in vitro, and in vivo. However, the anticoagulation activity was assessed for all 12 different fibers and compared to non-functionalized analogs and free aptamers (Table 2).

switches. Kinetic studies show that RA and NU/RA anticoagulant fibers need less than 30 minutes of incubation with kill-switches to complete the re-association, whereas NU anticoagulant fibers require a longer incubation time. The differences in the fibers' morphology and kinetics stem from the three-dimensional structures of aptamers which show the presence of two symmetric G-quadruplexes in RA-36 and one G-quadruplex in NU172 (FIGS. 3A and 3C). To gain further details, molecular dynamic simulations using DMD (discrete molecular dynamics) was employed and the RMSF (root mean square fluctuation) calculated. NU/RA anticoagulant fibers have higher RMSF (3.65 Å) than RA anticoagulant fibers (3.37 Å) and NU anticoagulant fibers (3.21 Å). High RMSF regions mainly consist of 5' and 3' ends of DNA strands, G-quadruplex regions, and single-stranded regions that connect G-quadruplex and duplex regions of DNA strands (FIG. 3B). The number of G-quadruplexes correlates with fiber flexibility and length. NU/RA anticoagulant fibers contain six G-quadruplex regions, RA anticoagulant fibers contain four G-quadruplex regions, and NU anticoagulant fibers contain two G-quadruplex regions. Thus, NU/RA anticoagulant fibers have greater flexibility and shorter length than RA anticoagulant fibers, while RA anticoagulant fibers are more flexible and shorter than NU anticoagulant fibers (all in agreement with AFM imaging). Due to their

TABLE 2

Coagulation test for antithrombin fibers.

| Sample | Sample description | APTT (34.1 s *) | PT (13.4 s *) | TT (21.0 s *) |
|---|---|---|---|---|
| NU 5' 3' + 5' 3' | Both DNA have NU172 on 5' & 3' | 92.3 ± 16.7 | 21.6 ± 15.5 | 56 ± 6.1 |
| NU 5' + 5' | NU172 on 5' of DNA1 and DNA2 | 86.5 ± 28.4 | 15.68 ± 2.1 | 56.8 ± 7.2 |
| NU 5' + 3' | NU172 on 5' of DNA1 and 3' of DNA2 | 94.3 ± 36.8 | 25.12 ± 17.1 | 511 ± 2.8 |
| NU 3' + 3' (NU fiber) | NU172 on 3' of DNA1 and 3' of DNA2 | 94.8 ± 37 | 23.14 ± 20.7 | 55.1 ± 11 |
| NU 3' + 5' | NU172 on 3' of DNA1 and 5' of DNA2 | 98 ± 31.4 | 20.04 ± 4.95 | >60 |
| RA 5' 3' + 5' 3' | Both DNA have RA36 on 5' & 3' ends | 84.96 ± 12.7 | 16.18 ± 2.4 | >60 |
| RA 5' + 5' | RA-36 on 5' of DNA1 and DNA2 | 83.54 ± 27.1 | 18.26 ± 3.5 | >60 |
| RA 5' + 3' | RA-36 on 5' of DNA1 and 3' of DNA2 | 72.5 ± 17.6 | 17.6 ± 2 | >60 |
| RA 3' + 3' | RA-36 on 3' of DNA1 and 3' of DNA2 | 74.54 ± 13.7 | 17.18 ± 4.5 | >60 |
| RA 3' + 5' (RA fiber) | RA-36 on 3' of DNA1 and 5' of DNA2 | 72.14 ± 23.6 | 16.6 ± 0.9 | >60 |
| S NU5'3' + RA5's 3'(NU/RA fiber) | NU172 and RA-36 on both ends of DNA1 & DNA2, respectively | 89.04 ± 18.8 | 16.42 ± 4.2 | >60 |
| RA 3' | RA-36 on 3' of the DNA1 and no aptamer on DNA2 | 75.5 ± 6.3 | 20.5 ± 5.5 | >60 |
| DNA-RNA fiber | DNA-RNA fiber, no aptamer | 36.68 ± 1.7 | 11.84 ± 0.7 | 15.8 ± 1.6 |
| plasma | plasma | 33.37 ± 2.7 | 10.76 ± 0.4 | 16.3 ± 0.8 |
| NU aptamer | NU172 aptamer | 37.98 ± 3.3 | 10.9 ± 0.5 | 15.3 ± 1.7 |
| RA aptamer | RA-36 aptamer | 41.5 ± 7.1 | 11.32 ± 0.9 | 20 ± 7.7 |
| RA aptamer + DNA-RNA fiber | Aptamer RA-36 co-spike with DNA-RNA fiber | 45.55 ± 1.5 | 12.25 ± 0.2 | 32.8 ± 9.3 |
| NU aptamer + DNA-RNA fiber | Aptamer NU172 co-spike with DNA-RNA fiber | 31.15 ± 9.6 | 10.9 ± 0.1 | 16.1 ± 0.4 |
| RA aptamer + NU aptamer | Aptamer RA-36 co-spike with Aptamer NU 172 | 41.35 ± 3.6 | 12.35 ± 0.1 | 31.2 ± 4.8 |
| RA aptamer + NU aptamer + DNA-RNA fiber | Aptamer RA-36, Aptamer NU172 and DNA-RNA fiber tri-spike | 52.4 ± 2.7 | 12.8 ± 0.1 | 51 ± 12.7 |

* Normal coagulation time of PT, APTT and TT are adapted from NCI method ITA-12.

Formation and re-association of anticoagulant fibers and kill-switches was visualized by AFM and confirmed by native-PAGE experiments (FIGS. 3A-3C and 4). The results confirm the efficient transformation of anticoagulant fibers into short duplexes upon their re-association with kill-high degree of flexibility, NU/RA anticoagulant fibers are most prone to disassociation (consistent with native-PAGE analysis).

The durability of anticoagulant fibers and kill-switches against nucleases was assessed in blood stability assays (FIG. 5) that show the detectable presence of all constructs within the five-hour time frame with all structures mostly (~90%) digested after 24 hours of incubation.

Example 3

Locking and Unlocking Thrombin Activity by Anticoagulant Fibers and Kill-Switches Three coagulation pathways have been described. The contact activation, or intrinsic pathway is activated by trauma within the vascular system. The tissue factor, or extrinsic pathway is activated by trauma-induced blood loss outside of the vascular system and is always more rapid than the intrinsic system. The common pathway is the final step in both aforementioned pathways, ultimately yielding fibrin formation[34]. In vitro/ex vivo coagulation assays assess blood clot formation via these mechanisms as follows (Tables 2 and 3A-3B): Activated Partial Thromboplastin Time (APTT) measures the functionality of the intrinsic pathway; Prothrombin Time (PT) assesses the extrinsic pathway; Thrombin Time (TT) evaluates the common pathway. Prolongation of blood coagulation in all assays (APTT, PT, and TT) is commonly considered to assess thrombin functionality due to the key role this protein plays in all pathways; for this reason, APTT, PT and TT are used in the clinic to diagnose blood coagulation deficiencies and to monitor the efficacy of anti-thrombotic therapies. When anticoagulation fibers bind to thrombin at exosite-I, fibrinogen is unable to bind to thrombin.

To evaluate the effectiveness of fibers with regard to thrombin inhibition, APTT, PT, and TT tests were performed using blood of healthy donor volunteers from both the US and Brazil. Coagulation assays were conducted according to current clinical standards utilizing World Health Organization (WHO)-certified human plasma as controls and WHO-qualified plasma coagulation reagents with known time limits for normal plasma coagulation. In the US, these standards qualified any time measurements below 13.4, 37, and 21 seconds as normal times for PT, APTT, and TT assays, respectively. Coagulation times above these limits were considered as prolongation. In Brazil, 12.1, 36.5, and 16.6 seconds were normal times for PT, APTT, and TT assays, respectively. In both studies, aptamers alone resulted in a slight prolongation of the plasma coagulation time in the APTT assay, but not in PT or TT assays (Table 3A, plasma versus NU172 and RA-36 aptamers). The non-functionalized fibers did not alter normal plasma coagulation time. Likewise, when used alone (i.e., without the fiber support), anticoagulant aptamers at tested concentrations did not significantly affect plasma coagulation and only slightly prolonged the plasma coagulation time (Table 3A and 3B). However, when the same aptamers were immobilized on fibers, significant prolongation, and, therefore, improved efficacy, were observed in all three assays. This confirms that the anticoagulant potency of aptamers can be significantly improved by their co-delivery on fiber backbones. To verify that the action of anticoagulant fibers can be controlled, the Tables 3A and 3B. Plasma coagulation assessment. (A) Results of prothrombin time (PT), activated partial thromboplastin time (APTT), and thrombin time (TT) of anti-thrombin fibers for their abilities in delaying the coagulation in donors from the United States and Brazil, displaying some minor regional variations. (B) The addition of kill-switch fibers restored the normal coagulation time. In this study, whole blood was collected from donors from the United States only.

A

| Sample | PT U.S. Data (13.4 s *) | PT Brazil Data (12.1 s *) | APTT U.S. Data (37.0 s *) | APTT Brazil Data (36.5 s *) | TT U.S. Data (21.0 s *) | TT Brazil Data (16.6 s *) |
|---|---|---|---|---|---|---|
| NU Fiber | 17.3 ± 0.2 | 16.6 ± 0.3 | >120.00 | 89.4 ± 1.4 | >60.00 | 26.8 ± 0.2 |
| RA Fiber | 16.6 ± 0.4 | 19.7 ± 0.2 | 70.9 ± 5.0 | 104.7 ± 1.9 | >60.00 | 31.6 ± 0.6 |
| NU/RA Fiber | 16.8 ± 0.4 | 17.7 ± 0.0 | 81.3 ± 4.3 | 100.4 ± 1.5 | >60.00 | 28.6 ± 0.0 |
| DNA-RNA Fiber | 11.8 ± 0.3 | 13.5 ± 0.2 | 36.7 ± 0.8 | 40.2 ± 0.1 | 15.8 ± 0.7 | 19.3 ± 0.1 |
| Plasma | 10.8 ± 0.2 | 13.6 ± 0.2 | 33.4 ± 1.2 | 28.6 ± 0.3 | 16.6 ± 0.3 | 19.4 ± 0.1 |
| NU172 Aptamer | 10.9 ± 0.2 | 14.1 ± 0.2 | 38.0 ± 1.5 | 39.5 ± 0.1 | 15.3 ± 0.8 | 19.0 ± 0.2 |
| RA-36 Aptamer | 11.3 ± 0.4 | 15.3 ± 0.5 | 41.5 ± 3.2 | 45.5 ± 0.8 | 16.6 ± 0.8 | 26.5 ± 0.5 |

B

| Sample | PT (13.4 s *) | APTT (37.0 s *) | TT (21.0 s *) |
|---|---|---|---|
| Control (Normal) | 12.7 ± 0.2 | 36.8 ± 1.5 | 21.4 ± 0.6 |
| Control (Abnormal) | 20.7 ± 0.4 | 71.8 ± 1.4 | 41.3 ± 1.4 |
| Plasma | 9.7 ± 0.0 | 29.4 ± 0.2 | 16.1 ± 0.3 |
| NU172 Aptamer | 16.1 ± 0.5 | 37.9 ± 0.7 | 25.3 ± 1.8 |
| RA-36 Aptamer | 17.3 ± 0.3 | 44.2 ± 0.6 | 45.0 ± 1.4 |
| NU Fiber | 18.6 ± 1.7 | 101.7 ± 2.0 | 59.5 ± 0.5 |
| NU Fiber + Kill-Switch | 10.9 ± 0.1 | 36.7 ± 0.2 | 17.5 ± 0.4 |
| RA Fiber | 20.8 ± 0.1 | 89.9 ± 1.1 | >60.00 |
| RA Fiber + Kill-Switch | 13.7 ± 0.1 | 42.9 ± 0.3 | 44.7 ± 0.1 |
| NU/RA Fiber | 16.8 ± 0.9 | 95.3 ± 3.0 | >60.00 |
| NU/RA Fiber + Kill-Switch | 10.6 ± 0.3 | 38.5 ± 0.4 | 18.4 ± 0.6 |

Data shown as mean ± SD, N = 3.

* Normal coagulation time of PT, APTT and TT are adapted from NCI method ITA-12.

Control (Normal) and Control (Abnormal) are WHO-certified plasma samples used to qualify instrument and reagents performance.

plasma coagulation times were assessed after kill-switches were added to the same set of plasma specimens; the plasma coagulation times in all three assays returned to normal, consistent with the expected mechanism of action (Table 3B).

Example 4

Immunorecognition of Anticoagulant Fibers

Since anticoagulant fibers are intended for intravenous administration, it is crucial to determine whether they can induce cytokine responses or complement activation (FIGS. 6A-6C), both of which represent immunostimulatory reactions commonly reported as dose-limiting toxicity of therapeutic oligonucleotides[35-36]. To assess the magnitude of associated cytokine production, human peripheral blood mononuclear cells (PBMCs) were treated with each construct. PBMCs were chosen as a model system that provides more accurate predictions of cytokine storm toxicity in humans among all preclinical models. All constructs were tested for endotoxin contamination prior to introduction to PBMCs and the activation of complement and induction of proinflammatory cytokine responses were analyzed.

The complement system plays an essential role in innate immunity[37]. This system is composed of over 30 plasma proteins that trigger a proteolytic cascade upon activation, resulting in the production of opsonins, anaphylatoxins, and the terminal membrane-attack complex whose coordinated function leads to immune cell activation and the destruction of invading pathogens[37]. There are three pathways of complement activation: lectin, classical, and alternative. Activation of any of these pathways involves a series of cleavage reactions culminating in the formation of C3 convertase[38]. C3 convertase cleaves the C3 complement component into several split products, some of which, e.g., C3a, act as anaphylatoxins, whereas others, e.g., C3b, act as opsonins[38]. C3b fragment is unstable and quickly degrades to iC3b, which can be quantified and therefore serves as a biomarker of complement activation. Here, an immunoassay was used to detect the presence of iC3b (FIG. 6B). Cobra venom factor (CVF), a known complement-activating protein, and clinically used PEGylated liposomal doxorubicin formulation (DOXIL©), known to cause complement activation-related pseudoallergy in sensitive patients, were used as positive controls[39]. The data show that activation by any of the constructs is less than that seen with DOXIL©. Although these results do not completely rule out potential complement activation at higher concentrations or in particularly sensitive individuals, the outcomes suggest negligible stimulation of the complement system by anticoagulant fibers in vitro for comparable safety with regards to the complement activation in vivo.

The immunostimulatory response in PBMCs was assessed with a multiplex panel including 15 cytokines of different families produced by various cells composing PBMCs and activated by various inflammatory pathways (FIG. 6C). PBMCs were isolated from the blood of three healthy human donors and treated with increasing concentrations of fibers. A combination of lipopolysaccharide (LPS), ODN2216, and phytohemagglutinin (PHA-M) was used as a positive control due to their abilities to activate inflammatory cytokines and types I and II IFNs in PBMCs. Relative to the positive controls, the production of ILs and IFNs by cells exposed to anticoagulant fibers was negligible. This data is in agreement with earlier studies reporting that carrier-free nucleic acid constructs are immunoquiescent due to their inability to enter the endosomal compartment of cells[33, 40] where many nucleic acid-specific receptors are localized. These data suggested that the possibility of endothelial activation and thrombogenicity stemming from a material-activated immune response is negligible[41] and warranted further evaluation of anticoagulant fibers in vivo.

Example 5

Biodistribution and Conditional Retention of Anticoagulant Fibers

Figure 7A:
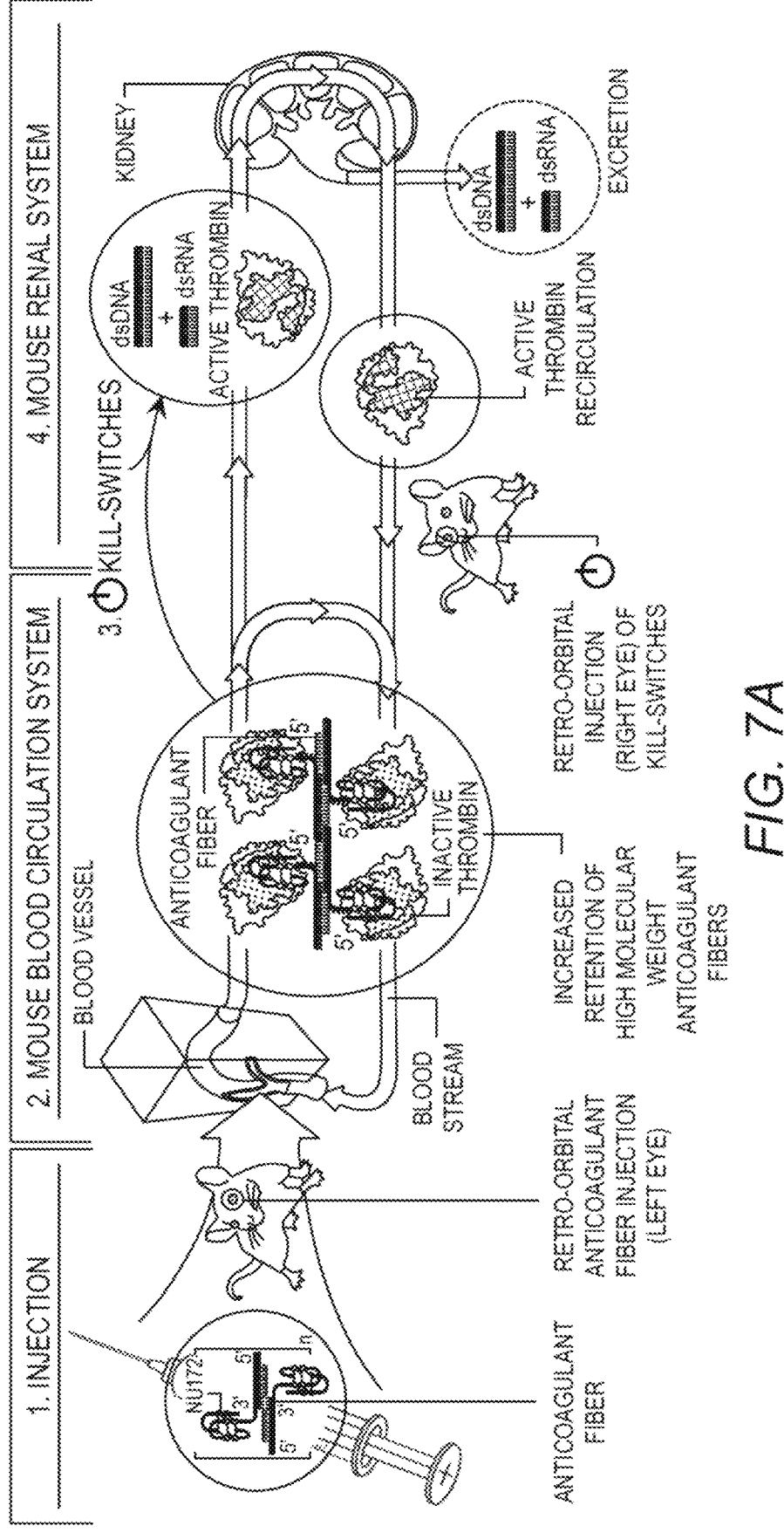
Figure 7B:
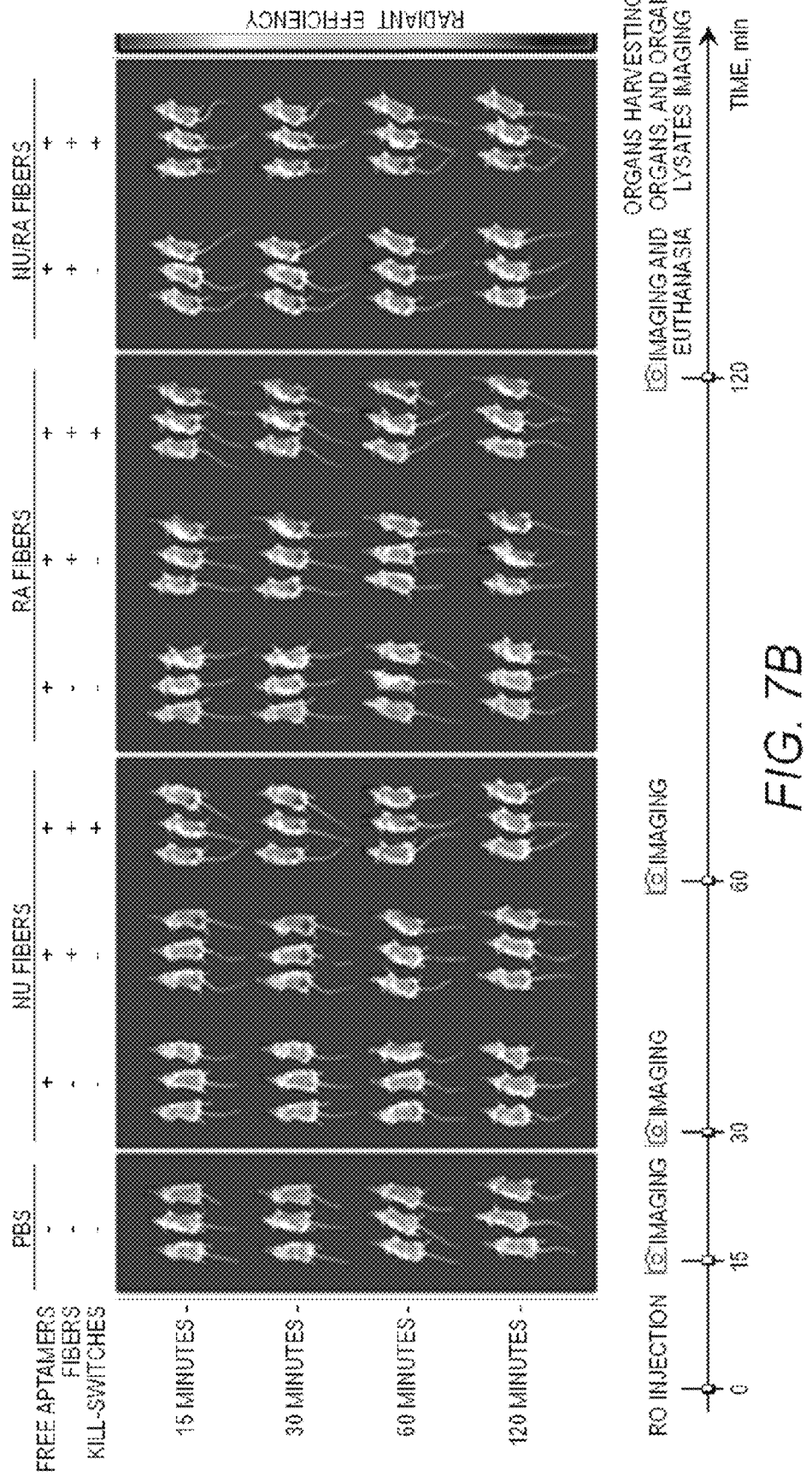
Figures 7C, 7D, 7E:
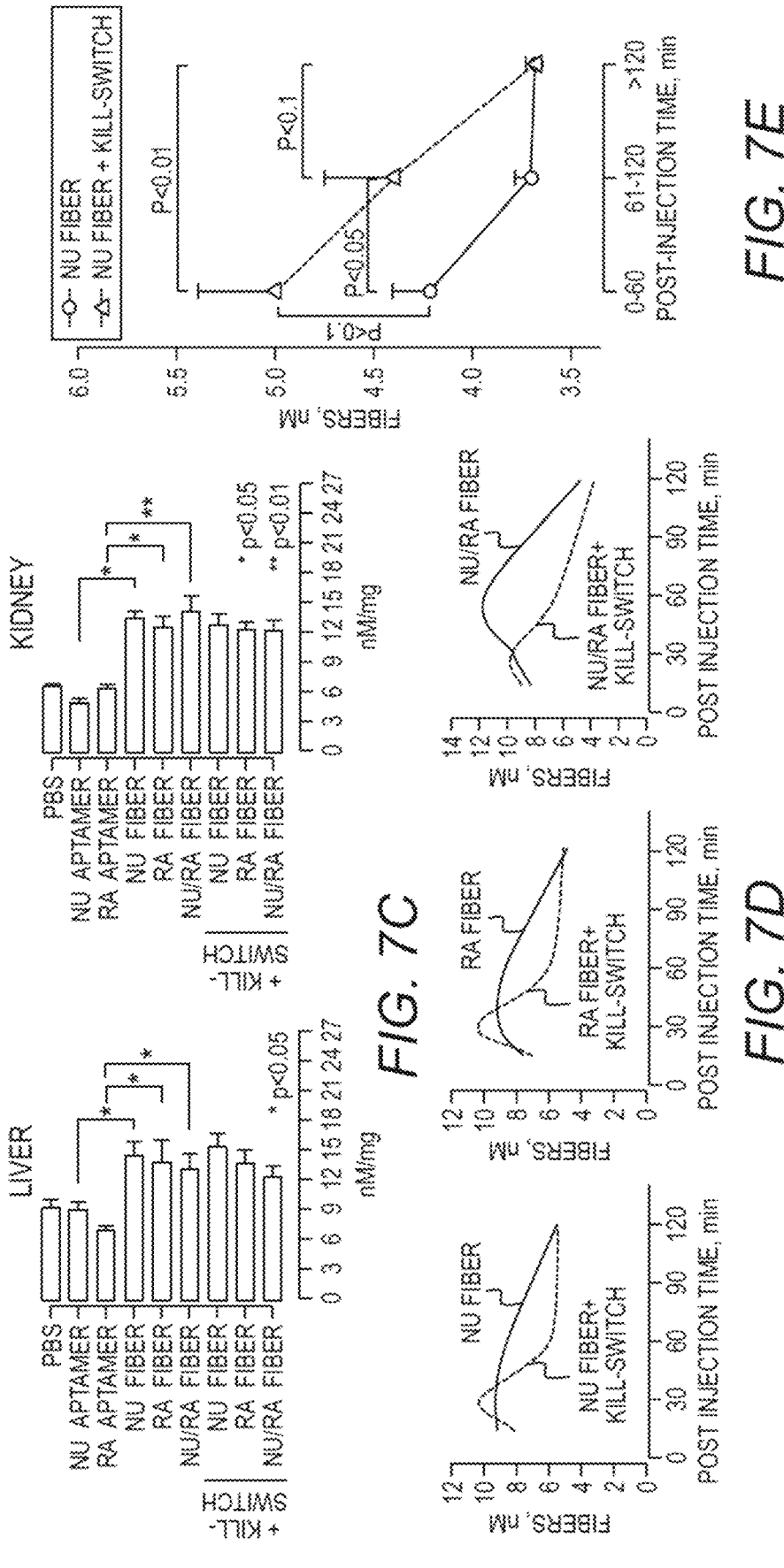

Endotoxin-free fluorescently labeled anticoagulant fibers and kill-switches were administered to BALB/c mice via retro-orbital injection. Biodistributions were evaluated using an in vivo optical imaging system (IVIS) at various time points post-injection (FIG. 7A). Whole-body fluorescence analysis revealed a strong signal in the bladder region (FIG. 7B). Compared to free aptamers, anticoagulant fibers exhibited prolonged accumulation in the bladder, indicating delayed renal excretion. Following the administration of corresponding kill-switches, rapid excretion was observed due to re-association and the concomitant generation of short DNA and RNA duplexes. Since the whole-body imaging may not be accurate in providing a sufficient level of detail about the biodistribution, additional ex vivo imaging was carried out. The liver, kidneys, heart, and lungs were harvested and imaged two hours post-injection (FIG. 8B). Liver tissues displayed the highest level of fluorescence in most animals. To estimate the concentrations of the constructs, liver and kidney lysates were processed and their fluorescent signal intensities were measured which, in turn, reflected concentrations of the constructs (FIG. 7C). Based on the analysis, the concentrations of anticoagulation fibers were found to be much higher than those of free aptamers. However, the animals that were also injected with kill-switches displayed no obvious difference due to excretion of constructs via urine throughout the duration of the experiments. Next, the fluorescence intensity of the bladder from the in vivo images was recorded and converted to concentration (FIG. 7D) using a calibration curve (y=0.00000005485x+3.01). The three pairs of anticoagulant fibers and corresponding kill-switches displayed similar trends: after ~30 minutes post-injection, anticoagulant fibers showed peak accumulation in the bladder, then the concentration decreased. NU/RA anticoagulant fibers had a smoother reduction than NU and RA anticoagulant fibers. NU/RA anticoagulant fibers also showed the lowest concentration at the endpoint of this study (two hours post-injection), which indicates that they are excreted from the system the fastest. With the addition of kill-switches, NU/RA anticoagulant fibers also showed a delayed accumulation in the bladder at ~60 minutes post-injection compared to a slight increase seen for the other two constructs. In agreement with in vitro tests, the anticoagulant fibers with different aptamer combinations displayed different kinetics of re-association. Finally, the concentration of the anticoagulant fibers was quantified with and without kill-switches in mouse urine samples (FIG. 7E). Urine was collected immediately after each mouse urinated and the time duration from injection to urination was recorded. According to the results, kill-switches significantly increased the excretion rate of anticoagulation fiber components that is different from earlier studies with other types of nanomaterial-formulated aptamers[42]. These data are consistent with earlier studied reporting a rapid clearance of free aptamers from the blood stream and accumulation in the liver and kidneys[43]. Prolonged circulation of PEGylated aptamers and aptamers delivered by nanoparticles as compared to the free aptamers have also been reported[44].

Example 5

In Vivo Function of Anticoagulant Fibers and Kill-Switches

Figure 10A:
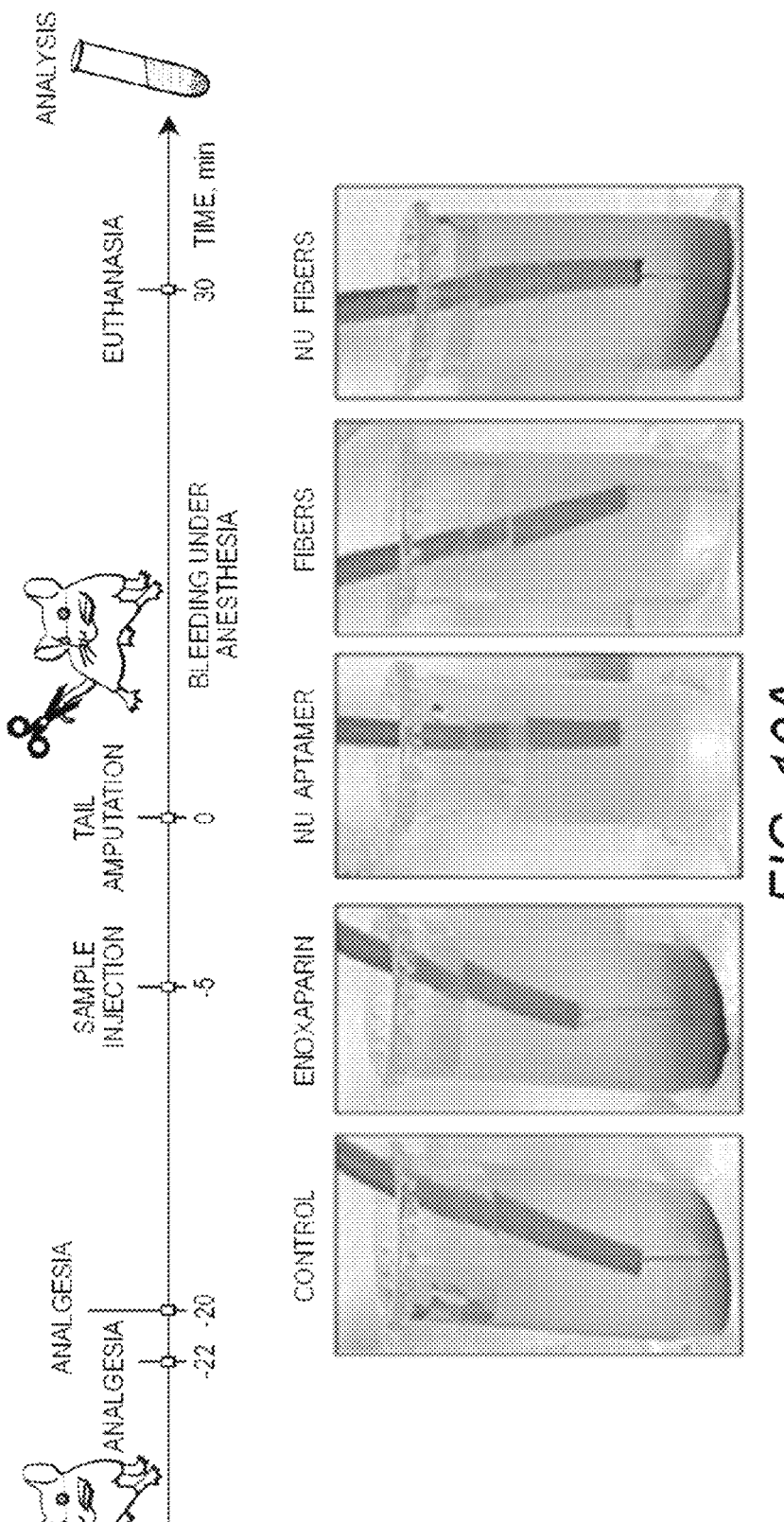
Figures 10B, 10C, 10D:
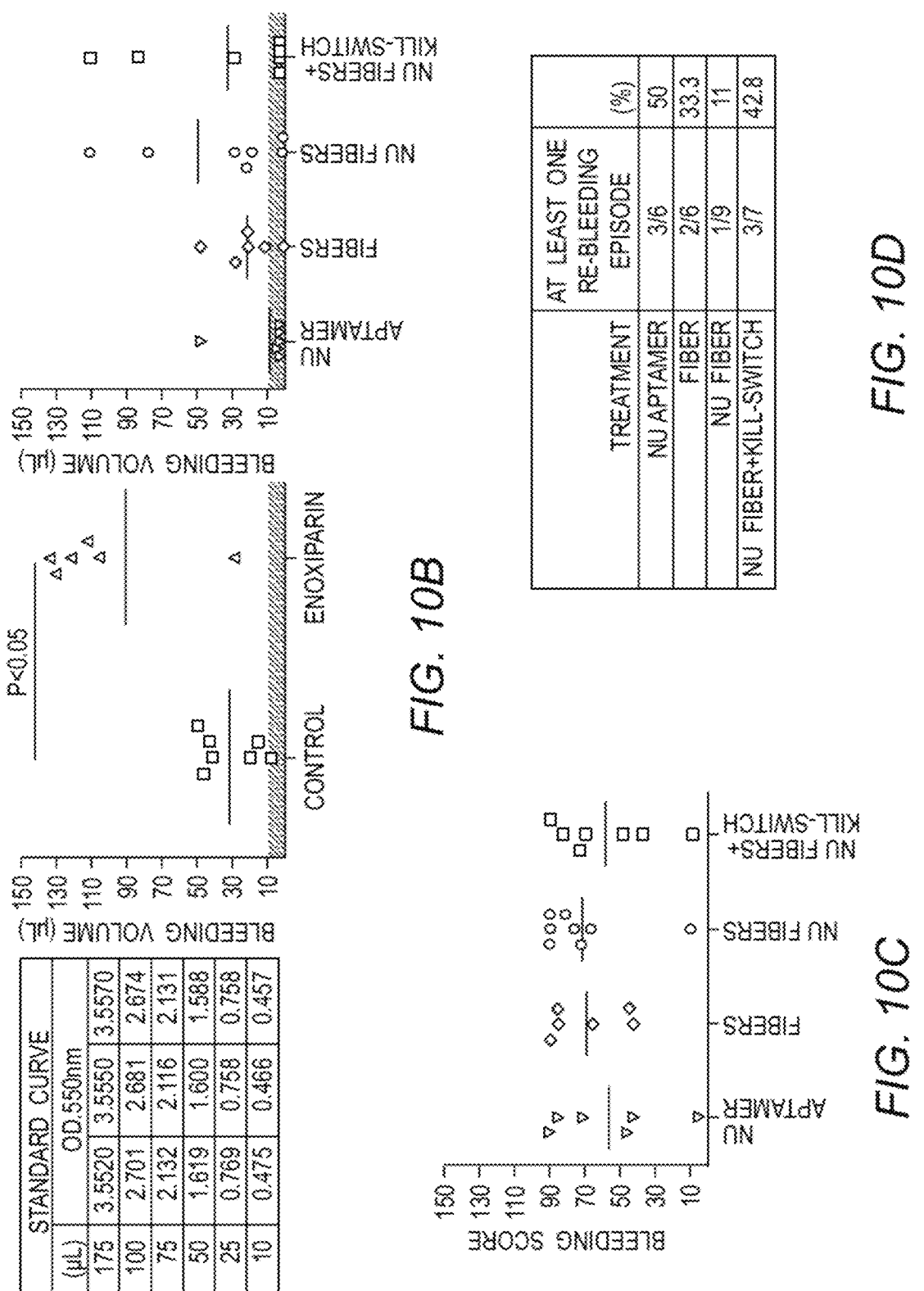

To determine whether anticoagulant fibers interfere in normal hemostasis in vivo, we performed a murine tail-bleeding experiment was performed[45] (FIGS. 9A-9C). To comply with internationally recognized 3R principles of research animal care and use[46], the study was narrowed down to NU172 fibers and free aptamers as representative materials. The duration of bleeding was similar among the groups, and the majority of animals bled during the 30 minutes of the assay. The overall prolonged bleeding time in vivo for all samples could be explained by the effect of anesthetics on the coagulation system. Xylazine and isoflurane can cause vasodilatation, and increase basal blood flow velocity, inhibiting or reducing the effect of anticoagulants and promoting variable results due to unstable thrombi events[47]. Additionally, episodes of intermittent bleeding and variation in bleeding flow were observed. Therefore, bleeding time alone was insufficient to determine the hemostatic effect of the anticoagulant fibers, so the total volume of bleeding was estimated by assessing hemoglobin concentration (FIGS. 10A-10D). The treatment with control anticoagulant enoxaparin resulted in an increased bleeding volume as compared with negative control treated animals ($p<0.05$). When comparing NU anticoagulant fibers with non-functional fibers and NU aptamers, an increase in the bleeding volume was observed, which was partially reversed by the kill-switch fibers. Importantly, bleeding samples from animals treated with NU anticoagulant fibers exhibited a decreased formation of blood clots (33.3%) as compared to controls (83.3%) and was completely recovered after the injection of kill-switches (100%) (FIGS. 9A and 9B). As would be expected, animals treated with NU anticoagulant fibers, which showed less clot formation, lost a higher blood volume over the course of the experiment, while animals treated with free aptamers, which exhibited a higher degree of clotting, lost lower volumes of blood (FIG. 9A). This relationship between clotting and blood volume lost was evident in the comparison of clots from blood samples of control animals when compared to animals treated with enoxaparin (FIG. 10B). To quantify the bleeding flow variation over time, all bleeding flow episodes were annotated for each animal along the experiment, and bleeding flow intensity categorized as low, medium or high. Then a bleeding score was determined by assigning factors 1-3 to the bleeding times corresponding to each flow intensity (FIG. 10C). Events of progressive reduction of bleeding until cessation, followed by an abrupt restart of bleeding, termed re-bleeding episodes, were found decreased in mice treated with NU anticoagulant fibers (11%) while controls treated with NU aptamers and fibers, exhibited 50% and 33%, respectively (FIG. 10D). Notably, this phenomenon was reversed by the kill-switch treatment of NU anticoagulant fibers (42.8%). The re-bleeding occurrence suggests a partial inhibition of platelets' hemostatic action, which generates unstable thrombi formation that can be detached under blood flow. These results point towards an increased antithrombotic activity of anticoagulant fibers, despite the possible interference of the anesthetic drugs used in the experiments. These results were confirmed in Yorkshire swine models demonstrating prolongation of blood coagulation, measured by TT assessment, after the injection of anticoagulant fibers and restoration of the normal blood coagulation after the injection of kill-switches (FIG. 9C). During these experiments, the systemic arterial pressure, heart rate and ETCO2 were also assessed, which did not change significantly (Table 4). All blood cell counts, and blood chemistry analysis results were normal at all timepoints.

TABLE 4

Hemodynamic parameters monitored in Yorkshire swine model after the injection with anticoagulant fibers and kill-switches.

| Animal 1 | Baseline at 0 min | +NU fibers at 30 min | +Kill-switches at 60 min |
|---|---|---|---|
| PAP (mmHg) | 12 | 11 | 12 |
| SAP (mmHg) | 69 | 67 | 64 |
| HR (BPM) | 100 | 97 | 98 |
| ETCO2 (mmHg) | 39 | 39 | 39 |
| Animal 2 | Baseline | 30 min | 30 min |
| PAP (mmHg) | 15 | 13 | 11 |
| SAP (mmHg) | 67 | 58 | 59 |
| HR (BPM) | 73 | 72 | 68 |
| ETCO2 (mmHg) | 37 | 38 | 38 |

Overall, using in vitro assays and two in vivo models, a successful inhibition of blood coagulation was demonstrated using RNA-DNA anticoagulant fibers and the restoration of normal blood coagulation time by their complementary kill-switches. The use of low-cost materials makes this strategy attractive for clinical use, especially in comparison to currently available antidotes for direct thrombin inhibitors (e.g., idarucizumab, a monoclonal antibody[48]). Moreover, it was demonstrated that the new anticoagulant fibers and their kill-switches are biocompatible and do not induce overt complement and cytokine activation. In vivo biodistribution studies reveal that anticoagulant fibers mostly accumulate in the liver and kidneys two hours post-injection. Short DNA and RNA duplexes resulting from the isothermal re-association process between anticoagulant fibers and their corresponding kill-switches increased the rate of excretion in urine.

This invention introduces a new concept that allows for the construction of biocompatible reconfigurable nucleic acid nanoassemblies that enable controlled blood coagulation both in vitro and in vivo. It is envisioned that the design principles of regulated anticoagulation described in this work would help to address current global public health challenges related to cardiovascular diseases and thrombosis-driven complications from infectious diseases such as COVID-19. The regulated anticoagulation may also help overcome the issue of anticoagulant drug overdose and improve the overall safety of anticoagulants.

The foregoing is illustrative of the present invention, and is not to be construed as limiting thereof. The invention is defined by the following claims, with equivalents of the claims to be included therein.

REFERENCES

1. Esmon, C. T.; Xu, J.; Lupu, F., Innate immunity and coagulation. *J Thromb Haemost* 2011, 9 Suppl 1, 182-8.
2. Prandoni, P.; Falanga, A.; Piccioli, A., Cancer, thrombosis and heparin-induced thrombocytopenia. *Thromb Res* 2007, 120 Suppl 2, S137-40.

3. ten Cate, H.; Falanga, A., Overview of the postulated mechanisms linking cancer and thrombosis. *Pathophysiol Haemost Thromb* 2008, 36 (3-4), 122-30.

4. Mackman, N.; Bergmeier, W.; Stouffer, G. A.; Weitz, J. I., Therapeutic strategies for thrombosis: new targets and approaches. *Nature Reviews Drug Discovery* 2020, 19 (5), 333-352.

5. Kushner, A.; West, D.; Pillarisetty, L. S., Virchow Triad. 2019.

6. Araya, S.; Mamo, M. A.; Tsegay, Y. G.; Atlaw, A.; Aytenew, A.; Hordofa, A.; Negeso, A. E.; Wordofa, M.; Niguse, T.; Cheru, M.; Tamir, Z., Blood coagulation parameter abnormalities in hospitalized patients with confirmed COVID-19 in Ethiopia. *PLoS One* 2021, 16 (6), e0252939.

7. Rajabto, W.; Priantono, D.; Mulyadi, R., Pulmonary Embolism in Hospitalized Patient with Coronavirus Disease 2019 (COVID-19). *Acta Med Indones* 2021, 53 (4), 493-496.

8. Cook, B. W., Anticoagulation management. *Semin Intervent Radiol* 2010, 27 (4), 360-7.

9. Nutescu, E. A.; Burnett, A.; Fanikos, J.; Spinler, S.; Wittkowsky, A., Pharmacology of anticoagulants used in the treatment of venous thromboembolism. *J. Thromb. Thrombolysis* 2016, 41 (1), 15-31.

10. Hong, E.; Halman, J. R.; Shah, A.; Cedrone, E.; Truong, N.; Afonin, K. A.; Dobrovolskaia, M. A., Toll-Like Receptor-Mediated Recognition of Nucleic Acid Nanoparticles (NANPs) in Human Primary Blood Cells. *Molecules* 2019, 24 (6), 1094.

11. Panigaj, M.; Johnson, M. B.; Ke, W.; McMillan, J.; Goncharova, E. A.; Chandler, M.; Afonin, K. A., Aptamers as Modular Components of Therapeutic Nucleic Acid Nanotechnology. *ACS Nano* 2019, 13 (11), 12301-12321.

12. Johnson, M. B.; Chandler, M.; Afonin, K. A., Nucleic acid nanoparticles (NANPs) as molecular tools to direct desirable and avoid undesirable immunological effects. *Adv Drug Deliv Rev* 2021, 173, 427-438.

13. Bouchard, P. R.; Hutabarat, R. M.; Thompson, K. M., Discovery and development of therapeutic aptamers. *Annu Rev Pharmacol Toxicol* 2010, 50, 237-57.

14. Woodruff, R. S.; Sullenger, B. A., Modulation of the Coagulation Cascade Using Aptamers. *Arterioscler Thromb Vasc Biol* 2015, 35 (10), 2083-91.

15. Chan, M. Y.; Cohen, M. G.; Dyke, C. K.; Myles, S. K.; Aberle, L. G.; Lin, M.; Walder, J.; Steinhubl, S. R.; Gilchrist, I C.; Kleiman, N. S.; Vorchheimer, D. A.; Chronos, N.; Melloni, C.; Alexander, J. H.; Harrington, R. A.; Tonkens, R. M.; Becker, R. C.; Rusconi, C. P., Phase 1b randomized study of antidote-controlled modulation of factor IXa activity in patients with stable coronary artery disease. *Circulation* 2008, 117 (22), 2865-74.

16. Chan, M. Y.; Rusconi, C. P.; Alexander, J. H.; Tonkens, R. M.; Harrington, R. A.; Becker, R. C., A randomized, repeat-dose, pharmacodynamic and safety study of an antidote-controlled factor IXa inhibitor. *J Thromb Haemost* 2008, 6 (5), 789-96.

17. Dyke, C. K.; Steinhubl, S. R.; Kleiman, N. S.; Cannon, R. O.; Aberle, L. G.; Lin, M.; Myles, S. K.; Melloni, C.; Harrington, R. A.; Alexander, J. H.; Becker, R. C.; Rusconi, C. P., First-in-human experience of an antidote-controlled anticoagulant using RNA aptamer technology: a phase 1a pharmacodynamic evaluation of a drug-antidote pair for the controlled regulation of factor IXa activity. *Circulation* 2006, 114 (23), 2490-7.

18. Krissanaprasit, A.; Key, C. M.; Froehlich, K.; Pontula, S.; Mihalko, E.; Dupont, D. M.; Andersen, E. S.; Kjems, J.; Brown, A. C.; LaBean, T. H., Multivalent Aptamer-Functionalized Single-Strand RNA Origami as Effective, Target-Specific Anticoagulants with Corresponding Reversal Agents. *Adv Healthc Mater* 2021, 10 (11), e2001826.

19. Rusconi, C. P.; Scardino, E.; Layzer, J.; Pitoc, G. A.; Ortel, T. L.; Monroe, D.; Sullenger, B. A., RNA aptamers as reversible antagonists of coagulation factor IXa. *Nature* 2002, 419 (6902), 90-4.

20. Zhao, S.; Tian, R.; Wu, J.; Liu, S.; Wang, Y.; Wen, M.; Shang, Y.; Liu, Q.; Li, Y.; Guo, Y.; Wang, Z.; Wang, T.; Zhao, Y.; Zhao, H.; Cao, H.; Su, Y.; Sun, J.; Jiang, Q.; Ding, B., A DNA origami-based aptamer nanoarray for potent and reversible anticoagulation in hemodialysis. *Nat Commun* 2021, 12 (1), 358.

21. Raber M N, W. H., Hall W D, Hurst J W Coagulation Tests. *Clinical Methods: The History, Physical, and Laboratory Examinations.* 3rd edition 1990, (Boston: Butterworths), Chapter 157.

22. De Cristofaro, R.; De Candia, E., Thrombin domains: Structure, function and interaction with platelet receptors. *J. Thromb. Thrombolysis* 2003, 15 (3), 151-163.

23. Di Cera, E., Thrombin. *Mol Aspects Med* 2008, 29 (4), 203-54.

24. Bock, L. C.; Griffin, L. C.; Latham, J. A.; Vermaas, E. H.; Toole, J. J., Selection of single-stranded DNA molecules that bind and inhibit human thrombin. *Nature* 1992, 355 (6360), 564-6.

25. Kretz, C. A.; Stafford, A. R.; Fredenburgh, J. C.; Weitz, J. I., HD1, a thrombin-directed aptamer, binds exosite 1 on prothrombin with high affinity and inhibits its activation by prothrombinase. *J Biol Chem* 2006, 281 (49), 37477-85.

26. Mayer, G.; Rohrbach, F.; Potzsch, B.; Muller, J., Aptamer-based modulation of blood coagulation. *Hamostaseologie* 2011, 31 (4), 258-63.

27. Zavyalova, E.; Golovin, A.; Reshetnikov, R.; Mudrik, N.; Panteleyev, D.; Pavlova, G.; Kopylov, A., Novel modular DNA aptamer for human thrombin with high anticoagulant activity. *Curr Med Chem* 2011, 18 (22), 3343-50.

28. Zavyalova, E.; Samoylenkova, N.; Revishchin, A.; Turashev, A.; Gordeychuk, I.; Golovin, A.; Kopylov, A.; Pavlova, G., The Evaluation of Pharmacodynamics and Pharmacokinetics of Anti-thrombin DNA Aptamer RA-36. *Frontiers in Pharmacology* 2017, 8.

29. Roxo, C.; Kotkowiak, W.; Pasternak, A., G-Quadruplex-Forming Aptamers-Characteristics, Applications, and Perspectives. *Molecules* 2019, 24 (20), 3781.

30. Zavyalova, E.; Golovin, A.; Pavlova, G.; Kopylov, A., Module-Activity Relationship of G-quadruplex Based DNA Aptamers for Human Thrombin. *Current Medicinal Chemistry* 2013, 20 (38), 4836-4843.

31. Zavyalova, E.; Samoylenkova, N.; Revishchin, A.; Golovin, A.; Pavlova, G.; Kopylov, A., Evaluation of Antithrombotic Activity of Thrombin DNA Aptamers by a Murine Thrombosis Model. *Plos One* 2014, 9 (9), 7.

32. Becker, R. C.; Povsic, T.; Cohen, M. G.; Rusconi, C. P.; Sullenger, B., Nucleic acid aptamers as antithrombotic agents: Opportunities in extracellular therapeutics. *Thromb Haemost* 2010, 103 (3), 586-95.

33. Ke, W.; Hong, E.; Saito, R. F.; Rangel, M. C.; Wang, J.; Viard, M.; Richardson, M.; Khisamutdinov, E. F.; Panigaj, M.; Dokholyan, N. V.; Chammas, R.; Dobrovolskaia, M. A.; Afonin, K. A., RNA-DNA fibers and polygons with controlled immunorecognition activate RNAi, FRET and transcriptional regulation of NF-kappaB in human cells. *Nucleic Acids Res* 2019, 47 (3), 1350-1361.
34. Palta, S.; Saroa, R.; Palta, A., Overview of the coagulation system. *Indian J Anaesth* 2014, 58 (5), 515-523.
35. Henry, S. P.; Jagels, M. A.; Hugh, T. E.; Manalili, S.; Geary, R. S.; Giclas, P. C.; Levin, A. A., Mechanism of alternative complement pathway dysregulation by a phosphorothioate oligonucleotide in monkey and human serum. *Nucleic Acid Ther* 2014, 24 (5), 326-35.
36. Paz, S.; Hsiao, J.; Cauntay, P.; Soriano, A.; Bai, L.; Machemer, T.; Xiao, X.; Guo, S.; Hung, G.; Younis, H.; Bennett, C. F.; Henry, S.; Yun, T. J.; Burel, S., The Distinct and Cooperative Roles of Toll-Like Receptor 9 and Receptor for Advanced Glycation End Products in Modulating In Vivo Inflammatory Responses to Select CpG and Non-CpG Oligonucleotides. *Nucleic Acid Ther* 2017, 27 (5), 272-284.
37. Ilinskaya, A. N.; Shah, A.; Enciso, A. E.; Chan, K. C.; Kaczmarczyk, J. A.; Blonder, J.; Simanek, E. E.; Dobrovolskaia, M. A., Nanoparticle physicochemical properties determine the activation of intracellular complement. *Nanomedicine: Nanotechnology, Biology and Medicine* 2019, 17, 266-275.
38. Janeway Jr, C. A.; Travers, P.; Walport, M.; Shlomchik, M. J., The complement system and innate immunity. In *Immunobiology: The Immune System in Health and Disease. 5th edition*, Garland Science: 2001.
39. Vogel, C. W.; Fritzinger, D. C.; Hew, B. E.; Thorne, M.; Bammert, H., Recombinant cobra venom factor. *Molecular Immunology* 2004, 41 (2-3), 191-199.
40. Hong, E.; Halman, J. R.; Shah, A. B.; Khisamutdinov, E. F.; Dobrovolskaia, M. A.; Afonin, K. A., Structure and Composition Define Immunorecognition of Nucleic Acid Nanoparticles. *Nano Lett* 2018, 18 (7), 4309-4321.
41. Markiewski, M. M.; Lambris, J. D., The role of complement in inflammatory diseases from behind the scenes into the spotlight. *Am J Pathol* 2007, 171 (3), 715-727.
42. Guo, J. W.; Gao, X. L.; Su, L. N.; Xia, H. M.; Gu, G. Z.; Pang, Z. Q.; Jiang, X. G.; Yao, L.; Chen, J.; Chen, H. Z., Aptamer-functionalized PEG-PLGA nanoparticles for enhanced anti-glioma drug delivery. *Biomaterials* 2011, 32 (31), 8010-8020.
43. Kryza, D.; Debordeaux, F.; Azema, L.; Hassan, A.; Paurelle, O.; Schulz, J.; Savona-Baron, C.; Charignon, E.; Bonazza, P.; Taleb, J.; Fernandez, P.; Janier, M.; Toulme, J. J., Ex Vivo and In Vivo Imaging and Biodistribution of Aptamers Targeting the Human Matrix MetalloProtease-9 in Melanomas. *Plos One* 2016, 11 (2).
44. Healy, J. M.; Lewis, S. D.; Kurz, M.; Boomer, R. M.; Thompson, K. M.; Wilson, C.; McCauley, T. G., Pharmacokinetics and biodistribution of novel aptamer compositions. *Pharm Res-Dordr* 2004, 21 (12), 2234-2246.
45. Liu, Y.; Jennings, N. L.; Dart, A. M.; Du, X. J., Standardizing a simpler, more sensitive and accurate tail bleeding assay in mice. *World J Exp Med* 2012, 2 (2), 30-6.
46. Russell, W. M. S.; Burch, R. L., The Principles of Humane Experimental Technique. Methuen & Co Ltd.; London, U K 1959.
47. Sashindranath, M.; Sturgeon, S. A.; French, S.; Craenmehr, D. D. D.; Selan, C.; Freddi, S.; Johnson, C.; Cody, S. H.; Nesbitt, W. S.; Hamilton, J. R.; Nandurkar, H. H., The mode of anesthesia influences outcome in mouse models of arterial thrombosis. *Res Pract Thromb Haemost* 2019, 3 (2), 197-206.
48. Pollack Jr, C. V.; Reilly, P. A.; Eikelboom, J.; Glund, S.; Verhamme, P.; Bernstein, R. A.; Dubiel, R.; Huisman, M. V.; Hylek, E. M.; Kamphuisen, P. W., Idarucizumab for dabigatran reversal. *New England Journal of Medicine* 2015, 373 (6), 511-520.

That which is claimed is:

1. A single strand DNA molecule comprising:
   a) a polynucleotide of about 40 to about 70 nucleotides in length, the polynucleotide comprising:
      an RNA binding sequence of about 20 to about 30 nucleotides in length; and
      a toehold sequence of about 10 to about 20 nucleotides length linked to the 5' and 3' ends of the RNA binding sequence; and
   b) an aptamer linked to the 5' and/or 3' end of the polynucleotide;
   wherein the aptamer(s) binds an extracellular target.

2. A complex comprising the single strand DNA molecule of claim 1, wherein the single strand DNA molecule is hybridized to a single strand RNA molecule of about 20 to about 30 nucleotides in length that is at least 80% complementary to the RNA binding sequence of the single strand DNA molecule.

3. The single strand DNA molecule of claim 1, wherein the polynucleotide is about 40 to about 50 nucleotides in length.

4. The single strand DNA molecule of claim 1, wherein the RNA binding sequence is about 25 to about 27 nucleotides in length.

5. The single strand DNA molecule of claim 1, wherein the toehold sequence is about 12 to about 15 nucleotides in length.

6. The single strand DNA molecule of claim 1, wherein the aptamer is a DNA aptamer.

7. The single strand DNA molecule of claim 1 wherein the aptamer is an RNA aptamer.

8. The single strand DNA molecule of claim 1, wherein the aptamer and/or the polynucleotide comprise one or more chemically modified nucleotides.

9. The single strand DNA molecule of claim 1, wherein the aptamer is linked to the 5' end of the polynucleotide.

10. The single strand DNA molecule of claim 1, wherein the aptamer is linked to the 3' end of the polynucleotide.

11. The single strand DNA molecule of claim 1, wherein the aptamer is linked to the 5' end of the polynucleotide and the 3' end of the polynucleotide and the aptamers are the same.

12. The single strand DNA molecule of claim 1, wherein the aptamer is linked to the 5' end of the polynucleotide and the 3' end of the polynucleotide and the aptamers are different.

13. The single strand DNA molecule of claim 1, wherein the aptamer(s) bind thrombin.

14. The single strand DNA molecule of claim 13, wherein the aptamer(s) are selected from NU172, RA-36, ARC 183, HD1, HD22, TBA, Toggle-25t, TBA15/G15D, TBA29, 5'-thiol modified thrombin-binding aptamer, anti-thrombin aptamer with caged thymidine nucleobases, modified thrombin binding aptamer (mTBA), aptamer number 5, or 31-TBA.

15. The complex of claim 2, wherein the single strand RNA molecule is about 25 to about 27 nucleotides in length.

* * * * *

SEQUENCE LISTING

```
Sequence total quantity: 39
SEQ ID NO: 1            moltype = DNA  length = 26
FEATURE                 Location/Qualifiers
source                  1..26
                        mol_type = other DNA
                        organism = synthetic construct
SEQUENCE: 1
cgcctaggtt gggtagggtg gtggcg                                          26

SEQ ID NO: 2            moltype = DNA  length = 26
FEATURE                 Location/Qualifiers
source                  1..26
                        mol_type = other DNA
                        organism = synthetic construct
misc_feature            1
                        note = Alexa Fluor 750 NHS Ester
SEQUENCE: 2
cgcctaggtt gggtagggtg gtggcg                                          26

SEQ ID NO: 3            moltype = DNA  length = 31
FEATURE                 Location/Qualifiers
source                  1..31
                        mol_type = other DNA
                        organism = synthetic construct
SEQUENCE: 3
ggttggtgtg gttggtggtt ggtgtggttg g                                    31

SEQ ID NO: 4            moltype = DNA  length = 31
FEATURE                 Location/Qualifiers
source                  1..31
                        mol_type = other DNA
                        organism = synthetic construct
misc_feature            1
```

```
                              note = Alexa Fluor 750 NHS Ester
SEQUENCE: 4
ggttggtgtg gttggtggtt ggtgtggttg g                                            31

SEQ ID NO: 5              moltype = DNA   length = 111
FEATURE                  Location/Qualifiers
source                   1..111
                         mol_type = other DNA
                         organism = synthetic construct
SEQUENCE: 5
cgcctaggtt gggtagggtg gtggcgtttt ccctttaggg aatgaccctg aagttcatct   60
gcaccaccga gggaaatccc tttttcgcct aggttgggta gggtggtggc g            111

SEQ ID NO: 6              moltype = DNA   length = 111
FEATURE                  Location/Qualifiers
source                   1..111
                         mol_type = other DNA
                         organism = synthetic construct
SEQUENCE: 6
cgcctaggtt gggtagggtg gtggcgtttt tccctaaagg gatgaccctg aagttcatct   60
gcaccaccga agggatttcc cttttcgcct aggttgggta gggtggtggc g            111

SEQ ID NO: 7              moltype = DNA   length = 121
FEATURE                  Location/Qualifiers
source                   1..121
                         mol_type = other DNA
                         organism = synthetic construct
SEQUENCE: 7
ggttggtgtg gttggtggtt ggtgtggttg gttttccctt tagggaatga ccctgaagtt   60
catctgcacc accgagggaa atcctttttt ggttggtgtg gttggtggtt ggtgtggttg   120
g                                                                    121

SEQ ID NO: 8              moltype = DNA   length = 121
FEATURE                  Location/Qualifiers
source                   1..121
                         mol_type = other DNA
                         organism = synthetic construct
SEQUENCE: 8
ggttggtgtg gttggtggtt ggtgtggttg gtttttccct aaagggatga ccctgaagtt   60
catctgcacc accgaaggga tttccctttt ggttggtgtg gttggtggtt ggtgtggttg   120
g                                                                    121

SEQ ID NO: 9              moltype = DNA   length = 82
FEATURE                  Location/Qualifiers
source                   1..82
                         mol_type = other DNA
                         organism = synthetic construct
SEQUENCE: 9
tccctttagg gaatgaccct gaagttcatc tgcaccaccg agggaaatcc ctttttcgcc   60
taggttgggt agggtggtgg cg                                             82

SEQ ID NO: 10             moltype = DNA   length = 82
FEATURE                  Location/Qualifiers
source                   1..82
                         mol_type = other DNA
                         organism = synthetic construct
SEQUENCE: 10
ttccctaaag ggatgaccct gaagttcatc tgcaccaccg aagggatttc ccttttcgcc   60
taggttgggt agggtggtgg cg                                             82

SEQ ID NO: 11             moltype = DNA   length = 82
FEATURE                  Location/Qualifiers
source                   1..82
                         mol_type = other DNA
                         organism = synthetic construct
SEQUENCE: 11
cgcctaggtt gggtagggtg gtggcgtttt ccctttaggg aatgaccctg aagttcatct   60
gcaccaccga gggaaatccc tt                                             82

SEQ ID NO: 12             moltype = DNA   length = 82
FEATURE                  Location/Qualifiers
source                   1..82
                         mol_type = other DNA
                         organism = synthetic construct
SEQUENCE: 12
ttccctaaag ggatgaccct gaagttcatc tgcaccaccg aagggatttc ccttttcgcc   60
taggttgggt agggtggtgg cg                                             82

SEQ ID NO: 13             moltype = DNA   length = 82
```

-continued

```
FEATURE                Location/Qualifiers
source                 1..82
                       mol_type = other DNA
                       organism = synthetic construct
SEQUENCE: 13
tccctttagg gaatgaccct gaagttcatc tgcaccaccg agggaaatcc ctttttcgcc   60
taggttgggt agggtggtgg cg                                            82

SEQ ID NO: 14          moltype = DNA   length = 82
FEATURE                Location/Qualifiers
source                 1..82
                       mol_type = other DNA
                       organism = synthetic construct
SEQUENCE: 14
cgcctaggtt gggtagggtg gtggcgtttt tccctaaagg gatgaccctg aagttcatct   60
gcaccaccga agggatttcc ct                                            82

SEQ ID NO: 15          moltype = DNA   length = 82
FEATURE                Location/Qualifiers
source                 1..82
                       mol_type = other DNA
                       organism = synthetic construct
SEQUENCE: 15
cgcctaggtt gggtagggtg gtggcgtttt ccctttaggg aatgaccctg aagttcatct   60
gcaccaccga gggaaatccc tt                                            82

SEQ ID NO: 16          moltype = DNA   length = 82
FEATURE                Location/Qualifiers
source                 1..82
                       mol_type = other DNA
                       organism = synthetic construct
SEQUENCE: 16
cgcctaggtt gggtagggtg gtggcgtttt tccctaaagg gatgaccctg aagttcatct   60
gcaccaccga agggatttcc ct                                            82

SEQ ID NO: 17          moltype = DNA   length = 87
FEATURE                Location/Qualifiers
source                 1..87
                       mol_type = other DNA
                       organism = synthetic construct
SEQUENCE: 17
tccctttagg gaatgaccct gaagttcatc tgcaccaccg agggaaatcc cttttttggtt   60
ggtgtggttg gtggttggtg tggttgg                                       87

SEQ ID NO: 18          moltype = DNA   length = 87
FEATURE                Location/Qualifiers
source                 1..87
                       mol_type = other DNA
                       organism = synthetic construct
SEQUENCE: 18
ttccctaaag ggatgaccct gaagttcatc tgcaccaccg aagggatttc cctttttggtt   60
ggtgtggttg gtggttggtg tggttgg                                       87

SEQ ID NO: 19          moltype = DNA   length = 87
FEATURE                Location/Qualifiers
source                 1..87
                       mol_type = other DNA
                       organism = synthetic construct
SEQUENCE: 19
ggttggtgtg gttggtggtt ggtgtggttg gttttccctt agggaatga ccctgaagtt    60
catctgcacc accgagggaa atccctt                                       87

SEQ ID NO: 20          moltype = DNA   length = 87
FEATURE                Location/Qualifiers
source                 1..87
                       mol_type = other DNA
                       organism = synthetic construct
SEQUENCE: 20
ttccctaaag ggatgaccct gaagttcatc tgcaccaccg aagggatttc cctttttggtt   60
ggtgtggttg gtggttggtg tggttgg                                       87

SEQ ID NO: 21          moltype = DNA   length = 87
FEATURE                Location/Qualifiers
source                 1..87
                       mol_type = other DNA
                       organism = synthetic construct
SEQUENCE: 21
tccctttagg gaatgaccct gaagttcatc tgcaccaccg agggaaatcc cttttttggtt   60
ggtgtggttg gtggttggtg tggttgg                                       87
```

```
SEQ ID NO: 22            moltype = DNA   length = 87
FEATURE                  Location/Qualifiers
source                   1..87
                         mol_type = other DNA
                         organism = synthetic construct
SEQUENCE: 22
ggttggtgtg gttggtggtt ggtgtggttg gtttttccct aaagggatga ccctgaagtt   60
catctgcacc accgaaggga tttccct                                        87

SEQ ID NO: 23            moltype = DNA   length = 87
FEATURE                  Location/Qualifiers
source                   1..87
                         mol_type = other DNA
                         organism = synthetic construct
SEQUENCE: 23
ggttggtgtg gttggtggtt ggtgtggttg gttttccctt agggaatga ccctgaagtt    60
catctgcacc accgagggaa atccctt                                        87

SEQ ID NO: 24            moltype = DNA   length = 87
FEATURE                  Location/Qualifiers
source                   1..87
                         mol_type = other DNA
                         organism = synthetic construct
SEQUENCE: 24
ggttggtgtg gttggtggtt ggtgtggttg gtttttccct aaagggatga ccctgaagtt   60
catctgcacc accgaaggga tttccct                                        87

SEQ ID NO: 25            moltype = DNA   length = 111
FEATURE                  Location/Qualifiers
source                   1..111
                         mol_type = other DNA
                         organism = synthetic construct
SEQUENCE: 25
cgcctaggtt gggtagggtg gtggcgtttt ccctttaggg aatgaccctg aagttcatct   60
gcaccaccga gggaaatccc tttttcgcct aggttgggta gggtggtggc g            111

SEQ ID NO: 26            moltype = DNA   length = 121
FEATURE                  Location/Qualifiers
source                   1..121
                         mol_type = other DNA
                         organism = synthetic construct
SEQUENCE: 26
ggttggtgtg gttggtggtt ggtgtggttg gtttttccct aaagggatga ccctgaagtt   60
catctgcacc accgaaggga tttccctttt ggttggtgtg gttggtggtt ggtgtggttg   120
g                                                                    121

SEQ ID NO: 27            moltype = RNA   length = 27
FEATURE                  Location/Qualifiers
source                   1..27
                         mol_type = other RNA
                         organism = synthetic construct
SEQUENCE: 27
cggtggtgca gatgaacttc agggtca                                        27

SEQ ID NO: 28            moltype = RNA   length = 27
FEATURE                  Location/Qualifiers
source                   1..27
                         mol_type = other RNA
                         organism = synthetic construct
misc_feature             1
                         note = Alexa Fluor 546 NHS Ester
SEQUENCE: 28
cggtggtgca gatgaacttc agggtca                                        27

SEQ ID NO: 29            moltype = RNA   length = 27
FEATURE                  Location/Qualifiers
source                   1..27
                         mol_type = other RNA
                         organism = synthetic construct
misc_feature             1
                         note = Alexa Fluor 750 NHS Ester
SEQUENCE: 29
cggtggtgca gatgaacttc agggtca                                        27

SEQ ID NO: 30            moltype = DNA   length = 27
FEATURE                  Location/Qualifiers
source                   1..27
                         mol_type = other DNA
```

```
                        organism = synthetic construct
SEQUENCE: 30
cggtggtgca gatgaacttc agggtca                                            27

SEQ ID NO: 31          moltype = DNA   length = 82
FEATURE                Location/Qualifiers
source                 1..82
                       mol_type = other DNA
                       organism = synthetic construct
SEQUENCE: 31
cgccaccacc ctacccaacc taggcgaaaa agggatttcc ctcggtggtg cagatgaact   60
tcagggtcat tccctaaagg ga                                            82

SEQ ID NO: 32          moltype = DNA   length = 82
FEATURE                Location/Qualifiers
source                 1..82
                       mol_type = other DNA
                       organism = synthetic construct
SEQUENCE: 32
cgccaccacc ctacccaacc taggcgaaaa gggaaatccc ttcggtggtg cagatgaact   60
tcagggtcat ccctttaggg aa                                            82

SEQ ID NO: 33          moltype = DNA   length = 87
FEATURE                Location/Qualifiers
source                 1..87
                       mol_type = other DNA
                       organism = synthetic construct
SEQUENCE: 33
ccaaccacac caaccaccaa ccacaccaac caaaaaggga tttccctcgg tggtgcagat   60
gaacttcagg gtcattccct aaaggga                                       87

SEQ ID NO: 34          moltype = DNA   length = 87
FEATURE                Location/Qualifiers
source                 1..87
                       mol_type = other DNA
                       organism = synthetic construct
SEQUENCE: 34
agggaaatcc cttcggtggt gcagatgaac ttcagggtca tccctttagg gaaaaaccaa   60
ccacaccaac caccaaccac accaacc                                       87

SEQ ID NO: 35          moltype = DNA   length = 111
FEATURE                Location/Qualifiers
source                 1..111
                       mol_type = other DNA
                       organism = synthetic construct
SEQUENCE: 35
cgccaccacc ctacccaacc taggcgaaaa agggatttcc ctcggtggtg cagatgaact   60
tcagggtcat tccctaaagg gaaaacgcca ccaccctacc caacctaggc g            111

SEQ ID NO: 36          moltype = DNA   length = 121
FEATURE                Location/Qualifiers
source                 1..121
                       mol_type = other DNA
                       organism = synthetic construct
SEQUENCE: 36
ccaaccacac caaccaccaa ccacaccaac caaaagggaa atcccttcgg tggtgcagat   60
gaacttcagg gtcatccctt tagggaaaaa ccaaccacac caaccaccaa ccacaccaac   120
c                                                                  121

SEQ ID NO: 37          moltype = RNA   length = 25
FEATURE                Location/Qualifiers
source                 1..25
                       mol_type = other RNA
                       organism = synthetic construct
SEQUENCE: 37
accctgaagt tcatctgcac caccg                                         25

SEQ ID NO: 38          moltype = RNA   length = 25
FEATURE                Location/Qualifiers
source                 1..25
                       mol_type = other RNA
                       organism = synthetic construct
misc_feature           1
                       note = Alexa Fluor 488 NHS Ester
SEQUENCE: 38
accctgaagt tcatctgcac caccg                                         25

SEQ ID NO: 39          moltype = DNA   length = 25
FEATURE                Location/Qualifiers
```

-continued

```
source              1..25
                    mol_type = other DNA
                    organism = synthetic construct
SEQUENCE: 39
accctgaagt tcatctgcac caccg                                          25
```